US009393271B2

(12) United States Patent
Schally et al.

(10) Patent No.: US 9,393,271 B2
(45) Date of Patent: Jul. 19, 2016

(54) GHRH AGONISTS FOR ISLET CELL TRANSPLANTATION AND FUNCTION AND THE TREATMENT OF DIABETES

(71) Applicants: UNIVERSITY OF MIAMI, Miami, FL (US); U.S.A., REPRESENTED BY THE DEPARTMENT OF VETERANS AFFAIRS, Washington, DC (US); DRESDEN UNIVERSITY OF TECHNOLOGY, Dresden (DE)

(72) Inventors: Andrew V. Schally, Miami Beach, FL (US); Norman L. Block, Hollywood, FL (US); Stefan Bornstein, Dresden (DE); Barbara Ludwig, Dresden (DE)

(73) Assignees: University of Miami, Miami, FL (US); The United States of America, Represented by the Department of Veterans Affairs, Washington, DC (US); Dresden University of Technology, Dresden (DE)

( * ) Notice: Subject to any disclaimer, the term of this patent is extended or adjusted under 35 U.S.C. 154(b) by 195 days.

(21) Appl. No.: 14/138,912

(22) Filed: Dec. 23, 2013

(65) Prior Publication Data
US 2014/0193378 A1 Jul. 10, 2014

Related U.S. Application Data

(60) Provisional application No. 61/745,038, filed on Dec. 21, 2012.

(51) Int. Cl.
| | |
|---|---|
| A61K 38/00 | (2006.01) |
| C07K 16/00 | (2006.01) |
| A61K 35/39 | (2015.01) |
| A61K 38/25 | (2006.01) |
| A61K 35/28 | (2015.01) |
| C07K 14/60 | (2006.01) |

(52) U.S. Cl.
CPC .............. *A61K 35/39* (2013.01); *A61K 35/28* (2013.01); *A61K 38/25* (2013.01); *C07K 14/60* (2013.01)

(58) Field of Classification Search
None
See application file for complete search history.

(56) References Cited

U.S. PATENT DOCUMENTS

| | | | |
|---|---|---|---|
| 4,622,312 A | 11/1986 | Felix et al. | |
| 4,649,131 A | 3/1987 | Felix et al. | |
| 4,689,318 A | 8/1987 | Kaiser et al. | |
| 4,784,987 A | 11/1988 | Rivier et al. | |
| 4,914,189 A | 4/1990 | Schally et al. | |
| 5,262,519 A | 11/1993 | Rivier et al. | |
| 5,756,458 A | 5/1998 | Kubiak et al. | |
| 5,792,747 A | 8/1998 | Schally et al. | |
| 5,846,936 A | 12/1998 | Felix et al. | |
| 6,458,764 B1 | 10/2002 | Gravel et al. | |
| 7,241,744 B2 | 7/2007 | Draghia-Akli et al. | |
| 7,268,113 B2 | 9/2007 | Bridon et al. | |
| 7,928,063 B2 | 4/2011 | Izdebski et al. | |
| 8,507,433 B1 | 8/2013 | Schally et al. | |
| 2005/0261201 A1 | 11/2005 | Polvino et al. | |
| 2007/0042950 A1 | 2/2007 | Schally et al. | |
| 2009/0023646 A1 | 1/2009 | Gaudreau | |
| 2010/0092539 A1 | 4/2010 | Schally et al. | |
| 2010/0272697 A1 | 10/2010 | Naji et al. | |
| 2011/0129497 A1 | 6/2011 | Bonnin et al. | |
| 2013/0195807 A1 | 8/2013 | Schally et al. | |
| 2013/0261058 A1 | 10/2013 | Schally et al. | |
| 2014/0057847 A1 | 2/2014 | Schally et al. | |
| 2014/0058068 A1 | 2/2014 | Schally et al. | |
| 2014/0179604 A1 | 6/2014 | Schally et al. | |

FOREIGN PATENT DOCUMENTS

| | | |
|---|---|---|
| CN | 1328570 A | 12/2001 |
| CN | 1871020 A | 11/2006 |
| EP | 0413839 | 2/1991 |
| WO | WO9012810 A1 | 11/1990 |
| WO | WO 94/11396 A1 | 5/1994 |
| WO | WO9622782 A1 | 8/1996 |
| WO | WO9742223 A1 | 11/1997 |
| WO | WO03037928 A2 | 5/2003 |

(Continued)

OTHER PUBLICATIONS

Hogland et. al. JOP. J Pancreas, May 18, 2009; 10(3):242-248.*
Idebski et. al. Proc. Natl. Acad. Sci. USA vol. 92, pp. 4872-4876, May 1995 Medical Sciences.*
Zarandi, Int.J. Peptide Protein Res. 39:211-217, 1992.*
Armann et al., "Quantification of basal and stimulated ROS levels as predictors of islet potency and function," *Am J Transplant*, (2007), 7:38-47.
Bajusz et al. In *Peptides*, 1982, Blaha and Melon, Eds. de Gruyter, Berlin-N.Y., 1983, pp. 643-647.

(Continued)

*Primary Examiner* — Jeanette Lieb
(74) *Attorney, Agent, or Firm* — Pepper Hamilton LLP

(57) ABSTRACT

Disclosed herein are compositions of GHRH agonists and peptides, and methods to treat diabetes. In one embodiment, a method of promoting survival of grafted cells and/or tissues may involve exposing the cells and/or tissues to an effective amount of at least one agonist of GHRH. In some embodiments, the grafted cells and/or tissues may be pancreatic cells. In some embodiments, the grafted cells may be islet cells co-cultured with non-pancreatic cells. In a further embodiment, a method of treating a patient diagnosed with diabetes involves transplanting and/or grafting the islet cells and/or tissues comprising islet cells into a patient, and administering a therapeutically effective amount of at least one agonist of GHRH to the patient. In some embodiments, the islet cells and/or tissues comprising islet cells may be optionally exposed to GHRH and/or at least one agonist of GHRH prior to transplantation into a patient. In some embodiments, the at least one agonist of GHRH is administered pre-transplantation, concurrently with transplantation, post-transplantation or any combinations thereof.

22 Claims, 10 Drawing Sheets

(56) References Cited

FOREIGN PATENT DOCUMENTS

| | | |
|---|---|---|
| WO | WO 2009/009727 A2 | 1/2009 |
| WO | WO2011034976 A1 | 3/2011 |
| WO | WO 2011/153491 A2 | 12/2011 |
| WO | WO2011153491 A2 | 12/2011 |
| WO | WO 2012/037519 A2 | 3/2012 |
| WO | WO 2013/095903 A1 | 6/2013 |

OTHER PUBLICATIONS

Bonner-Weir, "In vitro cultivation of human islets from expanded ductal tissue," *Proc Natl Acad Sci USA*, (Jul. 5, 2000), 97(14):7999-8004.

Cai et al., "Synthesis of new potent agonistic analogs of growth hormone-releasing hormone (GHRH) and evaluation of their endocrine and cardiac activities," *Peptides* (Feb. 2014), 52:104-112. Epub: Dec. 25, 2013.

Campbell et al., "GRF analogs and fragments: Correlation between receptor binding, activity and structure," *Peptides* (May/Jun. 1991), 12(3):569-574.

Corpas et al., "Growth Hormone (GH)-Releasing Hormone-(1-29) Twice Daily Reverses the Decreased GH and Insulin-Like Growth Factor-I Levels in Old Men", *J. Clin. Endoc. Metabol.*, (Aug. 1992) 75(2):530-535.

Dor et al. "Adult pancreatic B-cells are formed by self-duplication rather than stem-cell differentiation," *Nature*, (May 6, 2004), 429:41-44.

Falutz et al., "Effects of Tesamorelin, a Growth Hormone-Releasing Factor, in HIV_Infected Patients with Abdominal Fat Accumulation: A Randomized Placebo-Controlled Trial With a Safety Extension," *Acquir Immune Defic Syndr.* (2010), 53: 311-322.

Felix et al., "Synthesis, biological activity and conformational analysis of cyclic GRF analogs," *Int. J. Peptide Protein Res.* (Dec. 1988), 32(6): 441-454.

Ferninandi et al., "Non-Clinical Pharmacology and Safety Evaluation of TH9507, a Human Growth Hormone-Releasing Factor Analogue," *Basic & Clin Pharmacol Toxicol.* (2007), 100: 49-58.

Fiaschi-Taesch et al., "Hepatocyte Growth Factor Enhances Engraftment and Function of Nonhuman Primate Islets," *Diabetes*, (Oct. 2008), 57:2745-2754.

Frohman et al., "Dipeptidylpeptidase IV and Trypsin-like Enzymatic Degradation of Human Growth Hormone-releasing Hormone in Plasma," *J. Clin. Invest.* (1989), 83:1533-1540.

Goodman & Gilman's The Pharmaceutical Basis of Therapeutics, 6$^{th}$ Ed., MacMillan Publishing Co., New York, (1980).

Granata et al., "Obestatin promotes survival of pancreatic beta-cells and human islets and induces expression of genes involved in the regulation of beta-cell mass and function," *Diabetes*, (Apr. 2008), 57:967-979.

Granata et al. "Growth hormone-releasing hormone promotes survival of cardiac myocytes in vitro and protects against ischaemia-reperfusion injury in rat heart", *Cardiovasc Res*, (Mar. 17, 2009) 83:303-312.

Guarcello et al., "Growth hormone releasing hormone receptors on thymocytes and splenocytes from rats," *Cell Immunol*, (1991), 136:291-902.

Havt et al., "The expression of the pituitary growth hormone-releasing hormone receptor and its splice variants in normal and neoplastic human tissues," *Proc Natl Acad Sci USA* (Nov. 29, 2005), 102(48):17424-17429.

Houssay, "[Role of the hypophysis in carbohydrate metabolism and diabetes]," *Folia Endoctrinol Mens Incretologia Incretoterapia*,(1950) 3 (2): 127-136.

Huising et al., "CRFR1 is expressed on pancreatic B cells, promotes B cell proliferation, and potentiates insulin secretion in a glucose-dependent manner," *Proc Natl Acad Sci USA*, (Jan. 12, 2010), 107(2): 912-917.

International Search Report for PCT/US2011/039162 dated Feb. 29, 2012.

International Search Report for PCT/US2013/077514 dated Jul. 10, 2014.

Izdebski et al., "Synthesis and biological evaluation of superactive agonists of growth hormone-releasing hormone," *Proc. Natl. Acad. Sci. USA*, (May 1995), 92:4872-4876.

Jabs et al., "Reduced insulin secretion and content in VEGF-a deficient mouse pancreatic islets," *Exp Clin Endoctrinol Diabetes* (2008), 116 Suppl. 1:S46-49.

Kanashiro-Takeuchi, et al. "Cardioprotective effects of growth hormone-releasing hormone agonist after myocardial infarction", *Proc Natl Acad Sci USA*, (Jan. 21, 2010) 107(6):2604-2609.

Khorram et al., "Effects of [Norleucine27] Growth Hormone-Releasing Hormone (GHRH) (1-29)-NH2 Administration on the Immune System of Aging Men and Women," *J Clin Endocrinol Metab*, (1997), 82(11):3590-3596.

Kirk et al., "Treatment with GHRH(1-29)NH2 in children with idiopathic short stature induces a sustained increase in growth velocity," *Clinical Endocrinol.* (Oct. 1994) 41(4):487-493.

Kovacs et al., "An evaluation of intravenous, subcutaneous, and in vitro activity of new agmatine analogs of growth-hormone releasing hormone hGH-RW (1-29)NH2," *Life Science*, (1988), 42(1): 27-35.

Lehmann et al., "Has time come for new goals in human islet transplantation?," *Am J Transplant*, (2008), 8:1096-1100.

Letsch et al., "Growth hormone-releasing hormone (GHRH) antagonists inhibit the proliferation of androgen-dependent and -independent prostate cancers," *Proc Natl Adac Sci USA*, (Feb. 4, 2003), 100(3):1250-1255.

Ling et al., "Isolation, primary structure, and synthesis of human hypothalamic somatocrini: growth hormone-releasing factor," *Proc Natl Acad Sci USA*, (1984), 81:4302-4306.

Merrifield, Solid Phase Peptide Synthesis. I. The Synthesis of a Tetrapeptide, *Journal of the American Chemical Society*, (1963), 85(14):2149-2154.

Modern Pharmaceutics, Banker & Rhodes, Marcel Dekker, Inc., New York and Basel, (1979).

Muranishi et al., "Lipophilic Peptides: Synthesis of Lauroyl Thyrotropin-Releasing Hormone and Its Biological Activity," *Pharm. Res.* (May 1991), 8(5)649-652.

Nielsen et al., "Beta cell proliferation and growth factors," *J. Mol. Med.* (1999), 77:62-66.

Rekasi et al., "Isolation and sequencing of cDNAs for splice variants of growth hormone-releasing hormone receptors from human cancers," *Proc Natl Acad Sci USA*, (Sep. 12, 2000), 97(19): 10561-10566.

Ross et al., "Treatment of Growth-Hormone Deficiency with Growth-Hormone-Releasing Hormone," *Lancet 1* (Jan. 3, 1987), 8523:5-8.

Schally et al., *Growth Hormone Secretagogues in Clinical Practice*, (Ch. 10), (1998), pp. 131-142, Marcel Dekker, Inc., New York.

Shapiro et al., "International trial of the Edmonton protocol for islet transplantation," *N Engl J Med*, (2006), 355:1318-1330.

Schubert et al., "Transplantation of pancreatic islets to adrenal gland is promoted by agonists of growth-hormone-releasing hormone," *Proc. Natl. Acad. Sci. USA*, (Feb. 5, 2013), 110(6):2288-2293.

Takano et al., "Human growth hormone-releasing hormone (hGH-RH; hGRF) treatment of four patients with GH deficiency," *Endocrinol. Japan* (1988) 35(5); 775-781.

Thorner et al., "Acceleration of Growth in Two Children Treated with Human Growth Hormone-Releasing Factor," *N. Engl. J. Med.* (Jan. 3, 1985), 312(1):4-9.

Vance, "Growth-Hormone-Releasing Hormone," *Clin Chem*, (1990), 36:415-420.

Vance, "Growth hormone for the elderly?," *N. Eng. J. Med* (1990), 323(1):52-54.

Vasavada et al., "Growth factors and beta cell replication," *Int J. Biochem Cell Biol, Epub 31*, (Aug. 2005), 38(5-6):931-950.

Zarandi et al., "Synthesis and in vitro and in vivo activity of analogs of growth hormone-releasing hormone (GH-RH) with C-terminal agmatine," *Int. J. Peptide Protein Res.* (Dec. 1990), 36(6):499-505.

Ziegler et al., "Dehydroepiandrosterone induces a neuroendocrine phenotype in nerve growth factor-stimulated chromaffin pheochromocytoma PC12 cells," *Endocrinology*, (2008), 149:320-328.

(56) References Cited

OTHER PUBLICATIONS

Ziegler et al., "Expression of neuropeptide hormone receptors in human adrenal tumors and cell lines: Antiproliferative effects of peptide analogues," *Proc Natl Acad Sci USA*, (Sep. 15, 2009), 106(37):15879-15884.

Campbell, R. M. et al., "Rational Design, Synthesis and Biological Evaluation of Novel Growth Hormone Releasing Factor Analogues", *Biopolymers* 37(2), Jan. 1, 1995.

Office Action cited in Chinese Application No. 201280070383.9 issued Oct. 21, 2015.

Supplementary European Search Report for EP12860298 dated Sep. 11, 2015.

Witkowska E.W. et al., "Tryptic Hydrolysis of HGH-RH(1-29)-NH2 Analogues Containing Lys or Orn in Positions 21 and 21", *Journal of Peptide Science*, 7(1), Jan. 1, 2001.

\* cited by examiner

GHRH AGONISTS FOR ISLET CELL TRANSPLANTATION AND FUNCTION AND THE TREATMENT OF DIABETES

CROSS-REFERENCE TO RELATED APPLICATIONS

This application claims priority to U.S. Provisional Application No. 61/745,038 filed on Dec. 21, 2012, which is hereby incorporated by reference in its entirety.

GOVERNMENT INTERESTS

This work was supported by Medical Research Service grants from the Veterans Affairs Department, USA. The government may have certain rights in this application.

BRIEF SUMMARY OF THE INVENTION

Embodiments of the present disclosure are directed to GHRH agonists and peptide compositions, and methods to treat diabetes. In one embodiment, a method of promoting survival of grafted cells and/or tissues may involve exposing the cells and/or tissues to an effective amount of a GHRH agonist peptide. In some embodiments, the grafted cells and/or tissues may be pancreatic cells. In some embodiments, the grafted cells may be islet cells co-cultured with non-pancreatic cells. In a further embodiment, a method of treating a patient diagnosed with diabetes involves transplanting and/or grafting the islet cells and/or tissues comprising islet cells into a patient, and administering a therapeutically effective amount of a GHRH agonist peptide. In some embodiments, the islet cells and/or tissues comprising islet cells may be optionally exposed to to the GHRH agonist peptide prior to transplantation into a patient. In some embodiments, the GHRH agonist peptide is administered pre-transplantation, concurrently with transplantation, post-transplantation or any combinations thereof.

In additional embodiment, a method of modulating function of an insulin producing cell or a tissue in vitro and/or in vivo may involve exposing the insulin producing cell or the tissue to an effective amount of a GHRH agonist peptide. In some embodiments, the insulin producing cell may be an islet cell or a cell expressing a recombinant insulin molecule. In some embodiments, the cell expressing the recombinant insulin molecule may be a stem cell, a pancreatic cell, a transformed cell, a microbe or a cell sensitive to GHRH.

In a further embodiment, a method of transplanting and/or grafting insulin producing cells/tissues into a diabetic mammal in need thereof may involve transplanting and/or grafting the insulin producing cells/tissues into an adrenal gland of the diabetic mammal, and administering a therapeutically effective amount of a GHRH agonist peptide to the diabetic mammal.

In the foregoing embodiments, the GHRH agonist peptide comprises a peptide of formula:

[R$_1$-A$^1$-A$^2$-Asp-Ala-Ile-A$^6$-Thr-A$^8$-Ser-Tyr-A$^{11}$-A$^{12}$-Val-Leu-A$^{15}$-Gln-Leu-Ser-Ala-A$^{20}$-A$^{21}$-A$^{22}$-Leu-Gln-Asp-Ile-Nle$^{27}$-A$^{28}$-A$^{29}$-A$^{30}$]-R$_2$, wherein R$_1$ is Ac, Tfa, or is absent,
A$^1$ is Tyr, Dat, or N-Me-Tyr,
A$^2$ is Ala, D-Ala, Abu, or D-Abu,
A$^6$ is Phe or Fpa5,
A$^8$ is Asn, Ala, Gln, Thr, or N-Me-Ala,
A$^{11}$ is Arg, His, or Har,
A$^{12}$ is Orn, or Lys(Me)$_2$,
A$^{15}$ is Abu or Ala,
A$^{20}$ is Arg, His, or Har,
A$^{21}$ is Orn, or Lys(Me)$_2$,
A$^{22}$ is Leu, or Orn,
A$^{28}$ is Ser, or Asp,
A$^{29}$ is Arg, Har, Agm, D-Arg, or D-Har,
A$^{30}$ is Arg, Agm, Ada, Amc, Aha, Apa, Har, D-Arg, D-Har, Gab, Gln, D-Gln, Gln-Gab, D-Gln-Gab, or is absent,
R$_2$ is —NH$_2$, —NH—CH$_3$, —NH—CH$_2$—CH$_3$, —OH, —NHR$_3$, —N(R$_3$)$_2$, or —OR$_3$, wherein R$_3$ is any of C$_{1-12}$ alkyl, C$_{2-12}$ alkenyl, or C$_{2-12}$ alkynyl,
and pharmaceutically acceptable salts thereof, and wherein the agonist peptide is different from SEQ ID NO: 1 in at least one amino acid residue.

DETAILED DESCRIPTION

Figure 1:
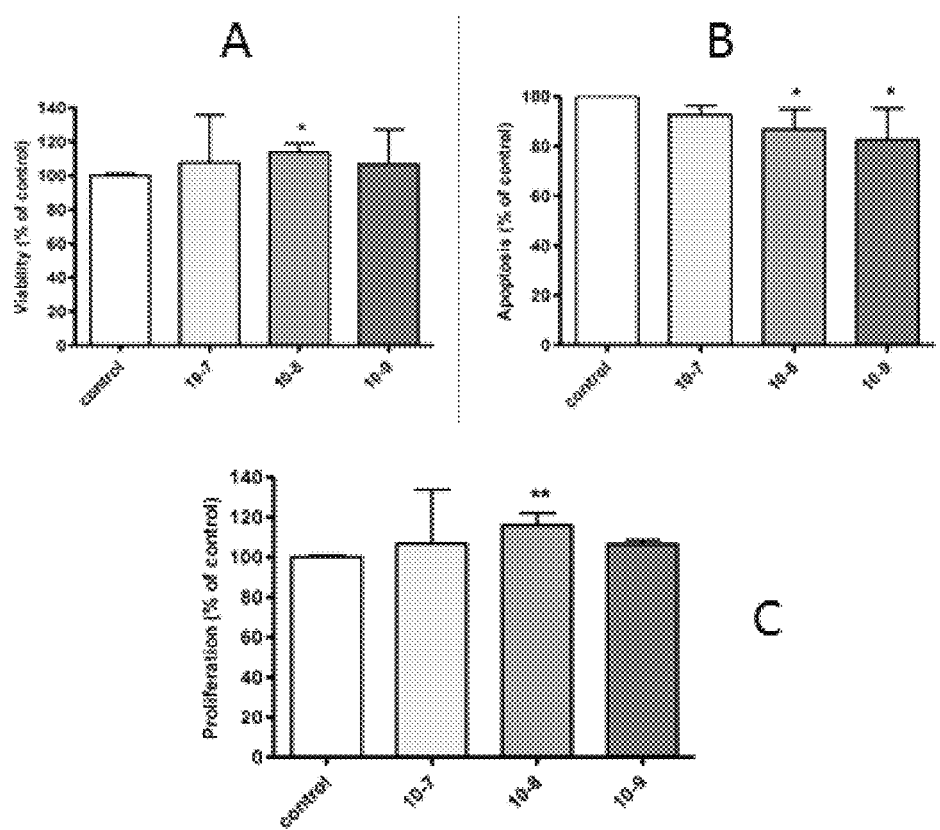
FIG. 1 illustrates the effects of GHRH agonist P-27403 on INS-1 cells in vitro. (A) P-27403 ($10^{-8}$ M) significantly improved viability (15% compared to control) after 24 hrs in culture (n=3) after treatment. (B) Apoptosis as indicated by activity of caspases 3/7 was significantly reduced by 14% ($10^{-8}$ M) or 18% ($10^{-9}$ M) after treatment with P-27403 for 24 hrs (n=4). (C) P-27403 significantly stimulated cell proliferation (16% versus control) after 24 hrs in culture (n=3). **$p<0.01$; *$p<0.05$.

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

As used herein and in the appended claims, the singular forms "a", "an", and "the" include plural reference unless the context clearly dictates otherwise. Thus, for example, reference to an "antioxidant" is a reference to one or more antioxidants and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic to a patient whereby the therapeutic positively impacts the tissue to which it is targeted. The peptides/compounds described herein can be administered either alone or in combination (concurrently or serially) with other pharmaceuticals. For example, the peptides/compounds can be administered in combination with other anti-cancer or anti-neoplastic agents, or in combination with other cancer therapies other than chemotherapy, such as, for example, surgery or radiotherapy. In some embodiments, the peptides/compounds described herein can also be administered in combination with (i.e., as a combined formulation or as separate formulations) with antibiotics.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, prevent or improve an unwanted condition, disease or symptom of a patient.

A "therapeutically effective amount" or "effective amount" of a composition is a predetermined amount calculated to achieve the desired effect, i.e., to ameliorate, prevent or improve an unwanted condition, disease or symptom of a patient. The activity contemplated by the present methods includes both therapeutic and/or prophylactic treatment, as appropriate. The specific dose of the peptides/compounds or the peptides administered according to this invention to obtain therapeutic and/or prophylactic effects will, of course, be determined by the particular circumstances surrounding the case, including, for example, the peptides/compounds administered, the route of administration, and the condition being treated. The effective amount administered may be determined by a physician in the light of the relevant circumstances including the condition to be treated, the choice of peptides/compounds to be administered, and the chosen route of administration. A therapeutically effective amount of the peptide/compound of this invention is typically an amount such that when it is administered in a physiologically tolerable excipient composition, it is sufficient to achieve an effective systemic concentration or local concentration in the target tissue.

Generally speaking, the term "tissue" refers to any aggregation of similarly specialized cells which are united in the performance of a particular function.

As used herein, "analog" of polypeptides refers to an amino acid sequence that is altered by one or more amino acid residues. The analog may have "conservative" changes, wherein a substituted amino acid has similar structural or chemical properties (e.g., replacement of leucine with isoleucine). More rarely, an analog may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

By the term "modulate," it is meant that any of the mentioned activities, are, e.g., increased, enhanced, increased, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values. Modulation can also normalize an activity to a baseline value.

The terms "subject", "patient" or "individual" are used interchangeably herein, and refers to a mammalian subject to be treated. In some embodiments, the patient is a human. In some cases, the methods can be used in experimental animals, in veterinary application, and in the development of animal models for disease, including, but not limited to, rodents including mice, rats, and hamsters; and primates. In some embodiments, the patient is a patient in need thereof.

As used herein, the phrase "in need thereof" means that the patient has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent.

"Treatment" is an intervention performed with the intention of preventing the development or altering the pathology or symptoms of a disorder. Accordingly, "treatment" can refer to therapeutic treatment or prophylactic or preventative measures. In some embodiments, the treatment is for therapeutic treatment. In some embodiments, the treatment is for prophylactic or preventative treatment. Those in need of treatment can include those already with the disorder as well as those in which the disorder is to be prevented.

As used herein, "ameliorated" or "treatment" refers to a symptom which is approaches a normalized value (for example a value obtained in a healthy patient or individual), e.g., is less than 50% different from a normalized value, is less than about 25% different from a normalized value, is less than 10% different from a normalized value, or is not significantly different from a normalized value as determined using routine statistical tests.

Generally speaking, the term "tissue" refers to any aggregation of similarly specialized cells which are united in the performance of a particular function.

As used herein, the term "therapeutic" means a peptide/agent/compound utilized to discourage, combat, ameliorate, prevent or improve an unwanted condition, disease or symptom of a patient.

A "therapeutically effective amount" or "effective amount" of an agent or a peptide is a predetermined amount calculated to achieve the desired effect, i.e., to ameliorate, prevent or improve an unwanted condition, disease or symptom of a patient. The activity contemplated by the present methods includes both therapeutic and/or prophylactic treatment, as appropriate. The specific dose of the peptides/agents administered according to the methods described herein to obtain therapeutic and/or prophylactic effects will, of course, be determined by the particular circumstances surrounding the case, including, for example, the peptides/agents administered, the route of administration, and the condition being treated. The effective amount administered may be determined by a physician in the light of the relevant circumstances including the condition to be treated, the choice of peptides/agents to be administered, and the chosen route of administration. A therapeutically effective amount of the peptides/agent is typically an amount such that when it is administered in a physiologically tolerable excipient composition, it is sufficient to achieve an effective systemic concentration or local concentration in the target tissue. The peptides can also be administered without excipients.

"Agonist of GHRH" means a compound or peptide other than GHRH which has the function of binding to and stimulating GHRH receptors, resulting in the release of growth hormone, or another physiological, endocrine or cellular response specific for GHRH. In some embodiments, a GHRH agonist may activate GHRH receptor and may not result in the release of growth hormone. A GHRH agonist may comprise a full length GHRH sequence in which certain modifications have been made, e.g., amino acid residues have been substituted, side groups have been added. The amino acid sequence of GHRH (1-30), starting at the N-terminal part is: $Tyr^1$-$Ala^2$-$Asp^3$-$Ala^4$-$Ile^5$-$Phe^6$-$Thr^7$-$Asn^8$-$Ser^9$-$Tyr^{10}$-$Arg^{11}$-$Lys^{12}$-$Val^{13}$-$Leu^{14}$-$Gly^{15}$-$Gln^{16}$-$Leu^{17}$-$Ser^{18}$-$Ala^{19}$-$Arg^{29}$-$Lys^{21}$-$Leu^{22}$-$Leu^{23}$-$Gln^{24}$-$Asp^{25}$-$Ile^{26}$-$Met^{27}$-$Ser^{28}$-$Arg^{29}$-$Gln^{39}$ (SEQ ID NO: 1). A GHRH agonist may comprise a GHRH sequence to which amino acid deletions, insertions, and/or substitutions have been made. A GHRH agonist may also be a fragment or modified fragment of GHRH having the capability to bind to the GHRH receptor and stimulate release of growth hormone. The biological activity of GHRH is understood to reside in the N-terminal amino acid sequences of the hormone. Thus, fragments or modified fragments between amino acid residues 1 and 30, or between amino acid residues 1 and 29 are expected to be useful.

For example, an agonist of GHRH can include one or more features that protect it against degradation by biological, chemical, and/or other processes. For example, such features can protect the GHRH agonist peptide from proteolytic enzymes in the wound milieu (fluids), e.g., from proteases secreted by neutrophils. Such proteolytic enzymes can inactivate (e.g., degrade or split) unprotected peptides such as unprotected GHRH. Such protective features can include, for example, the replacement of certain amino acids (residues) in the native peptide sequence of GHRH with other different amino acids (residues). In some embodiments, replacement of Arg in position 29 by Agm (agmatine, 4-guanidino-butylamine) may provide resistance to enzymatic degradation of the peptide at the C-terminus. In some embodiments, replacement of Tyr in position 1 by des-aminotyrosine (Dat) may result in peptides with increased biological activities as a result of the resistance to N-terminal enzymatic degradation. Similarly, substitutions of hydrophobic groups at the C-terminal of peptides can result in significant increase in specific activity of the peptides.

Diabetes occurs when there is a critical reduction in islet mass and function that prevents an adequate insulin response to a carbohydrate stimulus. For a long time, insulin has been the only available therapy for the treatment of type I and type II diabetes and other conditions related to lack of or diminished production of insulin. Without wishing to be bound by theory, it is well established that at the onset of type I diabetes, patients have already lost at least 90% of their islets and their number of islets continues to steadily decline. In addition, it become clear is that not only in type I diabetes is there a deficit of islet mass, but also at the time of diagnosis of type II diabetes, patients exhibit a loss of at least 50% of the islet mass and number. As with type I patients, the number and mass of islets continues to decline in type II diabetes, not from autoimmune attack, but because the beta cells effectively become "burned out".

Despite steady improvement in insulin formulations and technically controlled application methods, complete normalization of metabolic control and prevention of blood glucose excursions is achieved only rarely in patients with diabetes mellitus. Patients with insufficient glucose control are at risk for the development of micro- and macrovascular complications. Transplantation of pancreatic islet cells is a valid treatment option for selected patients with type I and type II diabetes. Significant progress has been made over the past decade with the introduction of improved immunosuppressive protocols and with isolation of high quality human islets for clinical transplantation. However, insufficient engraftment and progressive loss of transplanted islets constitute critical limitations of islet transplantation. In many instances, transplanted isltes are poorly viable in part, due to damage either during retrieval and isolation, or due to collapse of the islet structure resulting from insufficient vascularization, continuous hypoxia and lack of regeneration/proliferation post transplantation. Therefore, efforts to improve islet survival and growth post transplantation are desired.

The present disclosure demonstrates the function of GHRH agonists in promoting islet graft survival and function, which may help to reduce the islet mass necessary to reverse diabetes. In some embodiments, a method of promoting survival of grafted cells and/or tissues may involve exposing the cells and/or tissues to an effective amount of at least one agonist of GHRH. In some embodiments, the grafted cells and/or tissues may be pancreatic cells. In some embodiments, the grafted cells/tissues may be a part, portion or biopsy of a donor pancreas which comprises insulin-producing cells. In still other embodiments, the grafted islet cells may be isolated or suspended islets or islet cells, including cells withdrawn or excised from a fetal or adult donor, cadever, cells maintained in primary culture, or an immortalized cell line. In some embodiments, the grafted cells may be islet cells co-cultured with non-pancreatic cells. The islet cells may be co-cultured with any non-pancreatic cells, such as but not limited to, hepatice cells, adrenal cells, stem cells, neuronal cells, adipocytes, skeletal muscle cells, cardiomyocytes and osteoblasts. In some embodiments, the method comprises exposing the grafted cells/tissues to at least one GHRH agonist peptide, or a combination of GHRH agonist peptides to achieve the desired effect.

In some embodiments, the GHRH agonists may improve survival and growth of immortalized rodent and other mammalian insulin producing cells, such as INS-1 cells, isolated mammalian islets, and pancreatic β-cells co-cultured with adrenal cells in vitro. It is known that GHRH receptor is expressed in many non-neuronal cells, such as adrenal cells and pancreatic islets, and thus GHRH may act independently of pituitary GH in mediating its effects. In some embodiments, the GHRH agonists may cause a significant increase in cell viability and proliferation, and block apoptosis in INS-1 cells, isolated mammalian islets, and adrenal-β-cell co-cultures. In some embodiments, the viability of isolated pancreatic islets or any insulin producing cells may increase after treatment with the GHRH agonists, when cultured alone or in co-culture with non-pancreatic cells.

In additional embodiments, a method of treating a patient diagnosed with diabetes may involve transplanting and/or grafting the islet cells and/or tissues comprising islet cells into a patient, and administering a therapeutically effective amount of at least one agonist of GHRH to the patient. The patient may be a type I or type II diabetic. In some embodiments, the donor islet cells comprise a part, portion or biopsy of a donor pancreas which comprises insulin-producing cells. In still other embodiments, the donor islet cells comprise isolated or suspended islets or islet cells, including cells withdrawn or excised from a fetal or adult donor, cadaver, cells maintained in primary culture, or an immortalized cell line. In some embodiments, the transplanted islet cell and/or tissue may be syngeneic, or xenogeneic. Other sources of insulin-producing cells include islet progenitor cells, such as fetal cells or stem cells, optionally expanded in primary culture. Any appropriate cell type can be used, however, including cells harboring exogenous genetic material encoding an expressible insulin gene. Thus, the invention encompasses the use of transfected or transformed host cells, which have been (or are derived from ancestor cells which have been) engineered to express insulin, either constitutively or inducibly (e.g., under control of a glucose-responsive promoter or enhancer). In other embodiments, the invention encompasses the use of pancreatic or other donor cell types derived from a transgenic mammal that has been engineered to include genetic material necessary for the production of insulin in some or all of its body tissues. In some embodiments, the method comprises administering at least one GHRH agonist peptide, or a combination of GHRH agonist peptides to achieve the desired effect.

In some embodiments, the islet cells and/or tissues comprising islet cells may be optionally exposed to GHRH and/or at least one agonist of GHRH prior to transplantation into a patient. In some embodiments, the GHRH and/or the at least one agonist of GHRH is administered pre-transplantation, concurrently with transplantation, post-transplantation or any combinations thereof. In a further embodiment of the method of the present invention, an anti-inflammatory or immunosuppressive drug may be administered to a patient prior to, following, or concurrently with the combination of GHRH agonists described herein above. In some embodiments, the GHRH agonists may be administered to a diabetic patient who has not undergone islet transplantation.

In additional embodiments, a method of modulating function of an insulin producing cell or a tissue in vitro and/or in vivo may involve exposing the insulin producing cell or the tissue to an effective amount of at least one agonist of GHRH. In some embodiments, the insulin producing cell may be an islet cell or a cell expressing a recombinant insulin molecule. In some embodiments, the cell expressing the recombinant insulin molecule may be a stem cell, a pancreatic cell, a transformed cell, a microbe, a cell sensitive to GHRH or any one of the insulin producing cells or tissues described herein.

In some embodiments, the method comprises exposing the insulin producing cell to at least one GHRH agonist peptide, or a combination of GHRH agonist peptides to achieve the desired effect.

Currently more than 90% of clinical islet transplantations are performed by infusion into the portal vein with subsequent embolization to the liver. Although the liver site has been extremely well characterized, it remains suboptimal as up to 60% of islets transplanted there die shortly after transplantation. Without wishing to be bound by theory, a major reason for this massive islet loss is that the hepatic parenchymal oxygen tension is well below that of the pancreas. In addition, the frequent changes in blood glucose levels and high glucose concentrations are known to be deleterious to the islets. Therefore, many studies have pursued alternative sites with more adequate microenvironment for pancreatic islet transplantation.

The present disclosure teaches the use of adrenal glands as an alternate site for islet transplantation. In a further embodiment, a method of transplanting and/or grafting insulin producing cells/tissues into a diabetic mammal in need thereof may involve transplanting and/or grafting the insulin producing cells/tissues into an adrenal gland of the diabetic mammal, and administering a therapeutically effective amount of growth hormone releasing hormone (GHRH) and/or at least one agonist of GHRH to the diabetic mammal.

The adrenal gland may offer the unique features favouring its use as a transplantation site for pancreatic islets, because of high oxygen tension through a dense vascularization, a high endothelial cell content, and local anti-inflammatory and immunoprotective environment. In addition, the adrenal gland may serve as a site for islet transplantation for the following reasons: (i) adrenal glands and pancreas are both endocrine tissues with similar microenvironment; (ii) the unique feature of extensive vascularization of the adrenal gland, which reduces hypoxia stress; (iii) the hypothesis of anti-apoptotic and pro-proliferative effects of various signalling molecules within the adrenal; and (iiii) the unique advantage of a local anti-inflammatory and immunosuppressive microenvironment.

The adrenal gland receives greater amount of perfusion than any other organ for its size. Each adrenal cell is in direct contact with an endothelial cell. This intimate interaction between endothelial cells and adrenal cells provides crucial trophic signals for cortical cells as well as neuroendocrine chromaffin cells. The highly vascularized tissue provides an ideal niche to study β-cell-endothelial cell interactions. Furthermore, this crosstalk between β-cell-endothelial cell can be ideally studied under growth hormone and GHRH stimulation, which are known to be critical for the trophic effect of adrenal vasculature and β-cell survival. These unique properties make the adrenal gland a suitable transplant site for pancreatic islets.

In some embodiments, pretreatment of islets with GHRH agonists before transplantation may result in improved viability. In some embodiments, this effect may be even more pronounced when the GHRH analog is administered to islet-adrenal co-culture systems. In some embodiments, co-culturing of islets with adrenal cells without any exposure to GHRH agonists may also improve the viability of islet cells. There is an established functional interaction of the GHRH-GH-IGF-1 axis with both the islets and adrenal cells that may represent the common denominator for this effect. GHRH peptides, growth hormone, and IGF are crucial factors in providing a trophic stimulus on the adrenal cortex and are potent regulators of steroid metabolism both in the adrenal and the periphery including islets. Thus, GHRH-receptor agonists may have the potential not only to improve islet function but also to promote engraftment and integration of islets in the adrenal microenvironment.

Disclosed herein are a novel series of synthetic peptide analogs of hGHRH(1-29)NH$_2$ or hGHRH(1-30)NH$_2$. The novel synthetic peptides of this invention exhibit high activities in stimulating the release of pituitary growth hormone (GH) in animals, including humans. They also show extremely high binding capacity to the hGHRH receptor. These synthetic hGHRH analogs also retain their physiological activity in solution for an extended period of time and resist enzymatic degradation in the body. The stronger GH releasing potencies of the new analogs in vivo, as compared to previously described ones, results from combination of replacements in hGHRH(1-29)NH$_2$ or hGHRH(1-30)NH$_2$ and from resistance to in vivo degradation. Without in any way limiting the invention or its scope, applicants wish to express their understanding that the retention of activity in vitro and resistance to in vivo degradation are due to multiple substitutions in the molecule: incorporation of N-Me-Tyr or des-amino-Tyr (Dat) in position 1 which protect peptides from the degradation at the N-terminus; incorporation of agmatine (Agm) or —NH—CH$_3$ or —NH—CH$_2$—CH$_3$ at position 29 or extension of the C-terminus with an omega-amino acid which protects peptides from degradation at the C-terminus; and also the replacements of both lysines in the synthetic peptides with ornithine (Orn), which is a poor substrate for trypsin-like enzymes; Gly at residue 15 by Abu. To increase chemical stability, Asn at position 8 is replaced by Gln, Thr, or Ala. And Met in position 27 is replaced by norleucine (Nle). Replacement of other residues in the peptides and the combination of these replacements also are found to promote biological activity.

In some embodiments, the GHRH agonist peptide is represented by the formula:

[R$_1$-A$^1$-A$^2$-Asp-Ala-Ile-A$^6$-Thr-A$^8$-Ser-Tyr-A$^{11}$-A$^{12}$-
Val-Leu-A$^{15}$-Gln-Leu-Ser-Ala-A$^{20}$-A$^{21}$-A$^{22}$-
Leu-Gln-Asp-Ile-Nle$^{27}$-A$^{28}$-A$^{29}$-A$^{30}$]-R$_2$.

In some embodiments, R$_1$ is Ac, Tfa, or is absent;
In some embodiments, A$^1$ is Tyr, Dat, or N-Me-Tyr;
In some embodiments, A$^2$ is Ala, D-Ala, Abu, or D-Abu;
In some embodiments, A$^6$ is Phe or Fpa5;
In some embodiments, A$^8$ is Asn, Ala, Gln, Thr, or N-Me-Ala;
In some embodiments, A$^{11}$ is Arg, His, or Har;
In some embodiments, A$^{12}$ is Orn, or Lys(Me)$_2$;
In some embodiments, A$^{15}$ is Abu or Ala;
In some embodiments, A$^{20}$ is Arg, His, or Har;
In some embodiments, A$^{21}$ is Orn, or Lys(Me)$_2$;
In some embodiments, A$^{22}$ is Leu, or Orn;
In some embodiments, A$^{28}$ is Ser, or Asp;
In some embodiments, A$^{29}$ is Arg, Har, Agm, D-Arg, or D-Har;
In some embodiments, A$^{30}$ is Arg, Agm, Ada, Amc, Aha, Apa, Har, D-Arg, D-Har, Gab, Gln, D-Gln, Gln-Gab, D-Gln-Gab, or is absent;
In some embodiments, R$_2$ is —NH$_2$, —NH—CH$_3$, —NH—CH$_2$—CH$_3$, —OH, —NHR$_3$, —N(R$_3$)$_2$, or —OR$_3$, wherein R$_3$ is any of C$_{1-12}$ alkyl, C$_{2-12}$ alkenyl, or C$_{2-12}$ alkynyl, and pharmaceutically acceptable salts thereof;
In some embodiments, the agonist peptide is different from SEQ ID NO: 1 in at least one amino acid residue; and
In some embodiments, if the A$^{29}$ is Agm, then A$^{30}$ and R$_2$ are absent, and A$^1$ is N-Me-Tyr.

The nomenclature used to define the amino acid residues and synthetic peptides is according to the IUPAC-IUB Commission on Biochemical Nomenclature (European J. Biochem., 1984, 138, 9-37). The naturally occurring amino acids found in proteins are depicted by the following three letter codes: Gly, Ala, Val, Leu, Ile, Ser, Thr, Lys, Arg, Asp, Asn, Glu, Gln, Cys, Met Phe, Tyr, Pro, Trp and His.

Other abbreviations used are:
Aah alpha-amino-hexanoic acid
Aap alpha-amino-pentanoic acid
Abu alpha-aminobutyric acid
Ac acetyl
AcOH acetic acid
Ac$_2$O acetic anhydride
Ada 12-aminododecanoyl
Agm agmatine
Aha 6-aminohexanoyl
AM aminomethyl
Amc 8-Aminocaprylyl
Apa 5-Aminopentanoyl
Aib alpha-aminoisobutyroyl
Boc tert-butyloxycarbonyl
Bom benzyloxymethyl
2BrZ 2-bromo-benzyloxycarbonyl
Bu1 tertiary butyl (ester)
Bzl benzyl cHx cyclohexyl
2ClZ 2-chloro-benzyloxycarbonyl
2ClTrt 2-chlorotrityl
Cpa para-chlorophenylalanine
Dat des-amino-tyrosine
DCM dichloromethane
DIC N,N'-diisopropylcarbodiimide
DIEA diisopropylethylamine
DMF dimethylformamide
Et ethyl
Fm fluorenylmethyl
Fmoc fluorenylmethoxycarbonyl
For formyl
Fpa mono- or poly-fluorinated Phe (fluorine substitution on the aromatic ring)
Fpa5 pentafluoro-Phe
Gab gamma-amino butanoyl
GH growth hormone
GHRH GH releasing hormone
Har homoarginine
HBTU 2-(1H-Benzotriazol-1-yl)-1,1,3,3-tetramethyluronium hexafluorophosphate
hGHRH human GHRH
HOBt 1-hydroxybenzotriazole
HPLC high performance liquid chromatography
Ibu isobutyryl
MBHA para-methylbenzhydrylamine
Me methyl
MeOH methanol
MeCN acetonitrile
Mmt 4-methoxytrityl
Mtr 4-methoxy-2,3,6-trimethylbenzenesulphonyl
N-Me-Ala N-methyl-Ala
N-Me-Tyr N-methyl-Tyr
Nle norleucine
NMM N-methylmorpholine
Oaa omega-amino acid
Orn ornithine
PAM phenylacetamidomethyl
Pbf 2,2,4,6,7-pentamethyl-dihydrobenzofurane-5-sulfonyl
Ph phenyl PS polystyrene
rGHRH ratGHRH
RP-HPLC reversed phase HPLC
SPA para-sulfonyl-phenoxyacetyl
tBu tertiary butyl (ether)
TFA trifluoroacetic acid
Tfa trifluoroacetyl
Tos para-toluenesulfonyl
Trt trityl (triphenylmethyl)
Z benzyloxycarbonyl In some embodiments, the GHRH agonist peptide may be of the formula:

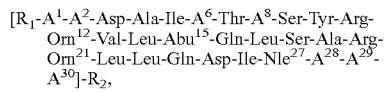

wherein $R_1$ is Ac or is absent,
$A^1$ is Tyr, Dat, or N-Me-Tyr,
$A^2$ is Ala, D-Ala, Abu, or D-Abu,
$A^6$ is Phe or Fpa5,
$A^8$ is Asn, Ala, Gln, or Thr,
$A^{28}$ is Ser, or Asp,
$A^{29}$ is Arg, Agm, or D-Arg,
$A^{30}$ is Arg, Agm, Ada, Amc, Aha, Apa, Har, D-Arg, D-Har, Gab, Gln, D-Gln, or is absent,
$R_2$ is —$NH_2$, —OH, —$NHR_3$, —$N(R_3)_2$, or —$OR_3$,
wherein $R_3$ is any of $C_{1-12}$ alkyl, $C_{2-12}$ alkenyl, or $C_{2-12}$ alkynyl,
and pharmaceutically acceptable salts thereof, and wherein the agonist peptide is different from SEQ ID NO: 1 in at least one amino acid residue.

In some embodiments, the GHRH agonist peptide may be of the formula:

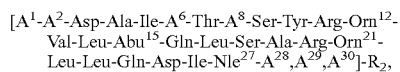

wherein $A^1$ is Dat, or N-Me-Tyr,
$A^2$ is Ala, or D-Ala,
$A^6$ is Phe or Fpa5,
$A^8$ is Asn, Gln, or Thr,
$A^{28}$ is Ser, or Asp,
$A^{29}$ is Arg, Agm, or D-Arg,
$A^{30}$ is Arg, Agm, Ada, Amc, Aha, Apa, Har, D-Arg, D-Har, Gab, Gln, D-Gln, or is absent,
$R_2$ is —$NH_2$, —OH, —$NHR_3$, —$N(R_3)_2$, or —$OR_3$,
wherein $R_3$ is any of $C_{1-12}$ alkyl, $C_{2-12}$ alkenyl, or $C_{2-12}$ alkynyl,
and pharmaceutically acceptable salts thereof.

The amino acid sequences of the synthetic peptides are numbered in correspondence with the amino acid residues in wild-type hGHRH(1-30) (SEQ ID NO: 1); thus, for example, the synthetic peptide P-20103 may be represented in an abbreviated form as below:

[N-Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29).

The residue N-Me-Tyr$^1$ represents substitution at position 1 of wild-type hGHRH(1-30)$NH_2$ (SEQ ID NO: 1) in place of Tyr; Fpa5$^6$ represents substitution position 6 in place of Phe; Gln$^8$ represents substitution at position 8 in place of Asn, and so on. Further, the amino acid residues at the positions which are not recited in the above abbreviated form (positions $A^2$, $A^3$, $A^4$, $A^5$, $A^7$, $A^9$, $A^{10}$, $A^{11}$, $A^{13}$, $A^{14}$, $A^{16}$, $A^{17}$, $A^{18}$, $A^{19}$, $A^{20}$, $A^{22}$, $A^{23}$, $A^{24}$, $A^{25}$, $A^{26}$) correspond to the amino acid residues of the wild-type hGHRH(1-30)$NH_2$ (SEQ ID NO: 1). Thus, the abbreviated form of a synthetic peptide represent different substitutions when compared to the wild-type hGHRH(1-30)$NH_2$ (SEQ ID NO: 1). Further, in some embodiments, the synthetic peptides described herein may be 30 amino acids in length, as represented by hGHRH(1-30). In some embodiments, the synthetic peptides may be 29 amino acids in length, as represented by hGHRH(1-29)$NH_2$. The convention under which the N-terminal of a peptide is placed to the left, and the C-terminal to the right is also followed herein.

Suitable synthetic hGHRH agonist peptides in abbreviated form are disclosed in Table 1.

TABLE 1

| | |
|---|---|
| P-20103 | [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH (1-29)(SEQ ID NO: 2); |
| P-20105 | [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$] hGHRH(1-29); |
| P-20107 | [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGHRH(1-29)(SEQ ID NO: 3); |
| P-20109 | [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$] hGHRH(1-29); |
| P-20110 | [N—Me-Tyr$^1$, D-Ala$^2$, Fpa5$^6$, Orn$^{12}$, Abu$^{15}$, Orn$^{21}$, Nle$^{27}$, Agm$^{29}$]hGHRH(1-29); |
| P-20111 | [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$] hGHRH(1-29); |
| P-20113 | [N—Me-Tyr$^1$, Fpa5$^6$, Orn$^{12}$, Abu$^{15}$, Orn$^{21}$, Nle$^{27}$, Asp$^{28}$, Agm$^{29}$]hGHRH(1-29) (SEQ ID NO: 4); |
| P-20115 | [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH (1-29)(SEQ ID NO: 5); |
| P-20117 | [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH (1-29) ; |
| P-20350 | [Dat$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29): |
| P-20351 | [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29); |
| P-20356 | [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) (SEQ ID NO: 6); |
| P-20357 | [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH (1-29); |
| P-20358 | [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$] hGHRH(1-29); |
| P-20359 | [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH (1-29); |
| P-20360 | [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$] hGHRH (1-29); |

TABLE 1-continued

P-20361 [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH (1-29);

P-20367 [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29);

P-20370 [N—Me-Tyr$^1$, Orn$^{12}$, Abu$^{15}$, Orn$^{21}$, Nle$^{27}$, Asp$^{28}$, Agm$^{29}$]hGHRH(1-29)(SEQ ID NO: 7);

P-20371 [N—Me-Tyr$^1$, Thr$^8$, Orn$^{12}$, Abu$^{15}$, Orn$^{21}$, Nle$^{27}$, Asp$^{28}$, Agm$^{29}$]hGHRH(1-29) (SEQ ID NO: 8);

P-20372 [N—Me-Tyr$^1$, Ala$^8$, Orn$^{12}$, Abu$^{15}$, Orn$^{21}$, Nle$^{27}$, Asp$^{28}$, Agm$^{29}$]hGHRH(1-29) (SEQ ID NO: 9);

P-20373 [N—Me-Tyr$^1$, Gln$^8$, Orn$^{12}$, Abu$^{15}$, Orn$^{21}$, Nle$^{27}$, Agm$^{29}$]hGHRH(1-29)(SEQ ID NO: 10);

P-20374 [N—Me-Tyr$^1$, Orn$^{12}$, Abu$^{15}$, Orn$^{21}$, Nle$^{27}$, Agm$^{29}$]hGHRH(1-29) (SEQ ID NO: 11);

P-20375 [N—Me-Tyr$^1$, Thr$^8$, Orn$^{12}$, Abu$^{15}$, Orn$^{21}$, Nle$^{27}$, Agm$^{29}$]hGHRH(1-29)(SEQ ID NO: 12);

P-20376 [N—Me-Tyr$^1$, Ala$^8$, Orn$^{12}$, Abu$^{15}$, Orn$^{21}$, Nle$^{27}$, Agm$^{29}$]hGHRH(1-29)(SEQ ID NO: 13);

P-21300 [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;

P-21301 [N—Me-Tyr$^1$, Orn$^{12}$, Abu$^{15}$, Orn$^{21}$, Nle$^{27}$, Asp$^{28}$, Amc$^{30}$]hGHRH(1-30)NH$_2$(SEQ ID NO: 14);

P-21303 [N—Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;

P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;

P-21305 [N—Me-Tyr$^1$, D-Ala$^2$, Gln$^8$, Orn$^{12}$, Abu$^{15}$Orn$^{21}$, Nle$^{27}$, Asp$^{28}$, Amc$^{30}$] hGHRH(1-30)NH$_2$;

P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;

P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$] hGHRH(1-30)NH$_2$;

P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$;

P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGH-RH(1-30)NH$_2$;

P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$] hGHRH(1-30)NH$_2$;

P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;

P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGHRH (1-30)NH$_2$(SEQ ID NO: 15);

P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-22327 [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 16);

P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-22329 [N—Me-Tyr$^1$, D-Ala$^2$, Orn$^{12}$, Abu$^{15}$, Orn$^{21}$, Nle$^{27}$, Apa$^{30}$]hGHRH(1-30)NH$_2$;

P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$] hGHRH(1-30)NH$_2$;

P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$] hGHRH(1-30)NH$_2$;

P-22332 [N—Me-Tyr$^1$, Orn$^{12}$, Abu$^{15}$, Orn$^{21}$, Nle$^{27}$, Asp$^{28}$, Apa$^{30}$]hGHRH(1-30)NH$_2$(SEQ ID NO: 17);

P-22334 [N—Me-Tyr$^1$, Orn$^{12}$, Abu$^{15}$, Orn$^{21}$, Nle$^{27}$, Apa$^{30}$]hGHRH(1-30)NH$_2$(SEQ ID NO: 18);

P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 19);

P-22336 [N—Me-Tyr$^1$ Ala$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 20);

P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;

P-23251 [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 21);

P-23252 [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$_2$;

P-23253 [Dat$^1$, Orn$^{12}$, Abu$^{15}$, Orn$^{21}$, Nle$^{27}$, Asp$^{28}$, Har$^{30}$]hGHRH(1-30)NH$_2$(SEQ ID NO: 22);

P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;

P-23255 [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 23);

P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;

P-23257 [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 24);

P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;

P-23259 [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 25);

P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$;

P-23261 [N—Me-Tyr$^1$, Orn$^{12}$, Abu$^{15}$, Orn$^{21}$, Nle$^{27}$, Asp$^{28}$, Har$^{30}$]hGHRH(1-30)NH$_2$(SEQ ID NO: 26);

P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;

P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 27);

P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;

P-23265 [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 28);

P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$(SEQ ID NO: 29);

P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24342 [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$(SEQ ID NO: 30);

P-24344 [Dat$^1$-D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

TABLE 1-continued

P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$;

P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;

P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;

P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;

P-25501 [N—Me-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25502 [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$;

P-25503 [N—Me-Tyr$^1$, Abu$^2$, Orn$^{12}$, Abu$^{15}$, Orn$^{21}$, Nle$^{27}$, Gab$^{30}$]hGHRH(1-30)NH$_2$(SEQ ID NO: 31);

P-25504 [Dat$^1$, D-Abu$^2$, Orn$^{12}$, Abu$^{15}$, Orn$^{21}$, Nle$^{27}$, Gab$^{30}$]hGHRH(1-30)NH$_2$;

P-25506 [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$;

P-25508 [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$;

P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$;

P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;

P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$;

P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;

P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27405 [N—Me-Tyr$^1$, Gln$^8$, Orn$^{12}$, Abu$^{15}$, Orn$^{21}$, Nle$^{27}$]hGHRH(1-29)NH—CH$_3$(SEQ ID NO: 32);

P-27406 [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$(SEQ ID NO: 33);

P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$(SEQ ID NO: 34);

P-27408 [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$;

P-27409 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;

P-27411 [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$;

P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;

P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$(SEQ ID NO: 35);

P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$;

P-27415 [N—Me-Tyr$^1$, Orn$^{12}$, Abu$^{15}$, Orn$^{21}$, Nle$^{27}$, Gab$^{30}$]hGHRH(1-30)NH—CH$_3$(SEQ ID NO: 36);

P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;

P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27419 [Ac-Tyr$^1$, Thr$^8$, Orn$^{12}$, Abu$^{15}$, Orn$^{21}$, Nle$^{27}$]hGHRH(1-29)NH—CH$_3$(SEQ ID NO: 37);

P-27422 [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$;

P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27424 [Dat$^1$, Thr$^8$, Orn$^{12}$, Abu$^{15}$, Orn$^{21}$, Nle$^{27}$]hGHRH(1-29)NH—CH$_3$(SEQ ID NO: 38);

P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$;

P-27443 [N—Me-Tyr$^1$, Orn$^{12}$, Abu$^{15}$, Orn$^{21}$, Nle$^{27}$, D-Arg$^{29}$]hGHRH(1-29)NH—CH$_3$;

P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$;

P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;

P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;

P-27449 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$;

P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;

TABLE 1-continued

P-27451 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$] hGHRH(1-30)NH—CH$_3$;

P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28421 [N—Me-Tyr$^1$, D-Ala$^2$, Orn$^{12}$, Abu$^{15}$, Orn$^{21}$, Nle$^{27}$, Asp$^{28}$]hGHRH(1-29) NH—CH$_2$—CH$_3$;

P-28430 [N—Me-Tyr$^1$, D-Ala$^2$, Gln$^8$, Orn$^{12}$, Abu$^{15}$, Orn$^{21}$, Nle$^{27}$]hGHRH(1-29) NH—CH$_2$—CH$_3$;

P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;

P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$] hGHRH(1-29)NH—CH$_2$—CH$_3$;

P-28461 [N—Me-Tyr$^1$, D-Ala$^2$, Gln$^8$, Orn$^{12}$, Abu$^{15}$, Orn$^{21}$, Nle$^{27}$]hGHRH(1-29) NH—CH$_2$—CH$_3$;

P-28462 [N—Me-Tyr$^1$, D-Ala$^2$, Fpa5$^6$, Orn$^{12}$, Abu$^{15}$, Orn$^{21}$, Nle$^{27}$]hGHRH(1-29) NH—CH$_2$—CH$_3$;

P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;

P-28464 [N—Me-Tyr$^1$, D-Ala$^2$, Fpa5$^6$, Gln$^8$, Orn$^{12}$, Abu$^{15}$, Orn$^{21}$, Nle$^{27}$]hGHRH (1-29)NH—CH$_2$—CH$_3$;

P-28465 [N—Me-Tyr$^1$, D-Ala$^2$, Gln$^8$, Orn$^{12}$, Abu$^{15}$, Orn$^{21}$, Nle$^{27}$, Asp$^{28}$] hGHRH(1-29)NH—CH$_2$—CH$_3$;

P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH (1-29)NH—CH$_2$—CH$_3$;

P-28467 [N—Me-Tyr$^1$, D-Ala$^2$, Orn$^{12}$, Abu$^{15}$, Orn$^{21}$, Nle$^{27}$, Asp$^{28}$]hGHRH(1-29) NH—CH$_2$—CH$_3$;

P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$] hGHRH(1-29)NH—CH$_2$—CH$_3$;

P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;

P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$] hGHRH(1-29)NH—CH$_2$—CH$_3$;

P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;

P-28474 [Dat$^1$, D-Ala$^2$, Orn$^{12}$, Abu$^{15}$, Orn$^{21}$, Nle$^{27}$, Asp$^{28}$] hGHRH(1-29)NH—CH$_2$—CH$_3$;

P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;

P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;

P-28477 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$;

P-28478 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$;

P-28479 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$] hGHRH(1-30)NH—CH$_2$—CH$_3$;

P-29701 [N—Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$] hGHRH](1-30)NH$_2$;

P-29702 [Dat$^1$, D-Ala$^2$, Orn$^{12}$, Abu$^{15}$, Orn$^{21}$, Nle$^{27}$, Gln-Gab$^{30}$]hGHRH(1-30)NH$_2$;

P-29703 [N—Me-Tyr$^1$, Gln$^8$, Orn$^{12}$, Abu$^{15}$, Orn$^{21}$, Nle$^{27}$, Gln-Gab$^{30}$]hGHRH(1-30)NH$_2$(SEQ ID NO: 39);

P-29704 [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$;

P-29706 [Tfa-Tyr$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$;

P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$;

P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$;

P-29720 [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$;

P-29721 [Dat$^1$, D-Ala$^2$, Gln$^8$, Orn$^{12}$, Abu$^{15}$, Orn$^{21,22}$, Nle$^{27}$, Asp$^{28}$, Gln-Gab$^{30}$]hGHRH(1-30) NH$_2$;

P-29722 [Tfa-Tyr$^1$, D-Abu$^2$, Gln$^8$, Orn$^{12}$, Abu$^{15}$, Orn$^{21}$, Nle$^{27}$, Asp$^{28}$, Gln$^{30}$, Gab$^{31}$]hGHRH(1-30)NH$_2$;

P-29723 [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$] hGHRH (1-30)NH$_2$; and P-29724 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln Gab$^{30}$] hGHRH(1-30)NH$_2$.

Overview of Synthesis

The peptides are synthesized by suitable methods such as by exclusive solid phase techniques, by partial solid-phase techniques, by fragment condensation or by classical solution phase synthesis. For example, the techniques of exclusive solid-phase synthesis are set forth in the textbook "Solid Phase Peptide Synthesis", J. M. Stewart and J. D. Young, Pierce Chem. Company, Rockford, Ill., 1984 (2nd. ed.), and M. Bodanszky, "Principles of Peptide Synthesis", Springer Verlag, 1984. The hGHRH agonist peptides are preferably prepared using solid phase synthesis, such as that generally described by Merrifield, J. Am. Chem. Soc, 85 p. 2149 (1963), although other equivalent chemical syntheses known in the art can also be used as previously mentioned.

The synthesis is carried out with amino acids that are protected at their alpha amino group. Urethane type protecting groups (Boc or Fmoc) are preferably used for the protection of the alpha amino group. In certain cases, protected omega-amino acids are also used during the synthesis. Boc or Fmoc protecting groups are also appropriate for the protection of omega-amino groups.

In solid phase synthesis, the N-alpha-protected or N-omega-protected amino acid moiety which forms the aminoacyl group of the final peptide at the C-terminus is attached to a polymeric resin support via a chemical link. After completion of the coupling reaction, the alpha (or omega) amino protecting group is selectively removed to allow subsequent coupling reactions to take place at the amino-terminus, preferably with 50% TFA in DCM when the N-alpha-(N-omega-) protecting group is Boc, or by 20% piperidine in DMF when the N-alpha-(N-omega-) protecting group is Fmoc. The remaining amino acids with similarly Boc or Fmoc-protected alpha (or omega) amino groups are coupled stepwise to the free amino group of the preceding amino acid on the resin to obtain the desired peptide sequence. Because the amino acid residues are coupled to the alpha (or omega) amino group of the C-terminus residue, growth of the synthetic hGHRH analogue peptides begins at the C terminus and progress towards the N-terminus. When the desired sequence has been obtained, the peptide is acylated, or the amino group is left free at the N-terminus, and the peptide is removed from the support polymer.

Each protected amino acid is used in excess (2.5 or 3 equivalents) and the coupling reactions are usually carried out in DCM, DMF or mixtures thereof. The extent of completion of the coupling reaction is monitored at each stage by the ninhydrin reaction. In cases where incomplete coupling is determined, the coupling procedure is repeated, or a capping by acetylation of unreacted amino groups is carried out, before removal of the alpha (or omega) amino protecting group prior to the coupling of the next amino acid.

Typical synthesis cycles are shown in Table 2 and Table 3.

TABLE 2

PROTOCOL FOR A TYPICAL SYNTHETIC CYCLE USING BOC-STRATEGY

| Step | Reagent | Mixing Time (min) |
|---|---|---|
| 1. Deprotection | 50% TFA in DCM | 5 + 25 |
| | DCM wash | 1 |
| | 2-propanol wash | 1 |
| 2. Neutralization | 5% DIEA in DCM | 1 |
| | DCM wash | 1 |
| | MeOH wash | 1 |
| | 5% DIEA in DCM | 3 |
| | MeOH wash | 1 |
| | DCM wash (3 times) | 1 |
| 3. Coupling | 3 eq. Boc-amino acid in DCM or DMF + 3 eq. DIC or the preformed HOBt ester of the Boc-amino acid | 60 |
| | MeOH wash (3 times) | 1 |
| | DCM wash (3 times) | 1 |
| 4. Acetylation (if appropriate) | $Ac_2O$ in pyridine (30%) | 10 + 20 |
| | MeOH wash (3 times) | 1 |
| | DCM wash (3 times) | 1 |

TABLE 3

PROTOCOL FOR A TYPICAL SYNTHETIC CYCLE USING FMOC-STRATEGY

| Step | Reagent | Time |
|---|---|---|
| 1. Deprotection | 20% piperidine in DMF | 5 + 15 |
| | DMF wash (3 times) | 1 |
| 2. Coupling | 3 eq. Fmoc-amino acid in DMF 3 eq. DIC or + 3 eq. HBTU + 3 eq. HOBt + 6 eq. DIEA | 60 |
| | DMF wash (3 times) | 1 |
| 3. Acetylation (if appropriate) | 3 eq. 1-acetyl imidazole in DMF | 30 |
| | DMF wash (3 times) | 1 |

After completion of the synthesis, the cleavage of the peptide from the resin can be effected using procedures well known in peptide chemistry.

Choice of Support Polymer

The hGHRH agonist peptides may be synthesized on a variety of support polymers, i.e. MBHA, Merrifield, PAM, Rink amide or Wang resins. The peptides can also be synthesized on aminomethyl, MBHA, or other resins that have been previously derivatized with suitable linkers. Examples of such linkers are the base-labile 4-hydroxymethyl benzoic acid (HMBA) linker for the attachment of C-terminal carboxyl groups, the acid-labile para-sulfonyl-phenoxyacetyl (SPA) linker which permits the attachment of agmatine through its guanidino group, or the acid-labile [3-[(Methyl-Fmoc-amino)methyl]-indol-1-yl]-acetyl linker which allows the synthesis of peptides with C-terminal methylamide (—NH—CH3).

When peptides with an amidated C-terminus are synthesized by using Boc strategy, the preferred resin is MBHA. Attachment of the C-terminal amino acid to this resin can be accomplished by the standard DIC-mediated coupling method described in Table 2.

In order to prepare peptides with C-terminal methylamide (—NH—$CH_3$) or ethylamide (—NH—$CH_2$—$CH_3$) modification, two methods can be used: a) the Merrifield resin is loaded with the Boc-protected C-terminal amino acid by coupling mediated by potassium fluoride (KF) or cesium salt at elevated temperature; b) [3-[(Methyl-Fmoc-amino)methyl]-indol-1-yl]-acetylAm or 3-[(Ethyl-Fmoc-amino)methyl]-indol-1-yl]-acetyl Am resins may be used, respectively for the synthesis of peptides having C-terminal methylamide (—NH—$CH_3$) or ethylamide (—NH—$CH_2$—$CH_3$) modification. When using these resins, the Fmoc protecting group can be removed from the resin with the methods described in Table 3 before the synthesis.

For the synthesis of peptides having Agm at the C-terminus, two methods may be used. In one embodiment, the support phase is MBHA resin or an aminomethyl resin, and the guanidino group of Boc-Agm is joined to the support polymer through a stable, but readily cleavable linker such as the para-sulfonyl-phenoxyacetyl (SPA) moiety. The alpha-amino-Boc-protected Agm is reacted with the chlorosulfonyl phenoxyacetic acid Cl—$SO_2$—$C_6H_4$—O—$CH_2$—COOH to form Boc-Agm-$SO_2$—$C_6H_4$—O—$CH_2$—COOH. This compound is then coupled to the support polymer e.g. to MBHA resin using DIC or HBTU-HOBt-DIEA as activating reagent to yield Boc-Agm-SPA-MBHA. In another embodiment, Agm-$SO_2$-PS resin may be used for the synthesis (1% DVB, 100-200 mesh, 2.5 mmol/g, Advanced ChemTech (Louisville, Ky.)) at pH 10-13 to form Boc-Agm-$SO_2$-resin.

Amino Acid Derivatives Used

Bifunctional amino acids, i.e. those not having side chain functional groups, are mostly used in the form of their N-alpha Boc- or Fmoc-derivatives for synthesis. Bifunctional omega-amino acids are also typically used in the form of their N-omega Boc- or Fmoc-derivatives. Thus, Boc-Gly-OH or Fmoc-Gly-OH is typically used for incorporating the Gly residue. The naturally occurring bifunctional amino acids are Gly, Ala, Val, Leu, Ile, Phe, and Pro, and some well-known non-coded bifunctional amino acids used in this invention are Abu, Aib, Gab, Nle, Aah, and Aap.

Some of the amino acid residues of the peptides have side chain functional groups which are reactive with reagents used in coupling or deprotection. When such side chain groups are present, suitable protecting groups are joined to these functional groups to prevent undesirable chemical reactions occurring during the coupling reactions.

The following general rules may be followed in selecting a particular side chain protecting group: (a) the protecting group preferably retains its protecting properties and is not split off under coupling conditions, (b) the protecting group should be stable under conditions for removing the alpha amino protecting group at each step of the synthesis, (c) the side chain protecting group must be removable upon the completion of the synthesis of the desired amino acid sequence, under reaction conditions that will not undesirably alter the peptide chain.

When Boc-amino acids are used in the synthesis, the reactive side chain functional groups can be protected as follows: Tos or nitro ($NO_2$) for Arg and Har; cHx or Fm for Asp and Glu; Bom for His; 2ClZ or Fmoc for Lys and Orn; Bzl for Ser and Thr; and 2BrZ for Tyr. The side chains of Asn and Gln are unprotected.

In the case of Fmoc synthesis, the reactive side chain functional groups can be protected by other appropriate protective groups as follows: 2,2,4,6,7-pentamethyl-dihydrobenzofurane-5-sulfonyl (Pbf), 4-methoxy-2,3,6-trimethyl benzenesulphonyl (Mtr), or bis-Boc for Arg and Har; tert-butyl (Bu1) for Asp and Glu; no protective group or trityl (Trt) protection for Asn and Gln; Trt for His; Boc or 4-methoxytrityl (Mmt) for Lys and Orn; tBu or Trt for Ser and Thr; and tBu or 2-chlorotrityl (2ClTrt) for Tyr. In addition to the widely known coded and non-coded amino acids mentioned above, some of the peptides of this application contain less common non-coded amino acids such as homoarginine (Har); ornithine (Orn); N-methyl-alanine [N-Me-Ala]; N-methyl-tyrosine [N-Me-Tyr]; pentafluoro-phenylalanine [Phe(F)5, Fpa5]. These amino acid residues are incorporated into the peptides by coupling the suitable protected amino acid derivatives. A non-exclusive list of such protected amino acid derivatives that can be used is as follows: Boc-Har(Tos)-OH, Boc-Orn(2ClZ)-OH, Boc-N-Me-Ala-OH, Boc-N-Me-Tyr (2BrZ)-OH, Boc-Fpa5-OH, Fmoc-Har(Pbf)-OH, Fmoc-Orn (Boc)-OH, Fmoc-N-Me-Ala-OH, and Fmoc-N-Me-Tyr (2ClTrt)-OH. The protected derivatives of noncoded amino acids mentioned above are commonly available from several commercial suppliers, including Novabiochem (San Diego, Calif.), Advanced ChemTech (Louisville, Ky.), Bachem (King of Prussia, Pa.), Peptides International (Louisville, Ky.), RSP Amino Acid Analogues DBA (Worcester, Mass.), and AnaSpec (San Jose, Calif.).

Stepwise Coupling of Amino Acid Residues

Utilizing the above mentioned support polymers and after loading of the protected C-terminal amino acid or Agm residue, the peptide itself may suitably be built up by solid phase synthesis in the conventional manner. Each protected amino acid is coupled in about a three-fold molar excess, with respect to resin-bound free amino residues, and the coupling may be carried out in a medium such as DMF-DCM (1:1) or in DMF or DCM alone. The selection of an appropriate coupling reagent is within the skill of the art. Particularly suitable as coupling reagents are N,N'-diisopropyl carbodiimide (DIC), or HBTU combined with HOBt in the presence of DIEA. The success of the coupling reaction at each stage of the synthesis is preferably monitored by the ninhydrin reaction. In cases where incomplete coupling occurs, either the coupling procedure is repeated, or the resin-bound unreacted amino residues are acetylated using a capping reagent, before removal of the alpha (or omega) amino protecting group. Suitable capping reagents are 1-acetylimidazole and $Ac_2O$ in pyridine.

Cleavage of the Peptide from the Support Polymer and Removal of the Side-Chain Protecting Groups When the synthesis is complete, the peptide is cleaved from the support phase and its side-chain protecting groups are removed.

In cases where peptides with an amidated C-terminus (—$CONH_2$) or with a C-terminal carboxyl group (—COOH) are prepared by Boc strategy on an MBHA, Merrifield, or PAM resin, the removal of the peptide from the resin is performed by treatment with a reagent such as liquid hydrogen fluoride (HF). This is also the case for peptides synthesized on the Boc-Agm-SPA-MBHA or Bos-Agm-tosyl-resin. In some instances, the liquid HF also cleaves all the remaining side chain protecting groups. However, if side chain protecting groups resistant to HF treatment are present on the peptide, additional cleavage steps should be performed in order to remove these protecting groups. Thus, Fm and Fmoc protecting groups are removed by treatment with 20% piperidine in DMF, prior to or after the HF treatment.

Suitably, the dried and protected peptide-resin is treated with a mixture consisting of 1.0 mL m-cresol and 10 mL anhydrous hydrogen fluoride per gram of peptide-resin for 60-120 min at 0° C. to cleave the peptide from the resin as well as to remove the HF-labile side chain protecting groups. After the removal of the hydrogen fluoride under a stream of nitrogen and vacuum, the free peptides are precipitated with ether, filtered, washed with ether and ethyl acetate, extracted with 50% acetic acid, and lyophilized.

In cases where peptides with a methyl-(—NH—CH3), or ethyl-amide (—NH—$CH_2$—$CH_3$) C-terminus are prepared by Boc strategy on the Merrifield or HMBA-MBHA resin, the protected peptides are first cleaved from the resin by methylamine ($CH_3NH_2$) or ethylamine ($CH_3CH_2NH_2$ mediated aminolysis. Suitably, liquid $CH_3NH_2$ or $CH_3CH_2NH_2$ is transferred into a cooled, heavy-walled glass flask that contains the dried and protected peptide-resin. The quantity of liquid $CH_3NH_2$ or $CH_3CH_2NH_2$ should be sufficient to cover the peptide-resin. The flask is stoppered, and shaken with the liquid $CH_3NH_2$ or $CH_3CH_2NH_2$ for 3.5 hours at room temperature in order to allow for the reaction to take place. After this, the flask is cooled in a dry ice bath, opened, and the liquid $CH_3NH_2$ or $CH_3CH_2NH_2$ is filtered off the solid residue that contains a mixture of resin and cleaved peptide, the peptide still having the protecting groups attached. The solid residue is dried and subjected to HF treatment as described above, in order to remove the side chain protecting groups of the peptide.

In cases when peptides with a methyl-(—NH—$CH_3$), or ethyl-amide (—NH—$CH_2$—$CH_3$) C-terminus are prepared by Fmoc strategy on [3-[(Methyl-Fmoc-amino)methyl]-30 indol-1-yl]-acetyl AM or 3-[(Ethyl-Fmoc-amino)methyl]-indol-1-yl]-acetyl AM resins, respectively, the protected peptides are cleaved from the resin with a cleavage cocktail. Since no single cleavage and deprotection procedure is optimal for all peptides due to the nature of the linker and the amino acid composition of the peptide, the following cleavage cocktail proved to be the most suitable for cleavage and deprotection of GHRH agonists: 94% TFA, 3% $H_2O$, 1.5% m-cresol, and 1.5% phenol. Cleavage cocktail must be prepared fresh and have to use high quality TFA and scavengers. The amount of cleavage cocktail used depends on both the amount of the peptide-resin and its properties. Enough cocktail solution should be used to 5 saturate and swell the resin during the reaction, with about 2-3 mm of clear solution below the floating beads. Generally 5 mL of cleavage cocktail is used for 0.5 g of resin. The choice of reaction time depends on the linker and the side-chain protecting groups of the peptide. Preferably, 3-hour reaction time is used for the cleavage and deprotection of GHRH agonists. To induce peptide precipitation, the cleavage mixture is added dropwise to cold (preferably −20° C.) ether. The non-peptide products remain in the ether solution. The precipitated material is collected by filtration or centrifugation and is washed three times with cold ether to remove any residual scavengers. The cleaved and deprotected peptide is dissolved in 50% acetic acid and separated from the resin by filtration and, after dilution with water, the solution is lyophilized.

Purification

The purification of the crude peptides can be effected using procedures well known in peptide chemistry. For example, purification may be performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0 using an XBridge Prep OBD™ reversed phase column (4.6×250 mm, packed with $C_{18}$ silica gel, 300 A pore size, 5 μm particle size) (Waters Co., Milford, Mass.). The column is eluted with a solvent system consisting of (A) 0.1% aqueous TFA and (B) 0.1% TFA in 70% aqueous MeCN in a linear gradient mode (e.g., 30-55% B in 120 min); flow rate of 12 mL/min. The eluent is monitored at 220 nm, and fractions are examined by analytical HPLC using a Hewlett-Packard Model HP-1090 liquid chromatograph and pooled to give maximum purity. Analytical HPLC is carried out on a Supelco Discovery HS C18 reversed-phase column (2.1×50 mm, C18, 300 A pore size, 3 μm particle size) (Supelco, Bellefonte, Pa.) using isocratic elution with a solvent system consisting of (A) and (B) defined above with a flow rate of 0.2 mL/min. The peaks are monitored at 220 and 280 nm. The peptides are judged to be substantially (>95%) pure by analytical HPLC. Molecular masses are checked by electrospray mass spectrometry (Agilent Technologies 6210 Time-of-Light LC/MS, Santa Clara, Calif.) and the expected amino acid compositions are confirmed by amino acid analysis.

The peptides of the invention may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly 10 preferred agonists are salts of low solubility, e.g., pamoate salts and the like. These exhibit long duration of activity.

Formulations containing the peptides of the present invention and a suitable carrier can be solid dosage forms which include, but are not limited to, softgels, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. In some embodiments, a single dose may comprise one or more softgels, tablets, capsules, cachets, pellets, pills, or the like. Specific examples include, for example, a dose comprising 1, 2, 3, or 4 softgels, tablets, capsules, cachets, pellets, pills or the like.

In some embodiments, one or more softgels, tablets, capsules, cachets, pellets, pills, or the like can be taken to achieve the desired dosing. In some embodiments, one or more softgels, tablets, capsules, pellets, pills, or the like can be taken simultaneously to achieve the desired dosing. In yet another embodiment one or more softgels, tablets, capsules, cachets, pellets, pills, or the like can be taken separately during the course of a specified time period such as for example, a 24 hour period. For example, one or more softgels, tablets, capsules, cachets, pellets, pills, or the like can be taken twice in a 24 hour period to achieve the desired dose. In some embodiments, one or more softgels, tablets, capsules, cachets, pellets, pills, or the like can be taken with a meal. For example one or more softgels, tablets, capsules, cachets, pellets, pills, or the like can be taken with each meal during the course of a 24 hour period to achieve the desired dose.

It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics,* 6th Edition, MacMillan Publishing Co., New York (1980) can be consulted.

In some embodiments, the pharmaceutical excipient may include, without limitation, binders, coating, disintegrants, fillers, diluents, flavors, colors, lubricants, glidants, preservatives, sorbents, sweeteners, conjugated linoleic acid (CLA), gelatin, beeswax, purified water, glycerol, any type of oil, including, without limitation, fish oil or soybean oil, or the like. Pharmaceutical compositions of the peptides/compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The peptides/compounds of the present invention can be administered in the conventional manner by any route where they are active. Administration can be systemic, parenteral, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the peptides/compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Alternatively, the peptides may be administered as an intranasal spray with an appropriate carrier or by pulmonary inhalation. One suitable route of administration is a depot form formulated from a biodegradable suitable polymer, e.g., poly-D,L-lactide-coglycolide as microcapsules, microgranules or cylindrical implants containing dispersed agonist compounds.

Specific modes of administration will depend on the indication. The selection of the specific route of administration and the dose regimen is to be adjusted or titrated by the clinician according to methods known to the clinician in order to obtain the optimal clinical response. The amount of peptides/compounds to be administered is that amount which is therapeutically effective. The dosage to be administered will depend on the characteristics of the subject being treated, e.g., the particular animal or human being treated, age, weight, health, types of concurrent treatment, if any, and frequency of treatments, and can be easily determined by one of skill in the art (e.g., by the clinician).

The amount of peptide needed depends on the type of pharmaceutical composition and on the mode of administration. In cases where human subjects receive solutions of GHRH agonists, administered by i.m. or s.c. injection, or in the form of intranasal spray or pulmonary inhalation, the typical doses are between 2-20 mg/day/patient, given once a day or divided into 2-4 administrations/day. When the GHRH agonists are administered intravenously to human patients, typical doses are in the range of 8-80 µg/kg of body weight/day, divided into 1-4 bolus injections/day or given as a continuous infusion. When depot preparations of the GHRH agonists are used, e.g. by i.m. injection of pamoate salts or other salts of low solubility, or by i.m. 10 or s.c. administration of microcapsules, microgranules, or implants containing the agonist compounds dispersed in a biodegradable polymer, the typical doses are between 1-10 mg agonist/day/patient.

The peptides/compounds of the present invention can be formulated for parenteral administration by injection, e.g., by bolus injection or continuous infusion. The peptides/compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the peptides/compounds can be formulated readily by combining these peptides/compounds with pharmaceutically acceptable carriers well known in the art. Such carriers enable the peptides/compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active peptides/compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active peptides/compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the peptides/compound and a suitable powder base such as lactose or starch.

The compositions of the present invention can also be formulated in rectal compositions such as suppositories or retention enemas, e.g., containing conventional suppository bases such as cocoa butter or other glycerides.

In addition to the formulations described previously, the compositions of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the peptides/compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present invention, for example, can be applied to a plaster, or can be applied by transdermal, therapeutic systems that are consequently supplied to the organism.

The compositions of the present invention can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

This invention and embodiments illustrating the method and materials used may be further understood by reference to the following non-limiting examples. The present invention is described in connection with the following examples which are set forth for the purposes of illustration only. In the examples, optically active protected amino acids in the L-configuration are used except where specifically noted. The following Examples set forth suitable methods of synthesizing the novel GHRH agonists by the solid-phase technique.

EXAMPLES

Example 1

Synthesis of N-Me-Tyr$^1$-Ala$^2$-Asp$^3$-Ala$^4$-Ile$^5$-Fpa5$^6$-Thr$^7$-Gln$^8$-Ser$^9$-Tyr$^{10}$-Arg$^{11}$-Orn$^{12}$-Var$^3$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Lue$^{23}$-Gln$^{24}$-Asp$^{25}$-Ile$^{26}$-Nle$^{27}$-Asp$^{28}$-Agm$^{29}$ or [N-Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29) (Peptide 20103)

The synthesis is conducted in a stepwise manner using manual solid phase peptide synthesis equipment. Two methods have been used for the synthesis of peptides having Agm at the C-terminus. In one case, the starting material of the synthesis is Boc-agmatine-NG-sulfonyl-phenoxyacetyl-MBHA (Boc-Agm-SPA-MBHA) resin with a substitution of 0.3 mmol/g, which was obtained commercially from California Peptide Research, Inc. (Napa, Calif.). The synthesis of this resin is well known in the art. Briefly, Boc-Agm-SPA-MBHA resin (1.67 g, 0.50 mmol) is pre-swollen in DCM and then the deprotection and neutralization protocols described in Table 2 are performed in order to remove the Boc protecting group and prepare the peptide-resin for coupling of the next amino acid. In another case, Agm-sulfonyl-polystyrene (PS) resin is used [1% DVB, 100-200 mesh, 0.74 mmol/g, American Peptide Company (Sunnyvale, Calif.)]. Briefly, Agm-sulfonyl-PS resin (680 mg, 0.50 mmol) is neutralized with 5% DIEA in DCM and washed according to the protocol described in Table 2. The solution of Boc-Asp(OcHx)-OH (475 mg, 1.5 mmol) in DMF-DCM (1:1) is shaken with the neutralized resin and DIC (235 µl, 1.5 mmol) in a manual solid phase peptide synthesis apparatus for 1 hour. Then, the deprotection and neutralization protocols described in Table 2 are performed in order to remove the Boc protecting group and prepare the peptide-resin for coupling of the next amino acid. The synthesis is continued in a stepwise manner using manual solid phase peptide synthesis equipment in both cases, and the peptide chain is built stepwise by coupling the following protected amino acids in the indicated order on the resin to obtain the desired peptide sequence: Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn (2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

These protected amino acid residues (also commonly available from NovaBiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 ul, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 68 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 A pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 68 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 18 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 20105, Peptide 20107, Peptide 20109, Peptide 20110, Peptide 20111, Peptide 20113, Peptide 20115, Peptide 20350, Peptide 20351, Peptide 20356, Peptide 20357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376, are synthesized in the same manner as Peptide 20103, except that these peptides also contain other amino acid substitutions in the peptide sequence, and acyl moieties at their N-termini. The details for these syntheses are set forth below.

For the synthesis of Peptide 20105, the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20107, the chemical structure of which is [[N-Me-Tyr1, Fpa5$^6$, Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20109, the chemical structure of which is [N-Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20110, the chemical structure of which is [N-Me-Tyr$^1$, D-Ala$^2$, Fpa5$^6$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20111, the chemical structure of which is [N-Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20113, the chemical structure of which is [N-Me-Tyr$^1$, Fpa5$^6$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20115, the chemical structure of which is [N-Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH(1-29) the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Fpa5-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20117 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20350 the chemical structure of which [Dat$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20351 the chemical structure of which [Ac-N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Fpa5-OH, Boc-Ile-OH, Boc-Ala-OH, Boc-Asp(OcHx)-OH, Boc-D-Ala-OH, Ac-N-Me-Tyr(2BrZ)-OH.

For the synthesis of Peptide 20356, the chemical structure of which [N-Me-Tyr$^1$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln- OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20357 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 20358 the chemical structure of which [Dat$^1$, D-Ala$^2$, N-Me-Ala$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-N-Me-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20359, the chemical structure of which is [N-Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20360, the chemical structure of which is [N-Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20361, the chemical structure of which is [N-Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20367, the chemical structure of which is [N-Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20370, the chemical structure of which is [N-Me-Tyr$^1$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20371, the chemical structure of which is [N-Me-Tyr$^1$, Thr$^8$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20372, the chemical structure of which is [N-Me-Tyr$^1$, Orn$^{12}$, Abu$^{15}$, Orn$^{21}$, Nle$^{27}$, Asp$^{28}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20373, the chemical structure of which is [N-Me-Tyr$^1$, Gln$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln- OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 20374, the chemical structure of which is [N-Me-Tyr$^1$, Orn$^{12}$, Abu$^{15}$, Orn$^{21}$, Nle$^{27}$, Agm$^{29}$] hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20375, the chemical structure of which is [N-Me-Tyr$^1$, Thr$^8$, Orn$^{12}$, Abu$^{15}$, Orn$^{21}$, Nle$^{27}$, Agm$^{29}$]hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 20376, the chemical structure of which is [N-Me-Tyr$^1$, Orn$^{12}$, Abu$^{15}$, Orn$^{21}$, Nle$^{27}$, Agm$^{29}$] hGHRH(1-29), the following protected amino acids are coupled in the indicated order on the Agm-SO$_2$-PS resin: Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

HF cleavage and deprotection, and subsequent purification by semipreparative HPLC of Peptide 20105, Peptide 20107, Peptide 20109, Peptide 20110, Peptide 20111, Peptide 20113, Peptide 20115, Peptide 20350, Peptide 20351, Peptide 20356, Peptide 357, Peptide 20358, Peptide 20359, Peptide 20360, Peptide 20361, Peptide 20363, Peptide 20367, Peptide 20370, Peptide 20371, Peptide 20372, Peptide 20373, Peptide 20374, Peptide 20375, Peptide 20376 are done as described in the case of Peptide 20103. The purified compounds are judged to be substantially (>95%) pure by analytical HPLC. Their molecular masses are checked by electrospray mass spectrometry, and the expected amino acid compositions are confirmed by amino acid analysis.

Example 2

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-Amc$^{30}$-NH$_2$ (Peptide 21300) [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$. The synthesis is conducted in a stepwise manner using manual solid phase peptide synthesis equipment. Briefly, para-methylbenzhydrylamine (MBHA) resin (100-200 mesh, 1% DVB, 0.7 mmol/g, Advanced Chemtech, Louisville, Ky.) (350 mg, 0.50 mmol) is neutralized with 5% DIEA in DCM and washed according to the protocol described in Table 2. The solution of Boc-Amc-OH (390 mg, 1.5 mmol) in DMF-DCM (1:1) is shaken with the neutralized MBHA resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH. These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free. The protected amino acids (1.5 mmol each) are coupled with DIC (235 µL, 1.5 mmol) with the exceptions of Boc-Asn-OH and Boc-Gln-OH which are coupled with their preformed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 130 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C$_{18}$ silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 130 mg of crude peptide is dissolved in AcOH/H$_2$O, stirred, filtered and applied on an XBridge Prep OBD™ reversed phase column (4.6×250 mm, packed with C$_{18}$ silica gel, 300 Å pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 28 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 21301, Peptide 21303, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680, are synthesized in the same manner as Peptide 20300, except that these peptides also contain other amino acid substitutions in the peptide sequence, and/or different alpha- or omega-amino acid moieties at their C-termini. The details for these syntheses are set forth below.

For the synthesis of Peptide 21301, the chemical structure of which [N-Me-Tyr$^1$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 21303, the chemical structure of which [N-Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21304, the chemical structure of which [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21305, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21306, the chemical structure of which [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21307, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21308, the chemical structure of which [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21309, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 21310, the chemical structure of which [Dat$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 21311, the chemical structure of which [N-Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$, the following protected amino acids are coupled in the indicated order on the MBHA resin: Boc-Amc-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22325, the chemical structure of which [N-Me-Tyr$^1$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22326, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22327, the chemical structure of which [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 22328, the chemical structure of which [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Ac-Tyr(2BrZ)-OH.

For the synthesis of Peptide 22329, the chemical structure of which [N-Me-Tyr$^1$, D-Ala$^2$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22330, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22331, the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 22332, the chemical structure of which [N-Me-Tyr$^1$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22334, the chemical structure of which [N-Me-Tyr$^1$, Orn$^{12}$, Abu$^{15}$, Orn$^{21}$, Nle$^{27}$, Apa$^{30}$] hGHRH(1-30)NH$_2$, the following protected amino acids are coupled in the indicated order on the MBHA resin: Boc-Apa-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22335 the chemical structure of which [N-Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22336 the chemical structure of which [N-Me-Tyr$^1$, Ala$^8$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 22337 the chemical structure of which [N-Me-Tyr$^1$, D-Ala$^2$, Cpa$^6$, Orn$^{12}$, Abu$^{15}$, Orn$^{21}$, Nle$^{27}$, Asp$^{28}$, Apa$^{30}$]hGHRH(1-30)NH$_2$, the following protected amino acids are coupled in the indicated order on the MBHA resin: Boc-Apa-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Cpa-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23250, the chemical structure of which [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23251, the chemical structure of which [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23252, the chemical structure of which [Dat$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23253, the chemical structure of which [Dat$^1$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23254, the chemical structure of which [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23255, the chemical structure of which [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23256, the chemical structure of which [Dat$^1$, D-Ala$^2$, Ala$^8$, Orn$^{12}$, Abu$^{15}$, Orn$^{21}$, Nle$^{27}$, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp (OcHx)-OH, Boc-Nle-OH, Boc-Ile-OH, Boc-Asp(OcHx)-OH, Boc-Gln-OH, Boc-Leu-OH, Boc-Leu-OH, Boc-Orn (2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 23257, the chemical structure of which [Dat¹, Ala⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 23258, the chemical structure of which [N-Me-Tyr¹, D-Ala², Gln⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23259, the chemical structure of which [N-Me-Tyr¹, Gln⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23260, the chemical structure of which [N-Me-Tyr¹, D-Ala², Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23261, the chemical structure of which [N-Me-Tyr¹, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23262, the chemical structure of which [N-Me-Tyr¹, D-Ala², Thr⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23263, the chemical structure of which [N-Me-Tyr¹, Thr⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 23264, the chemical structure of which [N-Me-Tyr¹, D-Ala², Ala⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 23265, the chemical structure of which [N-Me-Tyr¹, Ala⁸, Orn¹², Abu¹⁵, Orn²¹, Nle²⁷, Asp²⁸, Har³⁰]hGHRH(1-30)NH₂, the following protected amino acids are coupled in the indicated order on the MBHA resin: Boc-Har(Tos)-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 24340 the chemical structure of which [N-Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(2BrZ)-OH.

For the synthesis of Peptide 24341 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24342 the chemical structure of which [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Dat-OH.

For the synthesis of Peptide 24344 the chemical structure of which [Dat$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 24345 the chemical structure of which [N-Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24346 the chemical structure of which [N-Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$, the following protected amino acids are coupled in the indicated order on the MBHA resin: Boc-Aha-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24347 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 24348 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$, the following protected amino acids are coupled in the indicated order on the MBHA resin: Boc-Aha-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25501 the chemical structure of which [N-Me-Tyr$^1$, D-Ala$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25502 the chemical structure of which [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Dat-OH.

For the synthesis of Peptide 25503 the chemical structure of which [N-Me-Tyr$^1$, Abu$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-Abu-OH, Boc-N-Me-Tyr(2BrZ)-OH.

For the synthesis of Peptide 25504 the chemical structure of which [Dat$^1$, D-Abu$^2$, Orn$^{12}$, Abu$^{15}$, Orn$^{21}$, Nle$^{27}$, Gab$^{30}$] hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Dat-OH.

For the synthesis of Peptide 25506 the chemical structure of which [N-Me-Tyr$^1$, D-Abu$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Abu-OH, Boc-N-Me-Tyr(2BrZ)-OH.

For the synthesis of Peptide 25508 the chemical structure of which [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$, the following protected amino acids are coupled in the indicated order on the MBHA resin: Boc-Gab-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 25516 the chemical structure of which [N-Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$, the following protected amino acids are coupled in the indicated order on the MBHA resin: Boc-Gab-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 26802 the chemical structure of which [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Thr(Bzl)-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 26803 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-His(Bom)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-His(Bom)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 26804 the chemical structure of which [N-Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$, the following protected amino acids are coupled in the indicated order on the MBHA resin: Boc-Ada-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(2BrZ)-OH.

HF cleavage and deprotection, and subsequent purification by semipreparative HPLC of Peptide 21301, Peptide 21303, Peptide 21304, Peptide 21305, Peptide 21306, Peptide 21307, Peptide 21308, Peptide 21309, Peptide 21310, Peptide 21311, Peptide 22325, Peptide 22326, Peptide 22327, Peptide 22328, Peptide 22329, Peptide 22330, Peptide 22331, Peptide 22332, Peptide 22334, Peptide 22335, Peptide 22336, Peptide 22337, Peptide 23250, Peptide 23251, Peptide 23252, Peptide 23253, Peptide 23254, Peptide 23255, Peptide 23256, Peptide 23257, Peptide 23258, Peptide 23259, Peptide 23260, Peptide 23261, Peptide 23262, Peptide 23263, Peptide 23264, Peptide 23265, Peptide 24340, Peptide 24341, Peptide 24342, Peptide 24344, Peptide 24345, Peptide 24346, Peptide 24347, Peptide 24348, Peptide 25501, Peptide 25502, Peptide 25503, Peptide 25504, Peptide 25506, Peptide 25508, Peptide 25516, Peptide 26802, Peptide 26803, Peptide 2680 are done as described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis.

Example 3

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-NH—CH$_3$ (Peptide 27400). [Dat$^1$, D-Ala$^2$, Orn$^{12}$, Abu$^{15}$, Orn$^{21}$, Nle$^{27}$, Asp$^{28}$]hGHRH(1-29)NH—CH$_3$ The synthesis is conducted in a stepwise manner using manual solid phase peptide synthesis equipment. Briefly, [3-[(Methyl-Fmoc-amino)methyl]-indol-1-yl]-acetyl AM resin (Nova Biochem, La Jolla, Calif.) (750 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 µL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-AspfOBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL cleavage cocktail (94% TFA, 3% H$_2$O, 1.5% m-cresol, and 1.5% phenol) at room temperature for 3 hours. To induce peptide precipitation, the cleavage mixture is added dropwise to cold (preferably –20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 118 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 118 mg of crude peptide is dissolved in AcOH/H$_2$O, stirred, filtered and applied on an XBridge Prep OBD™ reversed phase column (4.6×250 mm, packed with C$_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 19 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 27401, Peptide 27403, Peptide 27404, Peptide 27405, Peptide 27406, Peptide 27407, Peptide 27408, Peptide 27409, Peptide 27410, Peptide 27411, Peptide 412, Peptide 27413, Peptide 27414, Peptide 27415, Peptide 27416, Peptide 27417, Peptide 27418, Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are synthesized in the same manner as Peptide 27400, except that these peptides also contain other amino acid substitutions in the peptide sequence. The details for these syntheses are set forth below.

For the synthesis of Peptide 27401, the chemical structure of which [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl Am resin: Fmoc-D-Arg(Pbf)-OH, Fmoc-Asp(OBu$^t$)—OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Dat-OH.

For the synthesis of Peptide 27403, the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27404, the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-AspCOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc- Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27405, the chemical structure of which [N-Me-Tyr$^1$, Orn$^{12}$, Abu$^{15}$, Orn$^{21}$, Nle$^{27}$]hGHRH(1-29)NHCH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27406, the chemical structure of which [N-Me-Tyr$^1$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27407, the chemical structure of which [Dat$^1$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-AsptOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Dat-OH.

For the synthesis of Peptide 27408, the chemical structure of which [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspODBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 27409, the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27410, the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27411 the chemical structure of which [N-Me-Tyr$^1$, D-Ala$^2$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27412 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27413 the chemical structure of which [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)—OH, Fmoc-Nle-OH, Fmoc-Ile-OH, Fmoc-AsptOBu$^1$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 27414 the chemical structure of which [N-Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^r$)—OH, Fmoc-Nle-OH, Fmoc-Ile-OH, Fmoc-AspfOBuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27415 the chemical structure of which [N-Me-Tyr$^1$, Orn$^{12}$, Abu$^{15}$, Orn$^{21}$, Nle$^{27}$, Gab$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Gab-OH, Fmoc-Arg(Pbf)-OH, Fmoc-Asp(OBu$^r$)-OH, Fmoc-Nle-OH, Fmoc-Ile-OH, Fmoc-AspfOBifyOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp^Bu$^t$)-OH, Fmoc-Ala-OH, Fmoc-N-Me-Tyr(tBu)-OH.

For the synthesis of Peptide 27416 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27417 the chemical structure of which [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Ac-Tyr(tBu)-OH.

For the synthesis of Peptide 27418 the chemical structure of which [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Ac-Tyr(tBu)-OH.

For the synthesis of Peptide 27419 the chemical structure of which [Ac-Tyr$^1$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Ac-Tyr(tBu)-OH.

For the synthesis of Peptide 27422 the chemical structure of which [N-Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-Ala-OH, Fmoc-N-Me-Tyr(tBu)-OH.

For the synthesis of Peptide 27423 the chemical structure of which [N-Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 27424 the chemical structure of which [Dat$^1$, Thr$^8$, Orn$^{12}$, Abu$^{15}$, Orn$^{21}$, Nle$^{27}$]hGHRH(1-29)NH—CH$_3$, the following protected amino acids are coupled in the indicated order on the deprotected [3-[(Methyl-Fmoc-amino)methyl]-indol-1-yl]-acetyl AM resin:

Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Dat-OH.

For the synthesis of Peptide 27425 the chemical structure of which [N-Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27440 the chemical structure of which [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBiO-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(Trt)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Dat-OH.

For the synthesis of Peptide 27441 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp^Bu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27442 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp^Bu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27443 the chemical structure of which [N-Me-Tyr$^1$, Orn$^{12}$, Abu$^{15}$, Orn$^{21}$, Nle$^{27}$, D-Arg$^{29}$] hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-Ala-OH, Fmoc-N-Me-Tyr(tBu)-OH.

For the synthesis of Peptide 27444 the chemical structure of which [N-Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)—OH, Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 27445 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27446 the chemical structure of which [N-Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Ala-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 27447 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBify)OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 27448 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^t$)-OH, Fmoc-Nle-OH, Fmoc-Ile-OH, Fmoc-Asp(OBuV)OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 27449 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^t$)-OH, Fmoc-Nle-OH, Fmoc-Ile-OH, Fmoc-Asp(OBify)OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 27450 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^t$)—OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 27451 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Aha$^{30}$]hGHRH(1-30)NH—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^BuVOH, Fmoc-D-Ala-OH, Fmoc-N-Me-Tyr(tBu)-OH.

TFA cleavage and deprotection with the cleavage cocktail, and subsequent purification by semipreparative HPLC of Peptide 27401, Peptide 27403, Peptide 27404, Peptide 27405, Peptide 27406, Peptide 27407, Peptide 27408, Peptide 27409, Peptide 27410, Peptide 27411, Peptide 27412, Peptide 27413, Peptide 27414, Peptide 27415, Peptide 27416, Peptide 27417, Peptide 27418, Peptide 27419, Peptide 27422, Peptide 27423, Peptide 27424, Peptide 27425, Peptide 27440, Peptide 27441, Peptide 27442, Peptide 27443, Peptide 27444, Peptide 27445, Peptide 27446, Peptide 27447, Peptide 27448, Peptide 27449, Peptide 27450, Peptide 27451 are done as described in the case of Peptide 27400. The purified compounds are judged to be substantially (>95%) pure by analytical HPLC. Their molecular masses are checked by electrospray mass spectrometry, and the expected amino acid compositions are confirmed by amino acid analysis.

Example 4

N-Me-Tyr$^1$-D-Ala$^2$-Asp$^3$-Ala$^4$-Ile$^5$-Phe$^6$-Thr$^7$-Gln$^8$-Ser$^9$-Tyr$^{10}$-Arg$^{11}$-Orn$^{12}$-Val$^{13}$-Leu$^{14}$-Abu$^{15}$-Gln$^{16}$-Leu$^{17}$-Ser$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Asp$^{28}$-Arg$^{29}$-NH—CH$_2$—CH$_3$ (Peptide 28420) N-Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$. The synthesis is conducted in a stepwise manner using manual solid phase peptide synthesis equipment. Briefly, 3-[(Ethyl-Fmoc-amino)methyl]-indol-1-yl]-acetyl AM resin (Nova Biochem, La Jolla, Calif.) (610 mg, 0.50 mmol) is deprotected with 20% piperidine in DMF for 5 and 15 minutes and washed according to the protocol described in Table 3. The solution of Fmoc-Arg(Pbf)-OH (975 mg, 1.5 mmol) in DMF is shaken with the washed resin and DIC (235 µL, 1.5 mmol) in a manual solid phase peptide synthesis apparatus for 1 hour. After washing the resin three times with DMF, the coupling reaction was repeated as described above. After the repeated coupling and after the completion of the reaction is proved by negative ninhydrin test, the deprotection and neutralization protocols described in Table 3 are performed in order to remove the Fmoc protecting group and prepare the peptide-resin for coupling of the next amino acid. The synthesis is continued and the peptide chain is built stepwise by coupling the following protected amino acids in the indicated order on the resin to obtain the desired peptide sequence: Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-AspfOBuVOH, Fmoc-D-Ala-OH, Fmoc-N-Me-Tyr(tBu)-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxy-terminus of each residue is free.

The protected amino acids (1.5 mmol each) are coupled with DIC (235 µL, 1.5 mmol) with the exceptions of Fmoc-Asn(Trt)-OH and Fmoc-Gln(Trt)-OH which are coupled with HBTU reagent.

In order to cleave the peptide from the resin and deprotect it, a portion of 250 mg of the dried peptide resin is stirred with 2.5 mL of cleavage cocktail (94% TFA, 3% $H_2O$, 1.5% m-cresol, and 1.5% phenol) at room temperature for 3 hours. To induce peptide precipitation, the cleavage mixture is added dropwise to cold (preferably −20° C.) ether. The precipitated material is collected by filtration or centrifugation and is washed three times with cold ether. The cleaved and deprotected peptide is dissolved in 50% acetic acid and separated from the resin by filtration. After dilution with water and lyophilization, 110 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C18 silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 110 mg of crude peptide is dissolved in AcOH/$H_2O$, stirred, filtered and applied on an XBridge Prep OBD™ reversed phase column (4.6×250 mm, packed with $C_{18}$ silica gel, 300 A pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 16 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 28421, Peptide 28430, Peptide 28431, Peptide 28460, Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are synthesized in the same manner as Peptide 28460, except that these peptides also contain other amino acid substitutions in the peptide sequence. The details for these syntheses are set forth below.

For the synthesis of Peptide 28421 the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-29)NH—$CH_2$—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspODBu-VOH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28430 the chemical structure of which [N-Me-Tyr$^1$, D-Ala$^2$, Gln$^8$, Orn$^{12}$, Abu$^{15}$, Orn$^{21}$, Nle$^{27}$]hGHRH(1-29)NH—$CH_2$—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(tBu)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 28431 the chemical structure of which [N-Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—$CH_2$—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Thr(tBu)-OH, Fmoc-Thr(tBu)-OH, Fmoc-Phe-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28460 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—$CH_2$—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^t$)—OH, Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^t$)-OH, Fmoc-D-Ala-OH, Fmoc-N-Me-Tyr(tBu)-OH.

For the synthesis of Peptide 28462 the chemical structure of which [N-Me-Tyr$^1$, D-Ala$^2$, Fpa5$^6$, Orn$^{12}$, Abu$^{15}$, Orn$^{21}$, Nle$^{27}$]hGHRH(1-29)NH—$CH_2$—$CH_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^t$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-

OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28463 the chemical structure of which [N-Me-Tyr$^1$, D-Ala$^2$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 28464 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28465 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu'J-OH, Fmoc-D-Ala-OH, Fmoc-N-Me-Tyr(tBu)-OH.

For the synthesis of Peptide 28466 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28467 the chemical structure of which [N-Me-Tyr$^1$, D-Ala$^2$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-AspfOBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28468 the chemical structure of which [N-Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Arg(Pbf)-OH, Fmoc-Asp(OBu$^r$)—OH$_>$ Fmoc-Nle-OH, Fmoc-Ile-OH, Fmoc-Asp-COBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Fmoc-N-Me-Tyr(tBu)-OH.

For the synthesis of Peptide 28469 the chemical structure of which [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28470 the chemical structure of which [Dat$^1$, D-Ala$^2$, Orn$^{12}$, Abu$^{15}$, Orn$^{21}$, Nle$^{27}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Ser(Trt)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28471 the chemical structure of which [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-AspODBu-VOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-

OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28472 the chemical structure of which [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)—OH, Fmoc-Nle-OH, Fmoc-Ile-OH, Fmoc-Asp-COBu$^1$)-OH, Fmoc-Gln-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Dat-OH.

For the synthesis of Peptide 28473 the chemical structure of which [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-Asp(OBu$^r$)—OH, Fmoc-Nle-OH, Fmoc-Ile-OH, Fmoc-Asp-tOBu$^1$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Fpa5-OH, Fmoc-Ile-OH, Fmoc-Ala-OH, Fmoc-Asp(OBu$^r$)-OH, Fmoc-D-Ala-OH, Dat-OH.

For the synthesis of Peptide 28474 the chemical structure of which [Dat$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-D-Arg(Pbf)-OH, Fmoc-AspODBuVOH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Asn(Trt)-OH, Fmoc-Thr(tBu)-OH, Fmoc-Phe-OH, Fmoc-Ile-OH, Fmoc-Ala-OH, Fmoc-Asp(OBu$^r$)-OH, Fmoc-D-Ala-OH, Dat-OH.

For the synthesis of Peptide 28475 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)—OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28476 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Aha-OH, Fmoc-Arg(Pbf)-OH, Fmoc-Asp(OBu$^r$)—OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28477 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Amc-OH, Fmoc-Arg(Pbf)-OH, Fmoc-Asp(OBu$^r$)—OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28478 the chemical structure of which [N-Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Har(Pbf)-OH, Fmoc-Arg(Pbf)-OH, Fmoc-Asp(OBu$^r$)-OH, Fmoc-Nle-OH, Fmoc-Ile-OH, Fmoc-Asp^BuVOH, Fmoc-Gln(Trt)-OH, Fmoc-Leu-OH, Fmoc-Leu-OH, Fmoc-Orn(Boc)-OH, Fmoc-Arg(Pbf)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-Arg(Pbf)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ile-OH, Fmoc-Ala-OH, Fmoc-Asp^Bu$^1$)-OH, Fmoc-D-Ala-OH, Fmoc-N-Me-Tyr(tBu)-OH.

For the synthesis of Peptide 28479 the chemical structure of which [N-Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_2$—CH$_3$, the following protected amino acids are coupled in the indicated order on the deprotected [3-[(Methyl-Fmoc-amino)methyl]-indol-1-yl]-acetyl AM resin: Fmoc-Apa-OH, Fmoc-Arg(Pbf)-OH, Fmoc-Asp(OBu$^r$)-OH, Fmoc-Nle-OH, Fmoc-Ile-OH, Fmoc-Asp(OBu$^r$)-OH, Fmoc-Gln(Trt)-OH, Fmoc-Leu-OH, Fmoc-Leu-OH, Fmoc-Orn(Boc)-OH, Fmoc-His(Trt)-OH, Fmoc-Ala-OH, Fmoc-Ser(tBu)-OH, Fmoc-Leu-OH, Fmoc-Gln(Trt)-OH, Fmoc-Abu-OH, Fmoc-Leu-OH, Fmoc-Val-OH, Fmoc-Orn(Boc)-OH, Fmoc-His(Trt)-OH, Fmoc-Tyr(tBu)-OH, Fmoc-Ser(Trt)-OH, Fmoc-Gln(Trt)-OH, Fmoc-Thr(tBu)-OH, Fmoc-Phe-OH, Fmoc-Ala-OH, Fmoc-Asp(OBu$^r$)-OH, Fmoc-D-Ala-OH, Fmoc-N-Me-Tyr(tBu)-OH.

TFA cleavage and deprotection with the cleavage cocktail, and subsequent purification by semipreparative HPLC of Peptide 28421, Peptide 28430, Peptide 28431, Peptide 28460, Peptide 28461, Peptide 28462, Peptide 28463, Peptide 28464, Peptide 28465, Peptide 28466, Peptide 28467, Peptide 28468, Peptide 28469, Peptide 28470, Peptide 28471, Peptide 28472, Peptide 28473, Peptide 28474, Peptide 28475, Peptide 28476, Peptide 28477, Peptide 28478, Peptide 28479 are done as described in the case of Peptide 28420. The purified compounds are judged to be substantially (>95%) pure by analytical HPLC. Their molecular masses are checked by electrospray mass spectrometry, and the expected amino acid compositions are confirmed by amino acid analysis.

Example 5

Dat$^1$-D-Ala$^2$-Asp$^3$-Ala$^4$-Ile$^5$-Phe$^6$-Thr$^7$-Asn$^8$-Ser$^9$-Tyr$^{10}$-Arg$^{11}$-Orn$^{12}$-Var$^3$-Leu$^{14}$-Abu$^{15}$-Gln$^{16}$-Leu$^{17}$-Leu$^{18}$-Ala$^{19}$-Arg$^{20}$-Orn$^{21}$-Leu$^{22}$-Leu$^{23}$-Gln$^{24}$-Asp$^{25}$-Ile$^{26}$-Nle$^{27}$-Ser$^{28}$-Arg$^{29}$-Gln-Gab$^{30}$-NH$_2$ (Peptide 29702) Dat$^1$, D-Ala$^2$, Orn$^{12}$, Abu$^{15}$, Orn$^{21}$, Nle$^{27}$, Gln-Gab$^{30}$]hGHRH(1-30)-NH$_2$. The synthesis is conducted in a stepwise manner using manual solid phase peptide synthesis equipment. Briefly, para-methylbenzhydrylamine (MBHA) resin (Bachem, King of Prussia, Pa.) (720 mg, 0.50 mmol) is pre-swollen in DCM and neutralized with 5% DIEA in DCM and washed according to the protocol described in Table I. The solution of Boc-Gab-OH (265 mg, 1.5 mmol) in DMF-DCM (1:1) is shaken with the neutralized resin and DIC (235 µL, 1.5 mmol) in a manual solid phase peptide synthesis apparatus for 1 hour. After the completion of the coupling reaction is proved by negative ninhydrin test, the deprotection and neutralization protocols described in Table 2 are performed in order to remove the Boc protecting group and prepare the peptide-resin for coupling of the next amino acid. The synthesis is continued and the peptide chain is built stepwise by coupling the following protected amino acids in the indicated order on the resin to obtain the desired peptide sequence: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

These protected amino acid residues (also commonly available from Novabiochem, Advanced Chemtech, Bachem, and Peptides International) are represented above according to a well accepted convention. The suitable protecting group for the side chain functional group of particular amino acids appears in parentheses. The OH groups in the above formulae indicate that the carboxyl terminus of each residue is free.

The protected amino acids (1.5 mmol each) are coupled with DIC (235 µL, 1.5 mmol) with the exceptions of Boc-Asn-OH and Boc-Gln-OH which are coupled with their pre-formed HOBt esters.

In order to cleave the peptide from the resin and deprotect it, a portion of 250 mg of the dried peptide resin is stirred with 0.5 mL m-cresol and 5 mL hydrogen fluoride (HF) at 0° C. for 2 hours. After evaporation of the HF under a stream of nitrogen and in vacuo, the residue is washed with dry diethyl ether and ethyl acetate. The cleaved and deprotected peptide is dissolved in 50% acetic acid and separated from the resin by filtration. After dilution with water and lyophilization, 109 mg crude product is obtained.

The crude peptide is checked by analytical HPLC using a Hewlett-Packard Model HP-1090 liquid chromatograph equipped with a Supelco Discovery HS C18 reversed-phase column (2.1 mm×5 cm, packed with C$_{18}$ silica gel, 300 Å pore size, 3 µm particle size) (Supelco, Bellefonte, Pa.). Linear gradient elution (e.g., 40-70% B) is used with a solvent system consisting of (A) 0.1% aqueous TFA and (B) 0.1% TFA in 70% aqueous MeCN, and the flow rate is 0.2 mL/min. Purification is performed on a Beckman System Gold HPLC system (Beckman Coulter, Inc., Brea, Calif.) equipped with 127P solvent Module; UV-VIS Detector, model 166P; Computer workstation with CPU Monitor and printer, and 32-Karat software, version 3.0. 109 mg of crude peptide is dissolved in AcOH/H$_2$O, stirred, filtered and applied on an XBridge Prep OBD™ reversed phase column (4.6×250 mm, packed with C$_{18}$ silica gel, 300 Å pore size, 5 µm particle size) (Waters Co., Milford, Mass.). The column is eluted with a solvent system described above in a linear gradient mode (e.g., 40-60% B in 120 min); flow rate 12 mL/min. The eluent is monitored at 220 nm, and fractions are examined by analytical HPLC. Fractions with purity higher than 95% are pooled and lyophilized to give 27 mg pure product. The analytical HPLC is carried out on a Supelco Discovery C18 reversed-phase column described above using isocratic elution with a solvent system described above with a flow rate of 0.2 mL/min. The peaks are monitored at 220 and 280 nm. The product is judged to be substantially (>95%) pure by analytical HPLC. Molecular mass is checked by electrospray mass spectrometry, and the expected amino acid composition is confirmed by amino acid analysis.

In accordance with the above procedure Peptide 29701, Peptide 29703, Peptide 29704, Peptide 29706, Peptide 29708, Peptide 29710, Peptide 29720, Peptide 29721, Peptide 29722, Peptide 29723, Peptide 29724 are synthesized in the same manner as Peptide 29702, except that these peptides also contain other amino acid substitutions in the peptide sequence, and acyl moieties at their N-termini. The details for these syntheses are set forth below.

For the synthesis of Peptide 29701 the chemical structure of which is [N-Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$; the following protected amino acids are coupled in the indicated order on the MBHA resin: Boc-Gab-OH, Boc-Gln-OH, Boc-Arg (Tos)-OH, Boc-Asp(OcHx)-OH, Boc-NLe-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Boc-N-Me-Tyr(Bzl)-OH.

For the synthesis of peptide 29703 the chemical structure of which is N-Me-Tyr$^1$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-NLe-OH, Boc-Ile-OH, Boc-Asp(OcHx), Boc-Gln-OH, Boc-Leu-OH, Boc-Leu-OH, Boc-Orn(2ClZ)-OH, Boc-Arg(Tos)-OH, Boc-Ala-OH, Boc-Ser (Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2ClZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(Bzl)-OH.

For the synthesis of peptide 29704 the chemical structure of which is [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-

OH, Boc-Asp(OcHx)-OH, Boc-NLe-OH, Boc-Ile-OH, Boc-Asp(OcHx), Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2ClZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-Ala-OH, Boc-N-Me-Tyr(Bzl)-OH.

For the synthesis of Peptide 29706 the chemical structure of which [Tfa-Tyr$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Abu-OH, Tfa-Tyr-OH.

For the synthesis of Peptide 29708 the chemical structure of which [N-Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 29710 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Ser(Bzl)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 29720 the chemical structure of which [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29721 the chemical structure of which [Dat$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Ala-OH, Dat-OH.

For the synthesis of Peptide 29722 the chemical structure of which [Tfa-Tyr$^1$, D-Abu$^2$, Gln$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Gln-OH, Boc-Thr(Bzl)-OH, Boc-Phe-OH, Boc-Ile-OH, Boc-Ala-OH, Boc-Asp(OcHx)-OH, Boc-D-Abu-OH, Tfa-Tyr-OH.

For the synthesis of Peptide 29723 the chemical structure of which [N-Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Asn-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

For the synthesis of Peptide 29724 the chemical structure of which [N-Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$]hGHRH(1-30)NH$_2$, the following protected amino acids are coupled in the indicated order on the MBHA resin: Boc-Gab-OH, Boc-Gln-OH, Boc-Arg(Tos)-OH, Boc-Asp(OcHx)-OH, Boc-Nle-OH, Boc-Ile-OH, Boc-Asp(OcHx)-OH, Boc-Gln-OH, Boc-Leu-OH, Boc-Leu-OH, Boc-Orn(2ClZ)-OH, Boc-Arg(Tos)-OH, Boc-Ala-OH, Boc-Ser(Bzl)-OH, Boc-Leu-OH, Boc-Gln-OH, Boc-Abu-OH, Boc-Leu-OH, Boc-Val-OH, Boc-Orn(2ClZ)-OH, Boc-Arg(Tos)-OH, Boc-Tyr(2BrZ)-OH, Boc-Ser(Bzl)-OH, Boc-Ala-OH, Boc-Thr(Bzl)-OH, Boc-Fpa5-OH, Boc-Ile-OH, Boc-Ala-OH, Boc-Asp(OcHx)-OH, Boc-D-Ala-OH, Boc-N-Me-Tyr(2BrZ)-OH.

HF cleavage and deprotection, and subsequent purification by semipreparative HPLC of Peptide 29701, Peptide 29703, Peptide 29704, Peptide 29706, Peptide 29708, Peptide 29710, Peptide 29720, Peptide 29721, Peptide 29722, Peptide 29723, Peptide 29724 are done as described in the case of Peptide 21300. The purified compounds are judged to be substantially (>95%) pure by analytical HPLC. Their molecular masses are checked by electrospray mass spectrometry, and the expected amino acid compositions are confirmed by amino acid analysis.

Example 6

Aqueous Solution for Intramuscular Injection

[N-Me-Tyr$^1$, Gln$^8$, Orn$^{12}$, Abu$^{15}$, Orn$^{21}$, Nle$^{27}$, Asp$^{28}$, Agm29]hGHRH(1-29)

| (Peptide 20356) | 500.0 mg |
| Gelatin, nonantigenic | 5.0 mg |
| Water for injection q.s | 100.0 mL |

The gelatin and GHRH agonist Peptide 20356 are dissolved in water for injection, and then the solution is sterile filtered.

Example 7

Long Acting Intramuscular Injectable Formulation
(Sesame Oil Gel)

[N-Me-Tyr$^1$, Gln$^8$, Orn$^{12}$, Abu$^{15}$, Orn$^{21}$, Nle$^{27}$, Asp$^{28}$, Agm$^{29}$]hGHRH(1-29)

| (Peptide 20356) | 10.0 mg |
| Aluminum monostearate, USP | 20.0 mg |
| Sesame oil q.s. | 1.0 mL |

The aluminum monostearate is combined with the sesame oil and heated to 125° C. with stirring until a clear yellow solution forms. This mixture is then autoclaved for sterility and allowed to cool. The GHRH agonist Peptide 20356 is then added aseptically with trituration. Particularly preferred agonists are salts of low solubility, e.g., pamoate salts and the like. These exhibit long duration of activity.

Example 8

Long Acting Intramuscular (IM)
Injectable-Biodegradable Polymer Microcapsules

Microcapsules are made from the following:

| 25/75 glycolide/lactide copolymer (0.5 intrinsic viscosity) | 99% |
| [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) (Peptide 20356) | 1% |
| 25 mg of the above microcapsules are suspended in 1.0 mL of the following vehicle: | |
| Dextrose | 5.0% |
| CMC, sodium | 0.5% |
| Benzyl alcohol | 0.9% |
| Tween 80 | 0.1% |
| Water, purified q.s. | 100% |

Example 9

Growth hormone releasing activity. Growth hormone releasing was assayed by using a superfused rat pituitary cell system as described in S. Vigh and A. V. Schally, Peptides 5, Suppl: 241-347, 1984. The new synthetic peptide analog of hGHRH P20356 and JI-38 (as control) were administered for 3 minutes (1 mL perfusate) at 1 nM concentration as shown below. Fractions of 1 ml are collected and the GH content in each was determined by ELISA. Peptide P20356 was about 3 times more potent in vitro than JI-38. Table 4 shows GH-releasing effects of GHRH agonist P20356 (MR-356) and JI-38 in superfused rat pituitary cells.

TABLE 4

GH Response P-20356 vs JI-38
Basal GH (ng/ml) 42.51

| GH Response (ng/ml) | 1 | 2 | 3 | Average |
| --- | --- | --- | --- | --- |
| P-20356 (1 nM) | | | | |
| 1 | 49.98 | 54.99 | 52.37 | 52.45 |
| 2 | 310.58 | 325.76 | 376.11 | 337.48 |
| 3 | 491.01 | 602.1 | 576.26 | 556.46 |
| 4 | 399.95 | 270.02 | — | 334.99 |
| 5 | 200.64 | 195.18 | — | 197.91 |
| JI-38 (1 nM) | | | | |
| 21 | 42.46 | 56.07 | — | 49.27 |
| 22 | 143.58 | 119.83 | — | 131.71 |
| 23 | 222.13 | 167.23 | — | 194.68 |
| 24 | 142.96 | 131.93 | — | 137.45 |
| 25 | 96.34 | 97.05 | — | 96.70 |

Conclusions: P-20356 is 2-3 times more potent than JI-38

Pituitary cells from 2 male rats were used for each channel of the superfusion system. The cells were exposed to 3-min pulses of the new GHRH agonists or to JI-38 as standard every 30 min. Outflowing samples of each channel (1 ml) were collected every 3 min, and GH levels were determined by ELISA.

Example 10

Receptor binding assay. Ligand competition assay with $^{125}$I-labeled [His$^1$, Nle$^{27}$]hGHRH(1-32)-NH$_2$ was used to determine the binding affinities of the novel hGHRH agonists to membrane receptors of rat anterior pituitary cells. The methods used have been described in detail (Halmos G, et al. Receptor 3: 87-97, 1993). Briefly, radioiodonated [His$^1$, Nle$^{27}$]hGHRH(1-32)-NH$_2$ is prepared by the chloramine-T method. In competitive binding analyses, $^{125}$I-labeled [His$^1$, Nle$^{27}$]hGHRH(1-32)-NH$_2$ (0.2 nM) was displaced by the GHRH analogs at $10^{-6}$-$10^{-12}$ M. The final binding affinities were calculated using the LIGAND-PC computerized curve-fitting program. Relative affinities were compared to hGHRH(1-29) and/or analog JI-38 (Izdebski J, et al. Proc. Natl. Acad. Sci. 92: 4872-4876, 1995) and calculated as the ratio of IC$_{50}$ of the tested peptide to the IC$_{50}$ of the standard. IC$_{50}$ is the dose of the tested peptides causing 50% inhibition of specific binding to receptors.
GHRH Receptor Binding Studies
Binding Affinities
Materials and Methods Preparation of human pituitary membrane fraction and receptor binding of GHRH agonists were performed by using a sensitive in vitro ligand competition assay based on binding of $^{125}$I-labeled JV-1-42 to human pituitary membrane homogenates. Normal human pituitaries were purchased from the National Hormone and Peptide Program (A. F. Parlow, Los Angeles, County Harbor-UCLA Medical Center, Torrance, Calif.). Briefly, in competitive binding analysis, $^{125}$I-labeled JV-1-42 (~0.2 nM) was displaced by GHRH agonists at $10^{-6}$ to $10^{-12}$ M.

The final binding affinities were expressed as IC$_{50}$ values and were calculated by using the LIGAND PC computerized curve-fitting program of Munson and Rodbard as modified by McPherson.
Results The results of these experiments are given in the Table 5. IC$_{50}$ values of the best agonists were in the 0.01-0.09 nM range. Based on the receptor binding results, all the new GHRH agonists exceeded the binding affinity of the reference peptide JI-38. Some of these new GHRH agonists tested showed the highest GHRH receptor binding affinity, their $IC_{50}$ values being 45-406 times lower than that of GHRH(1-29). Based on its $IC_{50}$ value, GHRH agonist P20356 showed 171 times higher binding affinity than the reference compound JI-38.

TABLE 5

| GHRH agonists | $IC_{50}$ (nM) | Relative affinitiy (Binding potency) vs GHRH | vs JI-38 |
|---|---|---|---|
| GHRH (1-29) | 4.06 | 1 | |
| JI-38 | 1.71 | 2.4 | 1 |
| P20303 | 0.09 | 45.1 | 19.0 |
| P20350 | 0.04 | 101.5 | 42.7 |
| P20356 | 0.01 | 406.0 | 171.0 |
| P25502 | 0.07 | 58.0 | 24.4 |
| P29702 | 0.05 | 81.2 | 34.2 |

* Expressed relative to GHRH(1-29) = 1 or JI-38 (GHRH agonist) = 1, Values were calculated from duplicate tubes.

GHRH Receptor Binding Studies
Binding Affinities
Materials and Methods

Preparation Preparation of human pituitary membrane fraction and receptor binding of GHRH agonists were performed by using a sensitive in vitro ligand competition assay based on binding of $^{125}$I-labeled [His$^1$, Nle$^{27}$]hGHRH(1-32)NH$_2$ to human pituitary membrane homogenates. Normal human pituitaries were purchased from the National Hormone and Peptide Program (A. F. Parlow, Los Angeles, County Harbor—UCLA Medical Center, Torrance, Calif.).

Briefly, in competitive binding analysis, [His$^1$, $^{125}$I-Tyr$^{10}$, Nle$^{27}$]hGHRH(1-32)NH$_2$ (0.2 nM) was displaced by GHRH agonists at $10^{-6}$ to $10^{-12}$ M. The final binding affinities were expressed as $IC_{50}$ values and were calculated by using the LIGAND PC computerized curve-fitting program of Munson and Rodbard as modified by McPherson.

Results

The results of these experiments are given in the Table 6. $IC_{50}$ values of the best agonists were in the 0.04-0.09 nM range. Based on the receptor binding results all new GHRH agonists exceeded the binding affinity of reference peptides JI-34, JI-36 and JI-38. Some of these new GHRH agonists showed the highest GHRH receptor binding affinity, their $IC_{50}$ values being 21-48 times lower than that of the GHRH agonist JI-38.

TABLE 6

| GHRH agonists | $IC_{50}$ (nM) | Relative affinitiy (Binding potency) vs GHRH | vs JI-38 |
|---|---|---|---|
| GHRH(1-29) | 5.92 | 1 | |
| JI-34 | 1.37 | 4.32 | |
| JI-36 | 1.82 | 3.25 | |
| JI-38 | 1.95 | 3.03 | 1 |
| P-23252 | 0.14 | 42.3 | 13.9 |
| P-23254 | 0.07 | 84.5 | 27.8 |
| P-23256 | 0.04 | 148.0 | 48.7 |
| P-21304 | 0.08 | 74.0 | 24.4 |
| P-20352 | 0.07 | 84.5 | 27.8 |

* Expressed relative to GHRH(1-29) = 1 or JI-38 (GHRH agonist) = 1
Values were calculated from duplicate or triplicate tubes.

GHRH Receptor Binding Studies
Binding Affinities
Materials and Methods

Preparation of human pituitary membrane fraction and receptor binding of GHRH agonists were performed by using a sensitive in vitro ligand competition assay based on binding of $^{125}$I-labeled JV-1-42 to human pituitary membrane homogenates. Normal human pituitaries were purchased from the National Hormone and Peptide Program (A. F. Parlow, Los Angeles, County Harbor-UCLA Medical Center, Torrance, Calif.).

Briefly, in competitive binding analysis, $^{125}$I-labeled JV-1-42 (~0.2 nM) was displaced by GHRH agonists at $10^{-6}$ to $10^{-12}$ M. The final binding affinities were expressed as $IC_{50}$ values and were calculated by using the LIGAND PC computerized curve-fitting program of Munson and Rodbard as modified by McPherson Results The results of these experiments are given in the Table 7. $IC_{50}$ values of the best agonists were in the 0.16-0.87 nM range. Based on the receptor binding results most of the new GHRH agonists exceeded the binding affinity of reference peptides JI-38. Some of these new GHRH agonists showed 5-27 times higher binding potency than GHRH agonist JI-38. See Table 7.

TABLE 7

$IC_{50}$ values and binding activities of new GHRH agonistic analogs

| GHRH agonists | $IC_{50}$ (nM) | Relative affinitiy (Binding potency) vs JI-38 |
|---|---|---|
| JI-38 | 4.35 | 1 |
| P-21300 | 3.61 | 1.20 |
| P-21301 | 2.99 | 1.45 |
| P-21303 | 1.87 | 2.32 |
| P-22325 | 3.80 | 1.14 |
| P-22326 | 0.71 | 6.12 |
| P-22327 | 1.99 | 2.18 |
| P-20357 | 0.86 | 5.06 |
| P-20350 | 0.52 | 8.37 |
| P-20351 | 3.44 | 1.26 |
| P-20356 | 0.27 | 16.11 |
| P-20359 | 3.05 | 1.43 |
| P-20361 | 0.82 | 5.30 |
| P-20367 | 1.70 | 2.56 |
| P-25501 | 1.07 | 4.07 |
| P-25502 | 0.33 | 13.18 |
| P-25503 | 1.18 | 3.67 |
| P-25504 | 1.44 | 3.02 |
| P-27413 | 2.45 | 1.78 |
| P-27414 | 1.56 | 2.79 |
| P-27415 | 3.02 | 1.44 |
| P-29702 | 0.86 | 5.06 |
| P-29703 | 1.22 | 3.57 |
| P-27400 | 3.35 | 1.30 |
| P-27401 | 2.74 | 1.59 |
| P-27403 | 0.16 | 27.19 |
| P-27404 | 0.87 | 5.00 |
| P-27405 | 1.08 | 4.03 |
| P-27406 | 0.30 | 14.5 |
| P-27407 | 3.00 | 1.45 |
| P-27408 | 0.55 | 7.91 |
| P-27409 | 1.06 | 4.10 |
| P-27410 | 0.83 | 5.24 |
| P-28420 | 0.52 | 8.37 |
| P-28421 | 1.47 | 2.96 |

* Expressed relative to JI-38 (GHRH agonist) = 1 Values were calculated from duplicate tubes, "reference compound.

Example 11

In vivo tests on endocrine activity of new GHRH agonists (Intravenous administration). For in vivo tests based on intravenous administration, adult male Sprague-Dawley rats were anesthetized with pentobarbital (6 mg/100/g, b.w.), and GHRH agonists were injected 20 minutes after the injection of pentobarbital. Blood samples were taken from the jugular vein (pretreated level), immediately after hGHRH(1-29)NH$_2$ injection (as a control) or after hGHRH analogs injection. Blood samples were taken from the jugular vein 5, 15 and 30 minutes after the injection. The blood samples were centrifuged, plasma was removed and the GH level was measured by ELISA. The results were expressed as potency relative to hGHRH(1-29)NH$_2$ (Table 8).

TABLE 8

GH releasing potencies of hGHRH analogs in vivo relative to JI-38 (=1) in the rat after i.v. injection

| hGHRH Analog | After (min) | Potency |
|---|---|---|
| P-20356 | 5 | 1.07 |
|  | 15 | 0.91 |
|  | 30 | 1.22 |
| P-21300 | 5 | 0.39 |
|  | 15 | 0.51 |
|  | 30 | 0.81 |
| P-21301 | 5 | 0.79 |
|  | 15 | 0.92 |
|  | 30 | 1.00 |
| P-21303 | 5 | 0.79 |
|  | 15 | 1.14 |
|  | 30 | 0.81 |
| P-22326 | 15 | 0.28 |
|  | 30 | 0.94 |
| P-25502 | 5 | 6.76 |
|  | 15 | 5.40 |
|  | 30 | 5.83 |
| P-25504 | 5 | 1.66 |
|  | 15 | 1.65 |
|  | 30 | 1.37 |
| P-27403 | 15 | 5.01 |
|  | 30 | 4.01 |
| P-27450 | 5 | 0.07 |
|  | 15 | 0.11 |
|  | 30 | 0.49 |
| P-28475 | 5 | 0.19 |
|  | 15 | 0.36 |
|  | 30 | 0.92 |
| P-29702 | 5 | 0.98 |
|  | 15 | 0.99 |
|  | 30 | 1.22 |

Subcutaneous Administration. Adult male rats were used and anesthetized with pentobarbital (6 mg/100 g, b.w.), by i.p. injection. 20 minutes after the injection of pentobarbital, blood samples were taken from the jugular vein (pretreated level), immediately after hGHRH(1-29)NH$_2$ (as a control) or hGHRH analogs were injected subcutaneously (s.c). Blood samples were taken from the jugular vein 5, 15 and/or 30 minutes after the injection. The blood samples were centrifuged, plasma was removed and the GH level was measured by ELISA. The results are summarized in terms of potency in Table 9.

TABLE 9

GH releasing potencies of hGHRH analogs after subcutaneous (s.c.) injection relative to JI-38 (=1)

| hGHRH analog | After (min) | Potency |
|---|---|---|
| P-20350 | 15 | 1.53 |
|  | 30 | 1.17 |
| P-20351 | 15 | 0.38 |
|  | 30 | 0.44 |
| P-20353 | 15 | 0.26 |
|  | 30 | 0.31 |
| P-20356 | 15 | 1.72 |
|  | 30 | 1.09 |
| P-20357 | 5 | 0.63 |
|  | 15 | 1.07 |
|  | 30 | 1.41 |
| P-20360 | 15 | 0.24 |
|  | 30 | 0.39 |
| P-20361 | 15 | 1.18 |
|  | 30 | 1.50 |
| P-20367 | 15 | 1.12 |
|  | 30 | 2.01 |
| P-20373 | 15 | 0.23 |
|  | 30 | 0.88 |
| P-21301 | 15 | 0.41 |
|  | 30 | 0.74 |
| P-221303 | 15 | 0.95 |
|  | 30 | 1.45 |
| P-22325 | 5 | 0.33 |
|  | 15 | 0.68 |
|  | 30 | 1.03 |
| P-22326 | 15 | 1.76 |
|  | 30 | 2.31 |
| P-22327 | 15 | 1.15 |
|  | 30 | 1.30 |
| P-25501 | 5 | 1.40 |
|  | 15 | 1.36 |
|  | 30 | 1.63 |
| P-25502 | 15 | 1.10 |
|  | 30 | 0.94 |
| P-25503 | 5 | 0.55 |
|  | 15 | 0.64 |
|  | 30 | 0.63 |
| P-25504 | 15 | 0.78 |
|  | 30 | 0.98 |
| P-27400 | 15 | 0.47 |
|  | 30 | 0.38 |
| P-27401 | 15 | 0.61 |
|  | 30 | 0.73 |
| P-27403 | 15 | 3.60 |
|  | 30 | 2.57 |
| P-27404 | 15 | 2.07 |
|  | 30 | 1.47 |
| P-27405 | 15 | 1.60 |
|  | 30 | 1.13 |
| P-27406 | 15 | 0.47 |
|  | 30 | 0.50 |
| P-27409 | 15 | 1.47 |
|  | 30 | 1.31 |
| P-27412 | 15 | 1.10 |
|  | 30 | 1.29 |
| P-27413 | 15 | 0.36 |
|  | 30 | 0.57 |
| P-27414 | 15 | 1.30 |
|  | 30 | 1.23 |
| P-27415 | 15 | 0.45 |
|  | 30 | 0.41 |
| P-27425 | 15 | 0.49 |
|  | 30 | 0.31 |
| P-29701 | 5 | 0.92 |
|  | 15 | 1.30 |
|  | 30 | 1.55 |
| P-29702 | 15 | 0.53 |
|  | 30 | 0.73 |
| P-29703 | 5 | 1.18 |
|  | 15 | 0.96 |
|  | 30 | 1.04 |

Analysis of endocrine tests: Following intravenous administration, the new analogs stimulated growth hormone levels to a greater extent than hGHRH(1-29)NH$_2$ or JI-38. The effect was long lasting which indicated that the analogs have higher receptor affinity and also increased peptidase resistance. The most potent analogs when administered i.v. were P-27403 and P-25502. Following subcutaneous administration, the analogs that stimulated greater growth hormone levels than hGHRH or JI-38 were P-22326, P-20350, P-20356, P-27403, P-27404, P-27409, P-25501, and P-25502.

Results of i.v. and s.c. administration showed different biological activity patterns. Analogs given by i.v. administration may be subjected to degradation in the blood stream. Analogs given s.c. could be potentially degraded by peptidase at the site of injection. Thus, it is believed that activity of the peptide may depend on favorable transport properties, suitable binding to plasma proteins, and peptide stability. The above findings therefore indicate that the analogs showing better activity when given subcutaneously are resistant to local degradation at the injection site and they may also be less susceptible to enzyme degradation in the blood stream. In conclusion, the most potent analogs when administered i.v. were P-27403 and P-25502. Following subcutaneous administration, the analogs that stimulated greater growth hormone levels than hGHRH or JI-38 were P-22326, P-20350, P-20356, P-27403, P-27404, P-27409, P-25501, and P-25502.

Example 12

Effect of GHRH Agonist P-27403 on INS-1 Cells

Rat insulinoma cells (INS-1) were cultured in RPMI Medium 1640 (PAA) containing 2 mM L-glutamine, 10% FBS, 1 mM Na-pyruvate, 50 µM 2-mercaptoethanol, and 100 U/mL penicillin/streptomycin (Gibco) at 37° C. in a 5% $CO_2$ humidified incubator. Medium was exchanged every second day and cells were passaged once per week. INS-1 cells were treated with the GHRH agonist P-27403 at concentrations from $10^{-7}$ to $10^{-9}$ M for 24 hrs and was analyzed for viability and apoptosis. Viability was assessed using CellTiter 96 AQueous One Solution Cell Proliferation Assay (Promega) according to the manufacturer's instructions. Apoptosis was assayed by determination of caspase 3/7 activity using Caspase-Glo 3/7 Assay (Promega) according to manufacturer's instructions. Exposure to P-27403 resulted in increased viability at all concentrations used, as compared to control (DMSO). A significant effect was seen at a concentration of $10^{-8}$ M of P-27403 with an improvement of 15% in viability, as compared to control (FIG. 1A). In addition, treatment of INS-1 cells with P-27403 resulted in an overall reduction of apoptosis, as assessed by decreased caspase 3/7 activity (FIG. 1B). The most effective concentrations of P-27403 that provided significantly reduced apoptosis, as compared to control, were $10^{-8}$ and $10^{-9}$ M.

For determination of proliferation activity, BrdU incorporation was performed in INS-1 cells following exposure to P-27403. Proliferation was measured using BrdU Cell Proliferation Assay (Millipore) following the manufacturer's description. The maximal enhancement in proliferation rate of 16% compared to control was found at $10^{-8}$ M concentration of P-27403 (FIG. 1C).

Example 13

Effect of GHRH Analog P-27403 on Rat Islets and Co-Culture of Islet/Adrenal Cells Rat Islet Isolation and Culture:
Pancreatic islets were isolated from female Wistar rats as described in prior art, and according to guidelines established by the University Institutional Animal Care and Use Committee. Briefly, animals were anesthetized by 3% isoflurane and digestion solution (Collagenase V; Sigma-Aldrich) was injected via the pancreatic duct. Islets were isolated by discontinuous Ficoll gradient centrifugation (Sigma-Aldrich). Isolated islets were cultured in RPMI 1640 (PAA) supplemented with 10% FBS at 37° C. in a 5% $CO_2$ atmosphere prior to further experimentation. Yield and purity of islets were determined by microscopic sizing after staining with dithizone (Sigma-Aldrich) as previously described.

Adrenal Cell Isolation and Culture:
Female Wistar rats were used as adrenal donors according to guidelines established by the University Institutional Animal Care and Use Committee. After euthanization, the adrenal glands were rapidly removed and kept in PBS at 4° C. After removal of adipose tissue, the capsule was removed. The tissue was then incubated at 37° C. in PBS containing collagenase type II (2.0 mg/ml; Sigma-Aldrich) and DNase (0.15 mg/ml; Sigma-Aldrich). After incubation for 30 min, the digestion was stopped by adding cold PBS. The dispersed cells were filtered through a 100 µm restrainer and centrifuged at 1200 g for 5 min at 4° C. Erythrocyte lysis buffer was added to the cell pellet and incubated for 5 min at room temperature. After two washing steps, cells were collected by centrifugation and resuspended in RPMI 1640 containing 10% FBS for culture at 37° C. in 5% $CO_2$ atmosphere.

Co-Culture System:
Isolated adrenal cells were plated in a 24-well tissue culture plate at a density of 150,000 cells per well. After 2 days, media were exchanged and P-27403 ($10^{-8}$ M) or DMSO was added to the fresh media. For the co-culture, 150 islet equivalents were seeded in inserts (1.0 µm pore size, Greiner Bio One) and treated with P-27403 ($10^{-8}$ M) or 0.1% DMSO for 24 hrs prior to further assessments.

Figure 2:
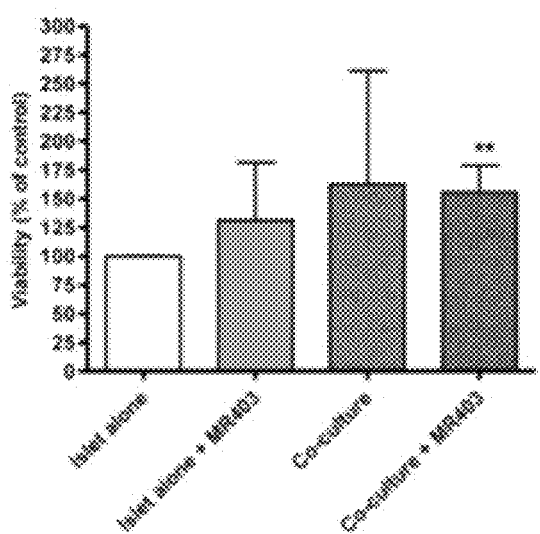
FIG. 2 depicts the effects of GHRH agonist P-27403 on islet viability when cultured alone or when co-cultured with adrenal cells (n=4) in vitro. Islets were cultured either alone or in co-culture with adrenal cells and treated with P-27403 ($10^{-8}$ M) for 24 hrs. Addition of GHRH agonist alone to islets resulted in an increase in viability, and the viability significantly improved (56% compared to control) in co-culture condition and addition of the GHRH agonist. **$p<0.01$ compared to islets alone.

Isolated rat islets and co-cultured islets were treated with P-27403 at a concentration of $10^{-8}$ M or with 0.1% DMSO as control for 24 hrs, and then analyzed for viability. Treatment with P-27403 induced an increase of islet viability of 31%, as compared to control. When co-cultured with adrenal cells alone, islets considerably demonstrated improved viability, and in addition, a significant improvement occurred when GHRH agonist P-27403 was added to the co-culture. With this combination, islet viability improved by 55±23%, as compared to control (FIG. 2).

Example 14

In Vivo Function of Intra-Adrenal Islet Grafts

Figure 3:
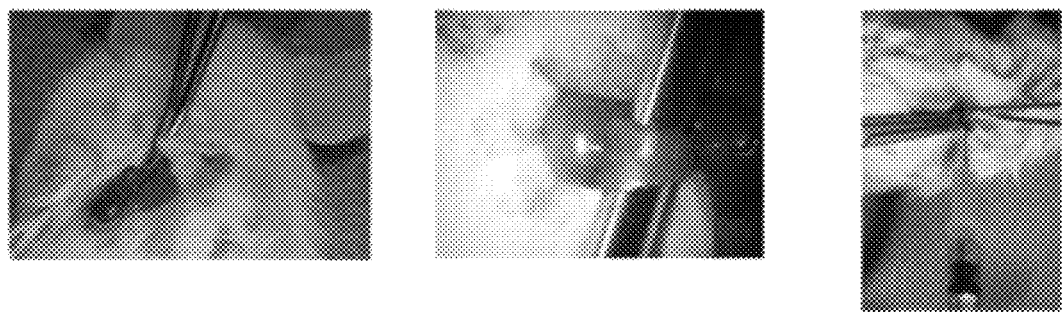
FIG. 3 depicts intra-adrenal transplantation of islets. The left adrenal was carefully exposed (left/middle) and islets in a minimal volume were injected through the upper pole of the gland (right).

NOD-SCID mice were used as islet recipients following guidelines established by the University Institutional Animal Care and Use Committee. Diabetes was induced by single intraperitoneal injection of 180 mg/kg STZ (Sigma). Serum glucose was monitored using a commercial glucometer (AccuChek Aviva, Roche). Animals were considered diabetic if non-fasting blood glucose was >25 mmol/L for at least two consecutive days. For transplantation, isolated rat islets were cultured for 48 hrs and samples of 300 islet equivalents were transplanted underneath the left kidney capsule (n=4) or into the adrenal gland (n=4). For intra-adrenal transplantation, the left adrenal was exposed and the islets concentrated in a total volume of 10 µl were injected directly into the adrenal using a microtiter syringe and a blunted needle (FIG. 3). Blood glucose levels were measured daily throughout the observation period of 35 days. On day 10 an intraperitoneal glucose tolerance test (ipGTT) was performed to challenge the islet grafts. Blood glucose levels were recorded before injection and 15, 30, 45, 60, 90, and 120 min following glucose injection (3 g/kg). The restoration and maintenance of normoglycemia due to islet graft function was verified by removal of the graft-bearing organ on day 30. Animals were then metabolically followed for another 5 days before euthanization. The animal experiments and housing were in accordance with institutional guidelines and German animal regulations.

Figure 4:
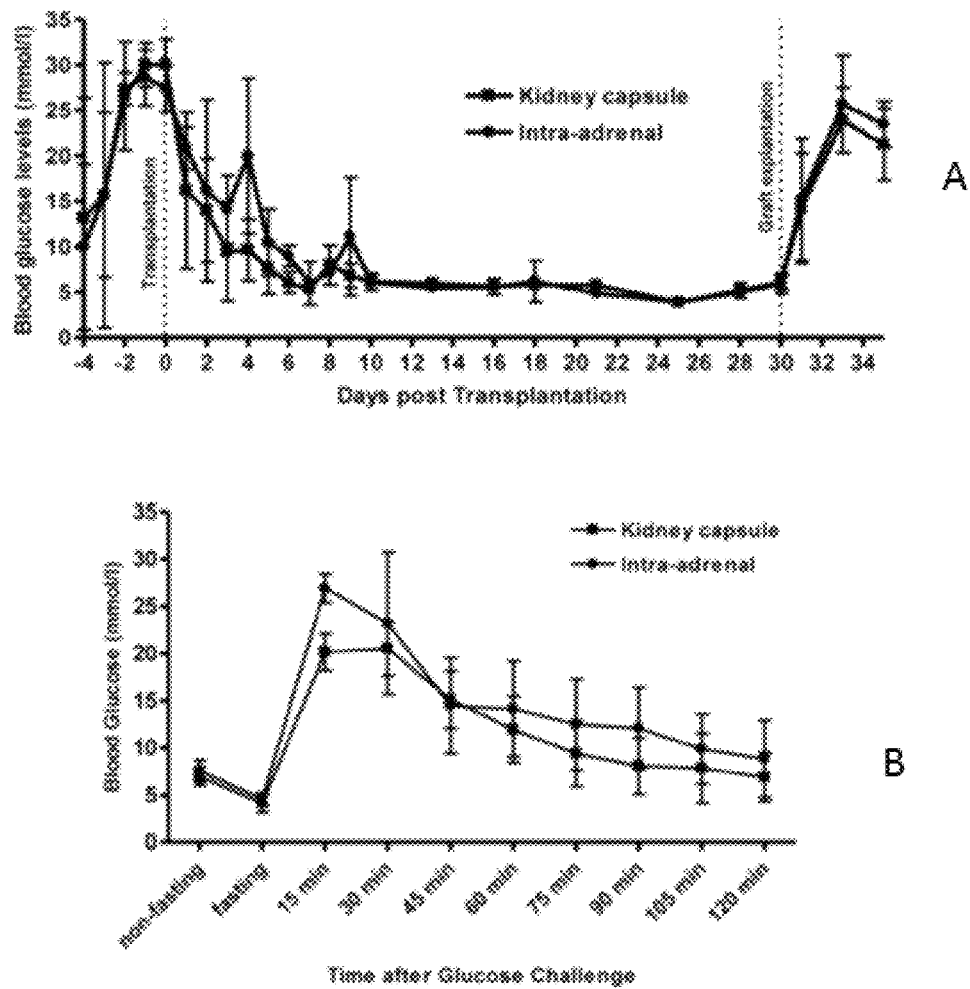
FIG. 4 depicts blood glucose levels in NOD-SCID mice after islet transplantation. (A) NOD-SCID mice with pancreatic islets transplanted in kidney capsule or in adrenal gland were analyzed for blood glucose levels. All animals of both groups showed a rapid and persistent recovery from diabetes upon transplantation. (B) On day 10 following islet transplantation, animals were subjected to an intraperitoneal glucose tolerance test (ipGTT). All animals, irrespective of the transplantation site, were able to revert initial hyperglycemia to normal ranges within 2 hrs.

The procedure of islet transplantation into the adrenal was technically feasible and did not cause any significant bleeding or macroscopically apparent injury of the adrenal tissue. During the procedure, the animals did not show any circulatory disturbance due to adrenal manipulation. All animals showed a rapid decrease in blood glucose levels and reached normoglycemia within a few days after transplantation (FIG. 4A) without any difference between the adrenal transplantation site (n=4) compared to the standard kidney capsule transplantation model (n=4). After removing the islet grafts by unilateral nephrectomy or adrenalectomy respectively, the animals showed an immediate recurrence of hyperglycemia. On day 10 post transplantation, an ipGTT was performed with 3 g/kg body weight of D-glucose. All animals showed a swift increase in blood glucose followed by a rapid normalization to reach target blood glucose levels after two hours (FIG. 4B). The intra-adrenally transplanted animals were not inferior to the standard model regarding blood glucose kinetics.

Figure 5:
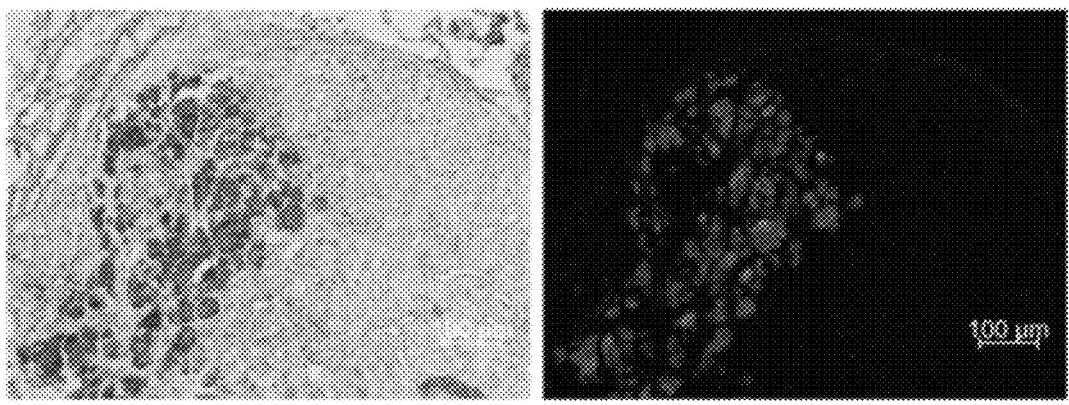
FIG. 5 depicts immunohistochemical analysis of grafted islets in adrenal glands. Serial cryosections of retrieved islet bearing adrenals were stained for insulin (green) to detect pancreatic islets within the adrenal tissue. Sections were co-stained with DAPI for visualization of cell nuclei (blue). Representative image shown by bright field (left) and fluorescent microscopy.
Figure 6:
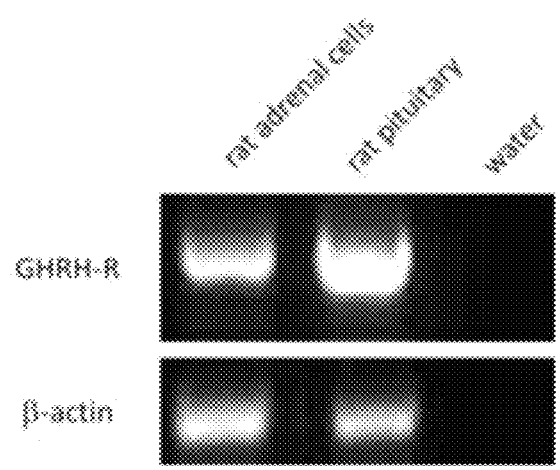
FIG. 6 depicts expression of GHRH receptor in isolated rat adrenal cells by RT-PCR analysis. Rat pituitary was used as positive control and β-actin was used as loading control.

The graft bearing kidneys and adrenals were explanted on day 30 after transplantation and fixed with 4% paraformaldehyde for 10 hrs, stored in 30% sucrose for 24 hrs, embedded in tissue freezing medium, and frozen at $-80°$ C. Immunohistochemical staining was performed on 10 μm cryosections. As primary antibody guinea pig anti-insulin at 1:100 (polyclonal, ab7842; abcam) was used. After washing in PBS with 0.5% Tween, goat anti-guinea pig (Alexa Fluor488, code 106-545-003; Jackson Laboratories) at a concentration of 1:500 was applied as secondary antibody. Immunofluorescence microscopy was performed on Zeiss Axiovert 200M with AxioCamMRc5. Morphologic analysis of the retrieved islet containing adrenal glands showed nearly intact adrenal cell composition with islet clusters integrated mostly in the cortex. No leukocyte infiltration, hemorrhage, signs of necrosis, or apoptotic cells were observed. Immunostaining of insulin revealed intense cytosolic staining and intact islet morphology indicating viability of graft (FIG. 5).

Example 15

Cell Viability Assays

Figure 7:
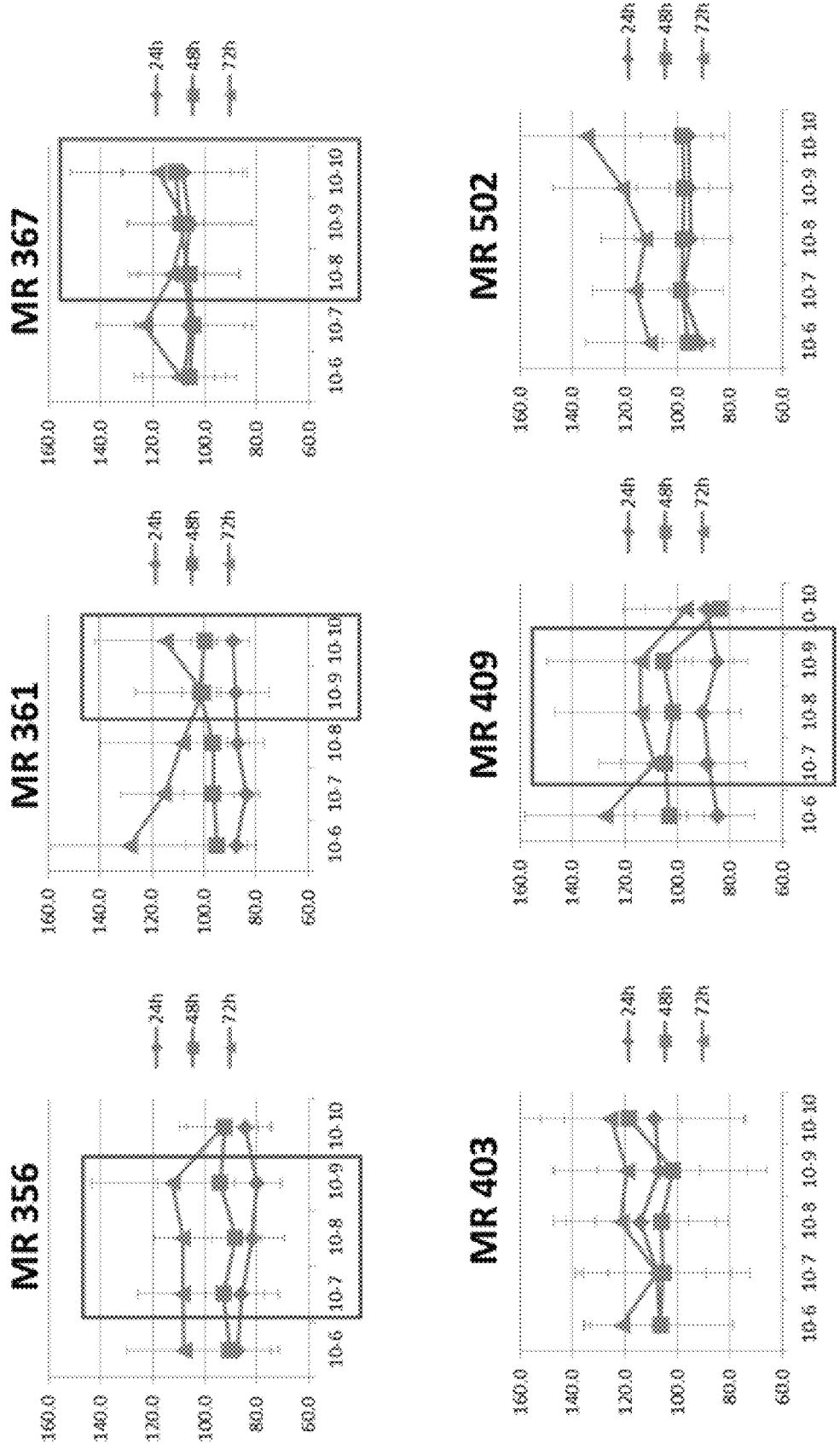
FIG. 7 demonstrates cell viability assay of INS-1 cells after exposure to various GHRH agonist peptides. Values shown are percentage of viable cells when compared to control (DMSO).

INS-1 cells were grown for 72 hours before experimentation. Cells were treated with different GHRH agonist peptides (MR-356/P-20356, MR-361/P-20361, MR-367/P-20367, MR-403/P-27403, MR-409/P-27409, MR-502/P-25502) at different concentrations ($10^{-6}$-$10^{-10}$ M) or with 0.1% (vol/vol) DMSO as control for 24 h, 48 h and 72 h. Viability was assessed using CellTiter 96 AQueous One Solution Cell Proliferation Assay (Promega) according to the manufacturer's instructions. Treatment of INS-1 cells with GHRH agonist peptides for 72 h improved cell viability. Cell viability was expressed as percent of cells treated with control DMSO (FIG. 7).

Example 16

Caspase Assays

Figure 8:
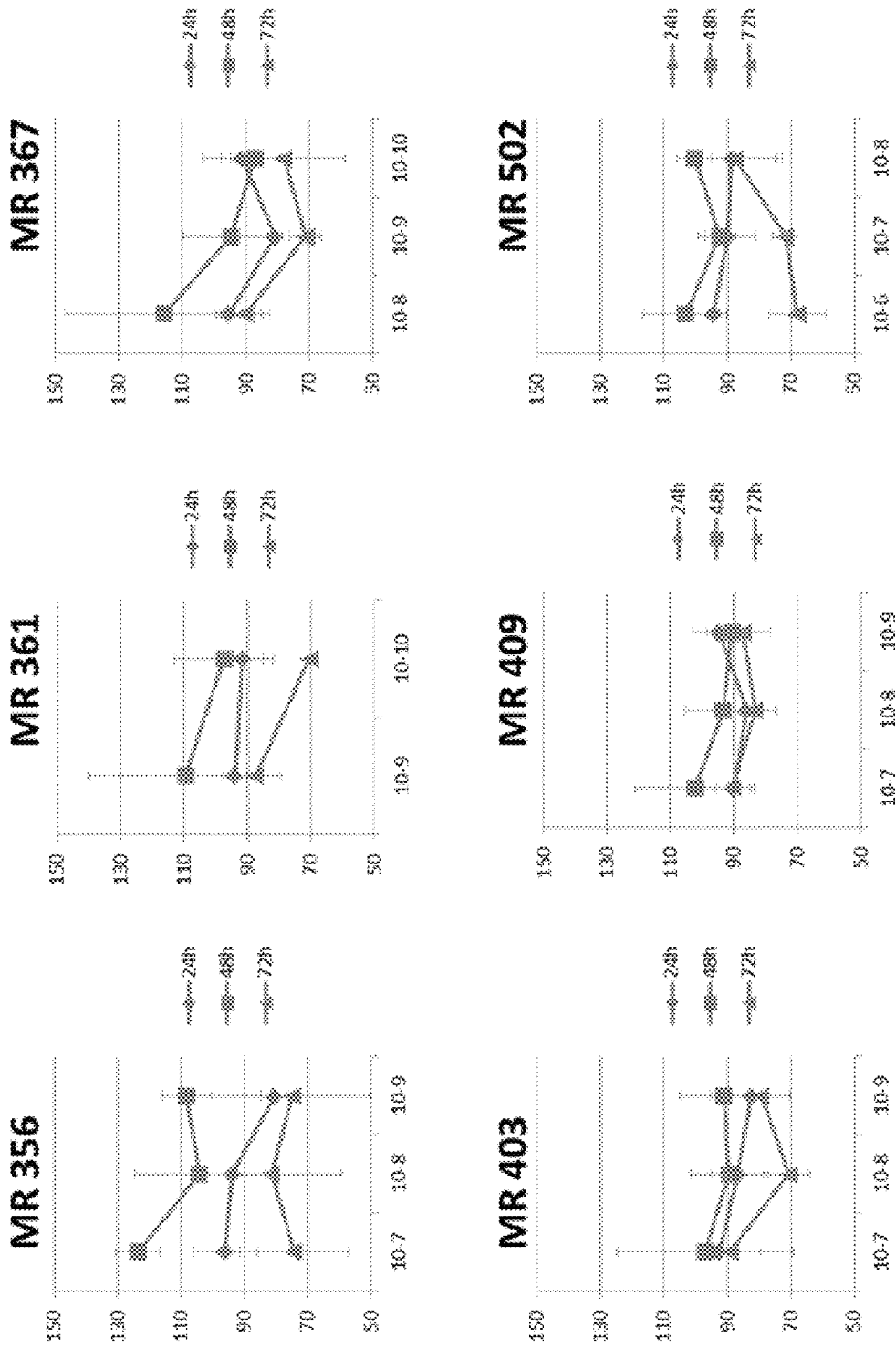
FIG. 8 shows apoptosis of INS-1 cells after exposure to various GHRH agonist peptides. Values shown are percentage of viable cells when compared to control (DMSO).

INS-1 cells were grown for 72 h before experimentation. Cells were treated with various GHRH agonist peptides at different concentrations or with 0.1% (vol/vol) DMSO as control for 24 h, 48 h and 72 h. Apoptosis was assayed by determination of caspase 3/7 activity using Caspase-Glo 3/7 Assay (Promega) according to the manufacturer's instructions. GHRH agonist peptides significantly inhibited apoptosis of INS-1 at 72 h when compared to control (FIG. 8).

Example 17

Cell Proliferation Assays

Figure 9:
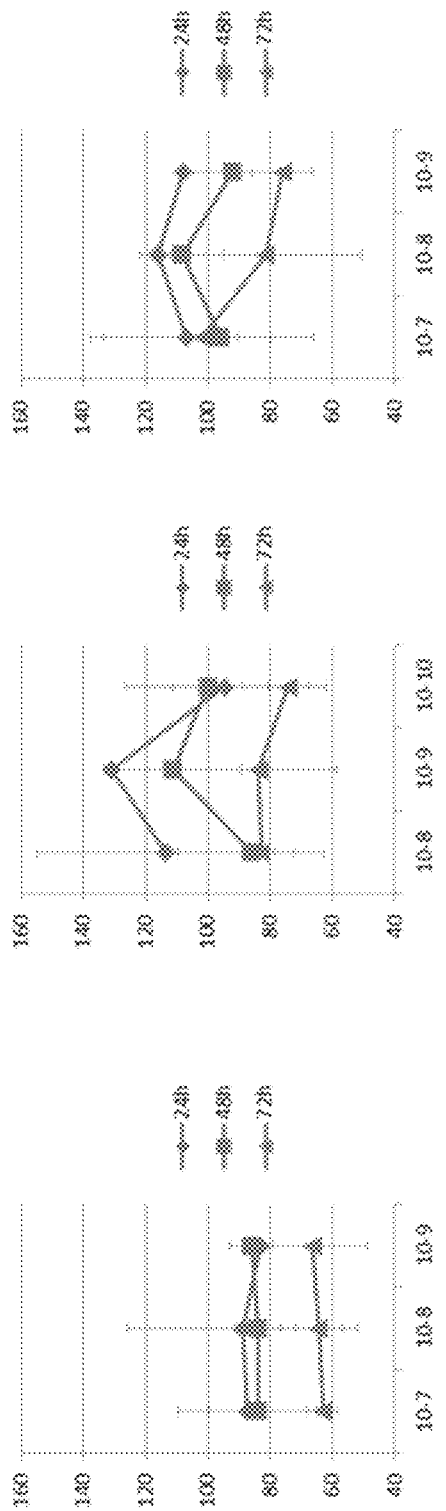
FIG. 9 shows cell proliferation assays of INS-1 cells after exposure to various GHRH agonist peptides. Values shown are percentage of viable cells when compared to control (DMSO).

INS-1 cells were grown for 72 h before experimentation. Cells were treated with GHRH agonists MR356, MR367, and MR403 at different concentrations or with 0.1% (vol/vol) DMSO as control for 24 h, 48 h and 72 h. Proliferation was measured using BrdU Cell Proliferation Assay (Millipore) following the manufacturer's description. MR367 and MR403 significantly induced cell proliferation in INS-1 cells, when compared to control (FIG. 9).

Example 18

Viability Assays in Rat Islets

Figure 10:
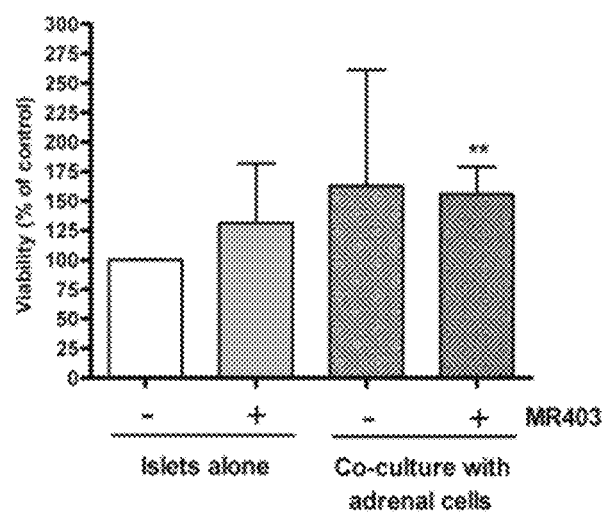
FIG. 10 illustrates in vitro effect of the GHRH agonist MR403 on rat islets [islets alone or islets within the islet-adrenal coculture system (n=4)].

Islets were cultured either alone or in coculture with adrenal cells (n=4) and treated with GHRH agonist MR403 ($10^{-8}$ M) for 24 h. Addition of GHRH agonist to islets alone resulted in an increase of viability, and further significant improvement was seen in coculture conditions (56% compared with control) (FIG. 10). **$P<0.01$ compared with islets alone.

What is claimed is:

1. A method of treating a patient diagnosed with diabetes comprising:

transplanting a tissue comprising islet cells into a patient; and administering a therapeutically effective amount of a GHRH agonist peptide to the patient, wherein the GHRH agonist peptide is selected from the group having the formula:

P-20103 [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29)(SEQ ID NO: 2);

P-20105 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29);

P-20107 [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGHRH(1-29)(SEQ ID NO: 3);

P-20109 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$] hGHRH(1-29);

P-20110 [N—Me-Tyr$^1$, D-Ala$^2$, Fpa5$^6$, Orn$^{12}$, Abu$^{15}$, Orn$^{21}$, Nle$^{27}$, Agm$^{29}$] hGHRH(1-29);

P-20111 [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29);

P-20113 [N—Me-Tyr$^1$, Fpa5$^6$, Orn$^{12}$, Abu$^{15}$, Orn$^{21}$, Nle$^{27}$, Asp$^{28}$, Agm$^{29}$] hGHRH(1-29)(SEQ ID NO: 4);

P-20115 [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH (1-29)(SEQ ID NO: 5);

P-20117 [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH (1-29);

P-20350 [Dat$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29);

P-20351 [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29);

P-20356 [N—Me-Tyr$^1$, Gln$^8$, Orn$^{12}$, Abu$^{15}$, Orn$^{21}$, Nle$^{27}$, Asp$^{28}$, Agm$^{29}$] hGHRH(1-29)(SEQ ID NO: 6);

P-20357 [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29);

P-20358 [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29);

P-20359 [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH (1-29);

P-20360 [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGHRH (1-29);

P-20361 [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH (1-29);

P-20367 [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29);

P-20370 [N—Me-Tyr$^1$, Orn$^{12}$, Abu$^{15}$, Orn$^{21}$, Nle$^{27}$, Asp$^{28}$, Agm$^{29}$]hGHRH (1-29)(SEQ ID NO: 7);

P-20371 [N—Me-Tyr$^1$, Thr$^8$, Orn$^{12}$, Abu$^{15}$, Orn$^{21}$, Nle$^{27}$, Asp$^{28}$, Agm$^{29}$] hGHRH(1-29)(SEQ ID NO: 8);

P-20372 [N—Me-Tyr$^1$, Ala$^8$, Orn$^{12}$, Abu$^{15}$, Orn$^{21}$, Nle$^{27}$, Asp$^{28}$, Agm$^{29}$] hGHRH(1-29)(SEQ ID NO: 9);

P-20373 [N—Me-Tyr$^1$, Gln$^8$, Orn$^{12}$, Abu$^{15}$, Orn$^{21}$, Nle$^{27}$, Agm$^{29}$]hGHRH (1-29)(SEQ ID NO: 10);

P-20374 [N—Me-Tyr$^1$, Orn$^{12}$, Abu$^{15}$, Orn$^{21}$, Nle$^{27}$, Agm$^{29}$]hGHRH(1-29) (SEQ ID NO: 11);

P-20375 [N—Me-Tyr$^1$, Thr$^8$, Orn$^{12}$, Abu$^{15}$, Orn$^{21}$, Nle$^{27}$, Agm$^{29}$]hGHRH (1-29)(SEQ ID NO: 12);

P-20376 [N—Me-Tyr$^1$, Ala$^8$, Orn$^{12}$, Abu$^{15}$, Orn$^{21}$, Nle$^{27}$, Agm$^{29}$]hGHRH (1-29)(SEQ ID NO: 13);

P-21300 [Dat$^1$, D-Ala$^2$, Orn$^{12}$, Abu$^{15}$, Orn$^{21}$, Nle$^{27}$, Asp$^{28}$, Amc$^{30}$]hGHRH (1-30)NH$_2$;

P-21301 [N—Me-Tyr$^1$, Orn$^{12}$, Abu$^{15}$, Orn$^{21}$, Nle$^{27}$, Asp$^{28}$, Amc$^{30}$]hGHRH (1-30)NH$_2$(SEQ ID NO: 14);

P-21303 [N—Me-Tyr$^1$, D-Ala$^2$, Orn$^{12}$, Abu$^{15}$, Orn$^{21}$, Nle$^{27}$, Asp$^{28}$, Amc$^{30}$] hGHRH(1-30)NH$_2$;

P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$] hGHRH(1-30)NH$_2$;

P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;
P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$;
P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGHRH(1-30)NH$_2$;
P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;
P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;
P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGHRH (1-30)NH$_2$(SEQ ID NO: 15);
P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22327 [Dat$^1$, Gln$^8$, Orn$^{12}$, Abu$^{15}$, Orn$^{21}$, Nle$^{27}$, Asp$^{28}$, Apa$^{30}$]hGHRH (1-30)NH$_2$(SEQ ID NO: 16);
P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22329 [N—Me-Tyr$^1$, D-Ala$^2$, Orn$^{12}$, Abu$^{15}$, Orn$^{21}$, Nle$^{27}$, Apa$^{30}$]hGHRH(1-30)NH$_2$;
P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$;
P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$;
P-22332 [N—Me-Tyr$^1$, Orn$^{12}$, Abu$^{15}$, Orn$^{21}$, Nle$^{27}$, Asp$^{28}$, Apa$^{30}$]hGHRH (1-30)NH$_2$ (SEQ ID NO: 17);
P-22334 [N—Me-Tyr$^1$, Orn$^{12}$, Abu$^{15}$, Orn$^{21}$, Nle$^{27}$, Apa$^{30}$]hGHRH(1-30)NH$_2$ (SEQ ID NO: 18);
P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 19);
P-22336 [N—Me-Tyr$^1$ Ala$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 20);
P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23251 [Dat$^1$, Gln$^8$, Orn$^{12}$, Abu$^{15}$, Orn$^{21}$, Nle$^{27}$, Asp$^{28}$, Har$^{30}$]hGHRH (1-30)NH$_2$ (SEQ ID NO: 21);
P-23252 [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23253 [Dat$^1$, Orn$^{12}$, Abu$^{15}$, Orn$^{21}$, Nle$^{27}$, Asp$^{28}$, Har$^{30}$]hGHRH(1-30)NH$_2$ (SEQ ID NO: 22);
P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23255 [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 23);
P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23257 [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 24);
P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23259 [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 25);
P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23261 [N—Me-Tyr$^1$, Orn$^{12}$, Abu$^{15}$, Orn$^{21}$, Nle$^{27}$, Asp$^{28}$, Har$^{30}$]hGHRH (1-30)NH$_2$ (SEQ ID NO: 26);
P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 27);
P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23265 [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 28);
P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$ (SEQ ID NO: 29);
P-24341 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;
P-24342 [Dat$^1$, Gln$^8$, Orn$^{12}$, Abu$^{15}$, Orn$^{21}$, Nle$^{27}$, Asp$^{28}$, Aha$^{30}$]hGHRH (1-30)NH$_2$ (SEQ ID NO: 30);
P-24344 [Dat$^1$-D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;
P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$;
P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;
P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;
P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;
P-25501 [N—Me-Tyr$^1$, D-Ala$^2$, Orn$^{12}$, Abu$^{15}$, Orn$^{21}$, Nle$^{27}$, Gab$^{30}$]hGHRH (1-30)NH$_2$;
P-25502 [Dat$^1$, D-Ala$^2$, Fpa$^6$, Orn$^{12}$, Abu$^{15}$, Orn$^{21}$, Nle$^{27}$, Gab$^{30}$]hGHRH (1-30)NH$_2$;
P-25503 [N—Me-Tyr$^1$, Abu$^2$, Orn$^{12}$, Abu$^{15}$, Orn$^{21}$, Nle$^{27}$, Gab$^{30}$]hGHRH (1-30)NH$_2$ (SEQ ID NO: 31);
P-25504 [Dat$^1$, D-Abu$^2$, Orn$^{12}$, Abu$^{15}$, Orn$^{21}$, Nle$^{27}$, Gab$^{30}$]hGHRH (1-30)NH$_2$;
P-25506 [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$;
P-25508 [Tfa-Tyr$^1$, D-Ala$^2$, Orn$^{12}$, Abu$^{15}$, Orn$^{21}$, Nle$^{27}$, Gab$^{30}$]hGHRH (1-30)NH$_2$;
P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$;
P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$;
P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;
P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$;
P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;
P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27404 [N—Me-Tyr$^1$, D-Ala$^2$, Fpa$^6$, Orn$^{12}$, Abu$^{15}$, Orn$^{21}$, Nle$^{27}$, Asp$^{28}$]hGHRH(1-29)NH—CH$_3$;
P-27405 [N—Me-Tyr$^1$, Gln$^8$, Orn$^{12}$, Abu$^{15}$, Orn$^{21}$, Nle$^{27}$]hGHRH(1-29)NH—CH$_3$ (SEQ ID NO: 32);
P-27406 [N—Me-Tyr$^1$, Gln$^8$, Orn$^{12}$, Abu$^{15}$, Orn$^{21}$, Nle$^{27}$, Asp$^{28}$]hGHRH (1-29)NH—CH$_3$ (SEQ ID NO: 33);
P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 34);
P-27408 [Dat$^1$, D-Ala$^2$, Gln$^8$, Orn$^{12}$, Abu$^{15}$, Orn$^{21}$, Nle$^{27}$, Asp$^{28}$]hGHRH (1-30)NH—CH$_3$;
P-27409 [N—Me-Tyr$^1$, D-Ala$^2$, Orn$^{12}$, Abu$^{15}$, Orn$^{21}$, Nle$^{27}$, Asp$^{28}$]hGHRH (1-29)NH—CH$_3$;
P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;
P-27411 [N—Me-Tyr$^1$, D-Ala$^2$, Thr$^8$, Orn$^{12}$, Abu$^{15}$, Orn$^{21}$, Nle$^{27}$]hGHRH (1-29)NH—CH$_3$;
P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;
P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$ (SEQ ID NO: 35);
P-27414 [N—Me-Tyr$^1$, D-Ala$^2$, Fpa$^6$, Orn$^{12}$, Abu$^{15}$, Orn$^{21}$, Nle$^{27}$, Gab$^{30}$]hGHRH(1-30)NH—CH$_3$;
P-27415 [N—Me-Tyr$^1$, Orn$^{12}$, Abu$^{15}$, Orn$^{21}$, Nle$^{27}$, Gab$^{30}$]hGHRH(1-30)NH—CH$_3$ (SEQ ID NO: 36);
P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;
P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27418 [Ac-Tyr$^1$, D-Ala$^2$, Fpa$^6$, Orn$^{12}$, Abu$^{15}$, Orn$^{21}$, Nle$^{27}$, Asp$^{28}$]hGHRH(1-29)NH—CH$_3$;
P-27419 [Ac-Tyr$^1$, Thr$^8$, Orn$^{12}$, Abu$^{15}$, Orn$^{21}$, Nle$^{27}$]hGHRH(1-29)NH—CH$_3$ (SEQ ID NO: 37);
P-27422 [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$;
P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;
P-27424 [Dat$^1$, Thr$^8$, Orn$^{12}$, Abu$^{15}$, Orn$^{21}$, Nle$^{27}$]hGHRH(1-29)NH—CH$_3$ (SEQ ID NO: 38);
P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27442 [N—Me-Tyr¹, D-Ala², Fpa5⁶, Orn¹², Abu¹⁵, Orn²¹, Nle²⁷, Asp²⁸, D-Arg²⁹]hGHRH(1-29)NH—CH₃;
P-27443 [N—Me-Tyr¹, Orn¹², Abu¹⁵, Orn²¹, Nle²⁷, D-Arg²⁹]hGHRH(1-29)NH—CH₃;
P-27444 [N—Me-Tyr¹, D-Ala², Orn¹², Abu¹⁵, Orn²¹, Nle²⁷, Asp²⁸, D-Arg²⁹]hGHRH(1-29)NH—CH₃;
P-27445 [N—Me-Tyr¹, D-Ala², Thr⁸, Orn¹², Abu¹⁵, Orn²¹, Nle²⁷, Asp²⁸, D-Arg²⁹]hGHRH(1-29)NH—CH₃;
P-27446 [N—Me-Tyr¹, D-Ala², Ala⁸, Orn¹², Abu¹⁵, Orn²¹, Nle²⁷, Asp²⁸, D-Arg²⁹]hGHRH(1-29)NH—CH₃;
P-27447 [N—Me-Tyr¹, D-Ala², Gln⁸, Orn¹², Abu¹⁵, Orn²¹, Nle²⁷, Asp²⁸, Apa³⁰]hGHRH(1-30)NH—CH₃;
P-27448 [N—Me-Tyr¹, D-Ala², Gln⁸, Orn¹², Abu¹⁵, Orn²¹, Nle²⁷, Asp²⁸, Aha³⁰]hGHRH(1-30)NH—CH₃;
P-27449 [N—Me-Tyr¹, D-Ala², Gln⁸, Orn¹², Abu¹⁵, Orn²¹, Nle²⁷, Asp²⁸, Amc³⁰]hGHRH(1-30)NH—CH₃;
P-27450 [N—Me-Tyr¹, D-Ala², Gln⁸, Orn¹², Abu¹⁵, Orn²¹, Nle²⁷, Asp²⁸, Har³⁰]hGHRH(1-30)NH—CH₃;
P-27451 [N—Me-Tyr¹, D-Ala², Gln⁸, His¹¹, Orn¹², Abu¹⁵, His²⁰, Orn²¹, Nle²⁷, Asp²⁸, Apa³⁰]hGHRH(1-30)NH—CH₃;
P-28420 [N—Me-Tyr¹, D-Ala², Gln⁸, Orn¹², Abu¹⁵, Orn²¹, Nle²⁷, Asp²⁸]hGHRH(1-29)NH—CH₂—CH₃;
P-28421 [N—Me-Tyr¹, D-Ala², Orn¹², Abu¹⁵, Orn²¹, Nle²⁷, Asp²⁸]hGHRH(1-29)NH—CH₂—CH₃;
P-28430 [N—Me-Tyr¹, D-Ala², Gln⁸, Orn¹², Abu¹⁵, Orn²¹, Nle²⁷]hGHRH(1-29)NH—CH₂—CH₃;
P-28431 [N—Me-Tyr¹, D-Ala², Thr⁸, Orn¹², Abu¹⁵, Orn²¹, Nle²⁷, Asp²⁸]hGHRH(1-29)NH—CH₂—CH₃;
P-28460 [N—Me-Tyr¹, D-Ala², Fpa5⁶, Gln⁸, Orn¹², Abu¹⁵, Orn²¹, Nle²⁷, Asp²⁸]hGHRH(1-29)NH—CH₂—CH₃;
P-28461 [N—Me-Tyr¹, D-Ala², Gln⁸, Orn¹², Abu¹⁵, Orn²¹, Nle²⁷]hGHRH(1-29)NH—CH₂—CH₃;
P-28462 [N—Me-Tyr¹, D-Ala², Fpa5⁶, Orn¹², Abu¹⁵, Orn²¹, Nle²⁷]hGHRH(1-29)NH—CH₂—CH₃;
P-28463 [N—Me-Tyr¹, D-Ala², Orn¹², Abu¹⁵, Orn²¹, Nle²⁷]hGHRH(1-29)NH—CH₂—CH₃;
P-28464 [N—Me-Tyr¹, D-Ala², Fpa5⁶, Gln⁸, Orn¹², Abu¹⁵, Orn²¹, Nle²⁷]hGHRH(1-29)NH—CH₂—CH₃;
P-28465 [N—Me-Tyr¹, D-Ala², Gln⁸, Orn¹², Abu¹⁵, Orn²¹, Nle²⁷, Asp²⁸]hGHRH(1-29)NH—CH₂—CH₃;
P-28466 [N—Me-Tyr¹, D-Ala², Fpa5⁶, Orn¹², Abu¹⁵, Orn²¹, Nle²⁷, Asp²⁸]hGHRH(1-29)NH—CH₂—CH₃;
P-28467 [N—Me-Tyr¹, D-Ala², Orn¹², Abu¹⁵, Orn²¹, Nle²⁷, Asp²⁸]hGHRH(1-29)NH—CH₂—CH₃;
P-28468 [N—Me-Tyr¹, D-Ala², Fpa5⁶, Gln⁸, Orn¹², Abu¹⁵, Orn²¹, Nle²⁷, Asp²⁸]hGHRH(1-29)NH—CH₂—CH₃;
P-28469 [Dat¹, D-Ala², Gln⁸, Orn¹², Abu¹⁵, Orn²¹, Nle²⁷]hGHRH(1-29)NH—CH₂—CH₃;
P-28470 [Dat¹, D-Ala², Orn¹², Abu¹⁵, Orn²¹, Nle²⁷]hGHRH(1-29)NH—CH₂—CH₃;
P-28471 [Dat¹, D-Ala², Gln⁸, Orn¹², Abu¹⁵, Orn²¹, Nle²⁷, Asp²⁸]hGHRH(1-29)NH—CH₂—CH₃;
P-28472 [Dat¹, D-Ala², Fpa5⁶, Gln⁸, Orn¹², Abu¹⁵, Orn²¹, Nle²⁷, Asp²⁸]hGHRH(1-29)NH—CH₂—CH₃;
P-28473 [Dat¹, D-Ala², Fpa5⁶, Orn¹², Abu¹⁵, Orn²¹, Nle²⁷, Asp²⁸]hGHRH(1-29)NH—CH₂—CH₃;
P-28474 [Dat¹, D-Ala², Orn¹², Abu¹⁵, Orn²¹, Nle²⁷, Asp²⁸]hGHRH(1-29)NH—CH₂—CH₃;
P-28475 [N—Me-Tyr¹, D-Ala², Gln⁸, Orn¹², Abu¹⁵, Orn²¹, Nle²⁷, Asp²⁸, Apa³⁰]hGHRH(1-30)NH—CH₂—CH₃;
P-28476 [N—Me-Tyr¹, D-Ala², Gln⁸, Orn¹², Abu¹⁵, Orn²¹, Nle²⁷, Asp²⁸, Aha³⁰]hGHRH(1-30)NH—CH₂—CH₃;
P-28477 [N—Me-Tyr¹, D-Ala², Gln⁸, Orn¹², Abu¹⁵, Orn²¹, Nle²⁷, Asp²⁸, Amc³⁰]hGHRH(1-30)NH—CH₂—CH₃;
P-28478 [N—Me-Tyr¹, D-Ala², Gln⁸, Orn¹², Abu¹⁵, Orn²¹, Nle²⁷, Asp²⁸, Har³⁰]hGHRH(1-30)NH—CH₂—CH₃;
P-28479 [N—Me-Tyr¹, D-Ala², Gln⁸, His¹¹, Orn¹², Abu¹⁵, His²⁰, Orn²¹, Nle²⁷, Asp²⁸, Apa³⁰]hGHRH(1-30)NH—CH₂—CH₃;
P-29701 [N—Me-Tyr¹, D-Ala², Gln⁸, Orn¹², Abu¹⁵, Orn²¹, Nle²⁷, Asp²⁸, Gln-Gab³⁰] hGHRH](1-30)NH₂;
P-29702 [Dat¹, D-Ala², Orn¹², Abu¹⁵, Orn²¹, Nle²⁷, Gln-Gab³⁰]hGHRH(1-30)NH₂;
P-29703 [N—Me-Tyr¹, Gln⁸, Orn¹², Abu¹⁵, Orn²¹, Nle²⁷, Gln-Gab³⁰]hGHRH(1-30)NH₂(SEQ ID NO: 39);
P-29704 [Dat¹, D-Ala², Gln⁸, Orn¹², Abu¹⁵, Orn²¹,²², Nle²⁷, Gln-Gab³⁰]hGHRH(1-30)NH₂;
P-29706 [Tfa-Tyr¹, D-Abu², Gln⁸, Orn¹², Abu¹⁵, Orn²¹, Nle²⁷, Gln-Gab³⁰]hGHRH(1-30)NH₂;
P-29708 [N—Me-Tyr¹, D-Ala², Fpa5⁶, Orn¹², Abu¹⁵, Orn²¹, Nle²⁷, Gln-Gab³⁰]hGHRH(1-30)NH₂;
P-29710 [N—Me-Tyr¹, D-Ala², Fpa5⁶, Ala⁸, Orn¹², Abu¹⁵, Orn²¹, Nle²⁷, Gln-Gab³⁰]hGHRH(1-30)NH₂;
P-29720 [Dat¹, D-Ala², Orn¹², Abu¹⁵, Orn²¹, Nle²⁷, Asp²⁸, Gln-Gab³⁰]hGHRH(1-30)NH₂;
P-29721 [Dat¹, D-Ala², Gln⁸, Orn¹², Abu¹⁵, Orn²¹,²², Nle²⁷, Asp²⁸, Gln-Gab³⁰]hGHRH(1-30)NH₂;
P-29722 [Tfa-Tyr¹, D-Abu², Gln⁸, Orn¹², Abu¹⁵, Orn²¹, Nle²⁷, Asp²⁸, Gln³⁰, Gab³¹]hGHRH(1-30)NH₂;
P-29723 [N—Me-Tyr¹, D-Ala², Fpa5⁶, Orn¹², Abu¹⁵, Orn²¹, Nle²⁷, Asp²⁸, Gln-Gab³⁰] hGHRH(1-30)NH₂; and
P-29724 [N—Me-Tyr¹, D-Ala², Fpa5⁶, Ala⁸, Orn¹², Abu¹⁵, Orn²¹, Nle²⁷, Asp²⁸, Gln-Gab³⁰]hGHRH(1-30)NH₂, and pharmaceutically acceptable salts thereof.

2. The method of claim 1, wherein GHRH agonist peptide is selected from the group having the formula:

P-20367 [N—Me-Tyr¹, D-Ala², Orn¹², Abu¹⁵, Orn²¹, Nle²⁷, Asp²⁸, Agm²⁹]hGHRH(1-29);
P-20361 [N—Me-Tyr¹, D-Ala², Gln⁸, Orn¹², Abu¹⁵, Orn²¹, Nle²⁷, Asp²⁸, Agm²⁹]hGHRH(1-29);
P-27406 [N—Me-Tyr¹, Gln⁸, Orn¹², Abu¹⁵, Orn²¹, Nle²⁷, Asp²⁸]hGHRH(1-29) NH—CH₃ (SEQ ID NO: 33);
P-28420 [N—Me-Tyr¹, D-Ala², Gln⁸, Orn¹², Abu¹⁵, Orn²¹, Nle²⁷, Asp²⁸]hGHRH(1-29)NH—CH₂—CH₃;
P-28421 [N—Me-Tyr¹, D-Ala², Orn¹², Abu¹⁵, Orn²¹, Nle²⁷, Asp²⁸]hGHRH(1-29) NH—CH₂—CH₃;
P-27403 [N—Me-Tyr¹, D-Ala², Gln⁸, Orn¹², Abu¹⁵, Orn²¹, Nle²⁷, Asp²⁸]hGHRH(1-29)NH—CH₃;
P-27409 [N—Me-Tyr¹, D-Ala², Orn¹², Abu¹⁵, Orn²¹, Nle²⁷, Asp²⁸]hGHRH(1-29)NH—CH₃;
P-20356 [N—Me-Tyr¹, Gln⁸, Orn¹², Abu¹⁵, Orn²¹, Nle²⁷, Asp²⁸, Agm²⁹]hGHRH(1-29)(SEQ ID NO: 6); and
P-25502 [Dat¹, D-Ala², Fpa5⁶, Orn¹², Abu¹⁵, Orn²¹, Nle²⁷, Gab³⁰]hGHRH(1-30)NH₂.

3. The method of claim 1, wherein the GHRH agonist peptide is:

P-27403 [N—Me-Tyr¹, D-Ala², Gln⁸, Orn¹², Abu¹⁵, Orn²¹, Nle²⁷, Asp²⁸]hGHRH(1-29)NH—CH₃.

4. The method of claim 1, wherein the GHRH agonist peptide is:

P-27409 [N—Me-Tyr¹, D-Ala², Orn¹², Abu¹⁵, Orn²¹, Nle²⁷, Asp²⁸]hGHRH(1-29)NH—CH₃.

5. The method of claim 1, wherein the GHRH agonist peptide is:

P-20356 [N—Me-Tyr¹, Gln⁸, Orn¹², Abu¹⁵, Orn²¹, Nle²⁷, Asp²⁸, Agm²⁹]hGHRH(1-29)(SEQ ID NO: 6).

6. The method of claim 1, wherein the GHRH agonist peptide is:

P-25502 [Dat¹, D-Ala², Fpa5⁶, Orn¹², Abu¹⁵, Orn²¹, Nle²⁷, Gab³⁰]hGHRH(1-30)NH₂.

7. A method of promoting survival of grafted tissue, the method comprising exposing the tissue to an effective amount of a GHRH agonist peptide, wherein the GHRH agonist peptide is selected from the peptides having the formula:

P-20103 [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29)(SEQ ID NO: 2);

P-20105 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29);

P-20107 [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGHRH(1-29)(SEQ ID NO: 3);

P-20109 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$] hGHRH(1-29);

P-20110 [N—Me-Tyr$^1$, D-Ala$^2$, Fpa5$^6$, Orn$^{12}$, Abu$^{15}$, Orn$^{21}$, Nle$^{27}$, Agm$^{29}$] hGHRH(1-29);

P-20111 [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29);

P-20113 [N—Me-Tyr$^1$, Fpa5$^6$, Orn$^{12}$, Abu$^{15}$, Orn$^{21}$, Nle$^{27}$, Asp$^{28}$, Agm$^{29}$] hGHRH(1-29)(SEQ ID NO: 4);

P-20115 [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH (1-29)(SEQ ID NO: 5);

P-20117 [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH (1-29);

P-20350 [Dat$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29);

P-20351 [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$] hGHRH(1-29);

P-20356 [N—Me-Tyr$^1$, Gln$^8$, Orn$^{12}$, Abu$^{15}$, Orn$^{21}$, Nle$^{27}$, Asp$^{28}$, Agm$^{29}$] hGHRH(1-29)(SEQ ID NO: 6);

P-20357 [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29);

P-20358 [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29);

P-20359 [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH (1-29);

P-20360 [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGHRH (1-29);

P-20361 [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH (1-29);

P-20367 [N—Me-Tyr$^1$, D-Ala$^2$, Orn$^{12}$, Abu$^{15}$, Orn$^{21}$, Nle$^{27}$, Asp$^{28}$, Agm$^{29}$] hGHRH(1-29);

P-20370 [N—Me-Tyr$^1$, Orn$^{12}$, Abu$^{15}$, Orn$^{21}$, Nle$^{27}$, Asp$^{28}$, Agm$^{29}$]hGHRH (1-29)(SEQ ID NO: 7);

P-20371 [N—Me-Tyr$^1$, Thr$^8$, Orn$^{12}$, Abu$^{15}$, Orn$^{21}$, Nle$^{27}$, Asp$^{28}$, Agm$^{29}$] hGHRH(1-29)(SEQ ID NO: 8);

P-20372 [N—Me-Tyr$^1$, Ala$^8$, Orn$^{12}$, Abu$^{15}$, Orn$^{21}$, Nle$^{27}$, Asp$^{28}$, Agm$^{29}$] hGHRH(1-29)(SEQ ID NO: 9);

P-20373 [N—Me-Tyr$^1$, Gln$^8$, Orn$^{12}$, Abu$^{15}$, Orn$^{21}$, Nle$^{27}$, Agm$^{29}$]hGHRH (1-29)(SEQ ID NO: 10);

P-20374 [N—Me-Tyr$^1$, Orn$^{12}$, Abu$^{15}$, Orn$^{21}$, Nle$^{27}$, Agm$^{29}$]hGHRH(1-29) (SEQ ID NO: 11);

P-20375 [N—Me-Tyr$^1$, Thr$^8$, Orn$^{12}$, Abu$^{15}$, Orn$^{21}$, Nle$^{27}$, Agm$^{29}$]hGHRH (1-29)(SEQ ID NO: 12);

P-20376 [N—Me-Tyr$^1$, Ala$^8$, Orn$^{12}$, Abu$^{15}$, Orn$^{21}$, Nle$^{27}$, Agm$^{29}$]hGHRH (1-29)(SEQ ID NO: 13);

P-21300 [Dat$^1$, D-Ala$^2$, Orn$^{12}$, Abu$^{15}$, Orn$^{21}$, Nle$^{27}$, Asp$^{28}$, Amc$^{30}$]hGHRH (1-30)NH$_2$;

P-21301 [N—Me-Tyr$^1$, Orn$^{12}$, Abu$^{15}$, Orn$^{21}$, Nle$^{27}$, Asp$^{28}$, Amc$^{30}$]hGHRH (1-30)NH$_2$(SEQ ID NO: 14);

P-21303 [N—Me-Tyr$^1$, D-Ala$^2$, Orn$^{12}$, Abu$^{15}$, Orn$^{21}$, Nle$^{27}$, Asp$^{28}$, Amc$^{30}$] hGHRH(1-30)NH$_2$;

P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$] hGHRH(1-30)NH$_2$;

P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;

P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$] hGHRH(1-30)NH$_2$;

P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;

P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$] hGHRH(1-30)NH$_2$;

P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGHRH(1-30)NH$_2$;

P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;

P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;

P-22325 [N—Me-Tyr$^1$, Gln$^8$, Orn$^{12}$, Abu$^{15}$, Orn$^{21}$, Nle$^{27}$, Asp$^{28}$, Apa$^{30}$] hGHRH (1-30)NH$_2$(SEQ ID NO: 15);

P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;

P-22327 [Dat$^1$, Gln$^8$, Orn$^{12}$, Abu$^{15}$, Orn$^{21}$, Nle$^{27}$, Asp$^{28}$, Apa$^{30}$]hGHRH (1-30)NH$_2$(SEQ ID NO: 16);

P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$] hGHRH(1-30)NH$_2$;

P-22329 [N—Me-Tyr$^1$, D-Ala$^2$, Orn$^{12}$, Abu$^{15}$, Orn$^{21}$, Nle$^{27}$, Apa$^{30}$]hGHRH (1-30)NH$_2$;

P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$;

P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$;

P-22332 [N—Me-Tyr$^1$, Orn$^{12}$, Abu$^{15}$, Orn$^{21}$, Nle$^{27}$, Asp$^{28}$, Apa$^{30}$]hGHRH (1-30)NH$_2$ (SEQ ID NO: 17);

P-22334 [N—Me-Tyr$^1$, Orn$^{12}$, Abu$^{15}$, Orn$^{21}$, Nle$^{27}$, Apa$^{30}$]hGHRH(1-30) NH$_2$ (SEQ ID NO: 18);

P-22335 [N—Me-Tyr$^1$, Thr$^8$, Orn$^{12}$, Abu$^{15}$, Orn$^{21}$, Nle$^{27}$, Asp$^{28}$, Apa$^{30}$] hGHRH(1-30)NH$_2$ (SEQ ID NO: 19);

P-22336 [N—Me-Tyr$^1$ Ala$^8$, Orn$^{12}$, Abu$^{15}$, Orn$^{21}$, Nle$^{27}$, Asp$^{28}$, Apa$^{30}$] hGHRH(1-30)NH$_2$ (SEQ ID NO: 20);

P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGHRH(1-30)NH$_2$;

P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$] hGHRH(1-30)NH$_2$;

P-23251 [Dat$^1$, Gln$^8$, Orn$^{12}$, Abu$^{15}$, Orn$^{21}$, Nle$^{27}$, Asp$^{28}$, Har$^{30}$]hGHRH (1-30)NH$_2$ (SEQ ID NO: 21);

P-23252 [Dat$^1$-D-Ala$^2$, Orn$^{12}$, Abu$^{15}$, Orn$^{21}$, Nle$^{27}$, Asp$^{28}$, Har$^{30}$]hGHRH (1-30)NH$_2$;

P-23253 [Dat$^1$, Orn$^{12}$, Abu$^{15}$, Orn$^{21}$, Nle$^{27}$, Asp$^{28}$, Har$^{30}$]hGHRH(1-30) NH$_2$ (SEQ ID NO: 22);

P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$] hGHRH(1-30)NH$_2$;

P-23255 [Dat$^1$, Thr$^8$, Orn$^{12}$, Abu$^{15}$, Orn$^{21}$, Nle$^{27}$, Asp$^{28}$, Har$^{30}$]hGHRH (1-30)NH$_2$ (SEQ ID NO: 23);

P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$] hGHRH(1-30)NH$_2$;

P-23257 [Dat$^1$, Ala$^8$, Orn$^{12}$, Abu$^{15}$, Orn$^{21}$, Nle$^{27}$, Asp$^{28}$, Har$^{30}$]hGHRH (1-30)NH$_2$ (SEQ ID NO: 24);

P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;

P-23259 [N—Me-Tyr$^1$, Gln$^8$, Orn$^{12}$, Abu$^{15}$, Orn$^{21}$, Nle$^{27}$, Asp$^{28}$, Har$^{30}$] hGHRH(1-30)NH$_2$ (SEQ ID NO: 25);

P-23260 [N—Me-Tyr$^1$, D-Ala$^2$, Orn$^{12}$, Abu$^{15}$, Orn$^{21}$, Nle$^{27}$, Asp$^{28}$, Har$^{30}$] hGHRH(1-30)NH$_2$;

P-23261 [N—Me-Tyr$^1$, Orn$^{12}$, Abu$^{15}$, Orn$^{21}$, Nle$^{27}$, Asp$^{28}$, Har$^{30}$]hGHRH (1-30)NH$_2$ (SEQ ID NO: 26);

P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;

P-23263 [N—Me-Tyr$^1$, Thr$^8$, Orn$^{12}$, Abu$^{15}$, Orn$^{21}$, Nle$^{27}$, Asp$^{28}$, Har$^{30}$] hGHRH(1-30)NH$_2$ (SEQ ID NO: 27);

P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;

P-23265 [N—Me-Tyr$^1$, Ala$^8$, Orn$^{12}$, Abu$^{15}$, Orn$^{21}$, Nle$^{27}$, Asp$^{28}$, Har$^{30}$] hGHRH(1-30)NH$_2$ (SEQ ID NO: 28);

P-24340 [N—Me-Tyr$^1$, Gln$^8$, Orn$^{12}$, Abu$^{15}$, Orn$^{21}$, Nle$^{27}$, Asp$^{28}$, Aha$^{30}$] hGHRH(1-30)NH$_2$ (SEQ ID NO: 29);

P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24342 [Dat$^1$, Gln$^8$, Orn$^{12}$, Abu$^{15}$, Orn$^{21}$, Nle$^{27}$, Asp$^{28}$, Aha$^{30}$]hGHRH (1-30)NH$_2$ (SEQ ID NO: 30);

P-24344 [Dat$^1$-D-Ala$^2$, Gln$^8$, Orn$^{12}$, Abu$^{15}$, Orn$^{21}$, Nle$^{27}$, Asp$^{28}$, Aha$^{30}$] hGHRH(1-30)NH$_2$;

P-24345 [N—Me-Tyr$^1$, D-Ala$^2$, Orn$^{12}$, Abu$^{15}$, Orn$^{21}$, Nle$^{27}$, Asp$^{28}$, Aha$^{30}$] hGHRH(1-30)NH$_2$;

P-24346 [N—Me-Tyr$^1$, D-Ala$^2$, Gln$^8$, Orn$^{12}$, Abu$^{15}$, Orn$^{21}$, Nle$^{27}$, Aha$^{30}$] hGHRH(1-30)NH$_2$;

P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;

P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;

P-25501 [N—Me-Tyr$^1$, D-Ala$^2$, Orn$^{12}$, Abu$^{15}$, Orn$^{21}$, Nle$^{27}$, Gab$^{30}$]hGHRH (1-30)NH$_2$;

P-25502 [Dat$^1$, D-Ala$^2$, Fpa5$^6$, Orn$^{12}$, Abu$^{15}$, Orn$^{21}$, Nle$^{27}$, Gab$^{30}$]hGHRH (1-30)NH$_2$;

P-25503 [N—Me-Tyr$^1$, Abu$^2$, Orn$^{12}$, Abu$^{15}$, Orn$^{21}$, Nle$^{27}$, Gab$^{30}$]hGHRH (1-30)NH$_2$ (SEQ ID NO: 31);

P-25504 [Dat$^1$, D-Abu$^2$, Orn$^{12}$, Abu$^{15}$, Orn$^{21}$, Nle$^{27}$, Gab$^{30}$]hGHRH (1-30)NH$_2$;

P-25506 [N—Me-Tyr$^1$, D-Abu$^2$, Orn$^{12}$, Abu$^{15}$, Orn$^{21}$, Nle$^{27}$, Gab$^{30}$] hGHRH(1-30)NH$_2$;

P-25508 [Tfa-Tyr$^1$, D-Ala$^2$, Orn$^{12}$, Abu$^{15}$, Orn$^{21}$, Nle$^{27}$, Gab$^{30}$]hGHRH (1-30)NH$_2$;

P-25516 [N—Me-Tyr$^1$, D-Ala$^2$, Orn$^{12}$, Abu$^{15}$, Orn$^{21}$, Nle$^{27}$, Asp$^{28}$, Gab$^{30}$] hGHRH(1-30)NH$_2$;

-continued

P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$;
P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;
P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$;
P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;
P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;
P-27405 [N—Me-Tyr$^1$, Gln$^8$, Orn$^{12}$, Abu$^{15}$, Orn$^{21}$, Nle$^{27}$]hGHRH(1-29)NH—CH$_3$ (SEQ ID NO: 32);
P-27406 [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 33);
P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 34);
P-27408 [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$;
P-27409 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;
P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;
P-27411 [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$;
P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;
P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$ (SEQ ID NO: 35);
P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$;
P-27415 [N—Me-Tyr$^1$, Orn$^{12}$, Abu$^{15}$, Orn$^{21}$, Nle$^{27}$, Gab$^{30}$]hGHRH(1-30)NH—CH$_3$ (SEQ ID NO: 36);
P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;
P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;
P-27419 [Ac-Tyr$^1$, Thr$^8$, Orn$^{12}$, Abu$^{15}$, Orn$^{21}$, Nle$^{27}$]hGHRH(1-29)NH—CH$_3$ (SEQ ID NO: 37);
P-27422 [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$;
P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;
P-27424 [Dat$^1$, Thr$^8$, Orn$^{12}$, Abu$^{15}$, Orn$^{21}$, Nle$^{27}$]hGHRH(1-29)NH—CH$_3$ (SEQ ID NO: 38);
P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;
P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$;
P-27443 [N—Me-Tyr$^1$, Orn$^{12}$, Abu$^{15}$, Orn$^{21}$, Nle$^{27}$, D-Arg$^{29}$]hGHRH(1-29)NH—CH$_3$;
P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$;
P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;
P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;
P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;
P-27449 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$;
P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;
P-27451 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_3$;
P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28421 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28430 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;
P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28461 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28462 [N—Me-Tyr$^1$, D-Ala$^2$, Fpa5$^6$, Orn$^{12}$, Abu$^{15}$, Orn$^{21}$, Nle$^{27}$]hGHRH(1-29)NH—CH$_2$—CH$_3$;
P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;
P-28464 [N—Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$;
P-28465 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28467 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;
P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28474 [Dat$^1$, D-Ala$^2$, Orn$^{12}$, Abu$^{15}$, Orn$^{21}$, Nle$^{27}$, Asp$^{28}$] hGHRH(1-29)NH—CH$_2$—CH$_3$;
P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;
P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;
P-28477 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$;
P-28478 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$;
P-28479 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_2$—CH$_3$;
P-29701 [N—Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$] hGHRH](1-30)NH$_2$;
P-29702 [Dat$^1$, D-Ala$^2$, Orn$^{12}$, Abu$^{15}$, Orn$^{21}$, Nle$^{27}$, Gln-Gab$^{30}$]hGHRH(1-30)NH$_2$;
P-29703 [N—Me-Tyr$^1$, Gln$^8$, Orn$^{12}$, Abu$^{15}$, Orn$^{21}$, Nle$^{27}$, Gln-Gab$^{30}$]hGHRH(1-30)NH$_2$(SEQ ID NO: 39);
P-29704 [Dat$^1$, D-Ala$^2$, Gln$^8$, Orn$^{12}$, Abu$^{15}$, Orn$^{21,22}$, Nle$^{27}$, Gln-Gab$^{30}$] hGHRH(1-30)NH$_2$;
P-29706 [Tfa-Tyr$^1$, D-Abu$^2$, Gln$^8$, Orn$^{12}$, Abu$^{15}$, Orn$^{21}$, Nle$^{27}$, Gln-Gab$^{30}$] hGHRH(1-30)NH$_2$;
P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$;
P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$;
P-29720 [Dat$^1$, D-Ala$^2$, Orn$^{12}$, Abu$^{15}$, Orn$^{21}$, Nle$^{27}$, Asp$^{28}$, Gln-Gab$^{30}$] hGHRH(1-30)NH$_2$;
P-29721 [Dat$^1$, D-Ala$^2$, Gln$^8$, Orn$^{12}$, Abu$^{15}$, Orn$^{2122}$, Nle$^{27}$, Asp$^{28}$, Gln-Gab$^{30}$]hGHRH(1-30)NH$_2$;
P-29722 [Tfa-Tyr$^1$, D-Abu$^2$, Gln$^8$, Orn$^{12}$, Abu$^{15}$, Orn$^{21}$, Nle$^{27}$, Asp$^{28}$, Gln$^{30}$, Gab$^{31}$]hGHRH(1-30)NH$_2$;
P-29723 [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$] hGHRH(1-30)NH$_2$; and
P-29724 [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$]hGHRH(1-30)NH$_2$, and pharmaceutically acceptable salts thereof.

8. The method of claim 7, wherein the grafted tissue proliferate and repopulate damaged tissues in vivo.

9. The method of claim 7, wherein the grafted tissue comprises pancreatic cells.

10. The method of claim 7, wherein the grafted tissue comprises pancreatic cells co-cultured with non-pancreatic cells.

11. The method of claim 7, wherein GHRH agonist peptide is selected from the group having the formula:

| | |
|---|---|
| P-20367 | [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29); |
| P-20361 | [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-27406 | [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$(SEQ ID NO: 33); |
| P-28420 | [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$; |
| P-28421 | [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$; |
| P-27403 | [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$; |
| P-27409 | [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$; |
| P-20356 | [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29)(SEQ ID NO: 6); and |
| P-25502 | [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$. |

12. A method of modulating a function of an insulin producing cell, the method comprising exposing the insulin producing cell to an effective amount of a GHRH agonist peptide, wherein the GHRH agonist peptide is selected from the peptides having the formula:

| | |
|---|---|
| P-20103 | [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29)(SEQ ID NO: 2); |
| P-20105 | [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29); |
| P-20107 | [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGHRH(1-29)(SEQ ID NO: 3); |
| P-20109 | [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGHRH(1-29); |
| P-20110 | [N—Me-Tyr$^1$, D-Ala$^2$, Fpa5$^6$, Orn$^{12}$, Abu$^{15}$, Orn$^{21}$, Nle$^{27}$, Agm$^{29}$]hGHRH(1-29); |
| P-20111 | [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29); |
| P-20113 | [N—Me-Tyr$^1$, Fpa5$^6$, Orn$^{12}$, Abu$^{15}$, Orn$^{21}$, Nle$^{27}$, Asp$^{28}$, Agm$^{29}$]hGHRH(1-29)(SEQ ID NO: 4); |
| P-20115 | [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH(1-29)(SEQ ID NO: 5); |
| P-20117 | [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH(1-29); |
| P-20350 | [Dat$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20351 | [Ac—N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20356 | [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29)(SEQ ID NO: 6); |
| P-20357 | [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29); |
| P-20358 | [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29); |
| P-20359 | [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH(1-29); |
| P-20360 | [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$]hGHRH(1-29); |
| P-20361 | [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20367 | [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29); |
| P-20370 | [N—Me-Tyr$^1$, Orn$^{12}$, Abu$^{15}$, Orn$^{21}$, Nle$^{27}$, Asp$^{28}$, Agm$^{29}$]hGHRH(1-29)(SEQ ID NO: 7); |
| P-20371 | [N—Me-Tyr$^1$, Thr$^8$, Orn$^{12}$, Abu$^{15}$, Orn$^{21}$, Nle$^{27}$, Asp$^{28}$, Agm$^{29}$]hGHRH(1-29)(SEQ ID NO: 8); |
| P-20372 | [N—Me-Tyr$^1$, Ala$^8$, Orn$^{12}$, Abu$^{15}$, Orn$^{21}$, Nle$^{27}$, Asp$^{28}$, Agm$^{29}$]hGHRH(1-29)(SEQ ID NO: 9); |
| P-20373 | [N—Me-Tyr$^1$, Gln$^8$, Orn$^{12}$, Abu$^{15}$, Orn$^{21}$, Nle$^{27}$, Agm$^{29}$]hGHRH(1-29)(SEQ ID NO: 10); |
| P-20374 | [N—Me-Tyr$^1$, Orn$^{12}$, Abu$^{15}$, Orn$^{21}$, Nle$^{27}$, Agm$^{29}$]hGHRH(1-29)(SEQ ID NO: 11); |
| P-20375 | [N—Me-Tyr$^1$, Thr$^8$, Orn$^{12}$, Abu$^{15}$, Orn$^{21}$, Nle$^{27}$, Agm$^{29}$]hGHRH(1-29)(SEQ ID NO: 12); |
| P-20376 | [N—Me-Tyr$^1$, Ala$^8$, Orn$^{12}$, Abu$^{15}$, Orn$^{21}$, Nle$^{27}$, Agm$^{29}$]hGHRH(1-29)(SEQ ID NO: 13); |
| P-21300 | [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$; |
| P-21301 | [N—Me-Tyr$^1$, Orn$^{12}$, Abu$^{15}$, Orn$^{21}$, Nle$^{27}$, Asp$^{28}$, Amc$^{30}$]hGHRH(1-30)NH$_2$(SEQ ID NO: 14); |
| P-21303 | [N—Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$; |
| P-21304 | [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$; |
| P-21305 | [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$; |
| P-21306 | [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$; |
| P-21307 | [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$; |
| P-21308 | [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$; |
| P-21309 | [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGHRH(1-30)NH$_2$; |
| P-21310 | [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$; |
| P-21311 | [N—Me-Tyr$^1$, D-Ala$^2$, His$^{11}$, Orn$^{12}$, Abu$^{15}$, His20, Orn$^{21}$, Nle$^{27}$, Asp$^{28}$, Amc$^{30}$]hGHRH(1-30)NH$_2$; |
| P-22325 | [N—Me-Tyr$^1$, Gln$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 15); |
| P-22326 | [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$; |
| P-22327 | [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 16); |
| P-22328 | [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$; |
| P-22329 | [N—Me-Tyr$^1$, D-Ala$^2$, Orn$^{12}$, Abu$^{15}$, Orn$^{21}$, Nle$^{27}$, Apa$^{30}$]hGHRH(1-30)NH$_2$; |
| P-22330 | [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$; |
| P-22331 | [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$; |
| P-22332 | [N—Me-Tyr$^1$, Orn$^{12}$, Abu$^{15}$, Orn$^{21}$, Nle$^{27}$, Asp$^{28}$, Apa$^{30}$]hGHRH(1-30)NH$_2$(SEQ ID NO: 17); |
| P-22334 | [N—Me-Tyr$^1$, Orn$^{12}$, Abu$^{15}$, Orn$^{21}$, Nle$^{27}$, Apa$^{30}$]hGHRH(1-30)NH$_2$(SEQ ID NO: 18); |
| P-22335 | [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 19); |
| P-22336 | [N—Me-Tyr$^1$ Ala$^8$, Orn$^{12}$, Abu$^{15}$, Orn$^{21}$, Nle$^{27}$, Asp$^{28}$, Apa$^{30}$]hGHRH(1-30)NH$_2$(SEQ ID NO: 20); |
| P-22337 | [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGHRH(1-30)NH$_2$; |
| P-23250 | [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$; |
| P-23251 | [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 21); |
| P-23252 | [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$_2$; |
| P-23253 | [Dat$^1$, Orn$^{12}$, Abu$^{15}$, Orn$^{21}$, Nle$^{27}$, Asp$^{28}$, Har$^{30}$]hGHRH(1-30)NH$_2$(SEQ ID NO: 22); |
| P-23254 | [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$; |
| P-23255 | [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 23); |
| P-23256 | [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$; |
| P-23257 | [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 24); |
| P-23258 | [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$; |
| P-23259 | [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 25); |
| P-23260 | [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$; |
| P-23261 | [N—Me-Tyr$^1$, Orn$^{12}$, Abu$^{15}$, Orn$^{21}$, Nle$^{27}$, Asp$^{28}$, Har$^{30}$]hGHRH(1-30)NH$_2$(SEQ ID NO: 26); |
| P-23262 | [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$; |

P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 27);

P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;

P-23265 [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$(SEQ ID NO: 28);

P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$(SEQ ID NO: 29);

P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24342 [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$(SEQ ID NO: 30);

P-24344 [Dat$^1$-D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$;

P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;

P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;

P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;

P-25501 [N—Me-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25502 [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$;

P-25503 [N—Me-Tyr$^1$, Abu$^2$, Orn$^{12}$, Abu$^{15}$, Orn$^{21}$, Nle$^{27}$, Gab$^{30}$]hGHRH(1-30)NH$_2$(SEQ ID NO: 31);

P-25504 [Dat$^1$, D-Abu$^2$, Orn$^{12}$, Abu$^{15}$, Orn$^{21}$, Nle$^{27}$, Gab$^{30}$]hGHRH(1-30)NH$_2$;

P-25506 [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$;

P-25508 [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$;

P-26802 [Dat$^1$, D-Ala$^2$, Thr$^8$, His$^{11}$, Orn$^{12}$, Abu$^{15}$, His20, Orn$^{21}$, Nle$^{27}$, Ada$^{30}$]hGHRH(1-30)NH$_2$;

P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;

P-26804 [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$;

P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;

P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27405 [N—Me-Tyr$^1$, Gln$^8$, Orn$^{12}$, Abu$^{15}$, Orn$^{21}$, Nle$^{27}$]hGHRH(1-29)NH—CH$_3$(SEQ ID NO: 32);

P-27406 [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$(SEQ ID NO: 33);

P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$(SEQ ID NO: 34);

P-27408 [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$;

P-27409 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;

P-27411 [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$;

P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;

P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$(SEQ ID NO: 35);

P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$;

P-27415 [N—Me-Tyr$^1$, Orn$^{12}$, Abu$^{15}$, Orn$^{21}$, Nle$^{27}$, Gab$^{30}$]hGHRH(1-30)NH—CH$_3$(SEQ ID NO: 36);

P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;

P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27419 [Ac-Tyr$^1$, Thr$^8$, Orn$^{12}$, Abu$^{15}$, Orn$^{21}$, Nle$^{27}$]hGHRH(1-29)NH—CH$_3$(SEQ ID NO: 37);

P-27422 [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$;

P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27424 [Dat$^1$, Thr$^8$, Orn$^{12}$, Abu$^{15}$, Orn$^{21}$, Nle$^{27}$]hGHRH(1-29)NH—CH$_3$(SEQ ID NO: 38);

P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$;

P-27443 [N—Me-Tyr$^1$, Orn$^{12}$, Abu$^{15}$, Orn$^{21}$, Nle$^{27}$, D-Arg$^{29}$]hGHRH(1-29)NH—CH$_3$;

P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$;

P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;

P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;

P-27449 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$;

P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;

P-27451 [N—Me-Tyr$^1$, D-Ala$^2$, Gln$^8$, His$^{11}$, Orn$^{12}$, Abu$^{15}$, His$^{11}$, Orn$^{21}$, Nle$^{27}$, Asp$^{28}$, Apa$^{30}$]hGHRH(1-30)NH—CH$_3$;

P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28421 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;

P-28430 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;

P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28461 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28462 [N—Me-Tyr$^1$, D-Ala$^2$, Fpa5$^6$, Orn$^{12}$, Abu$^{15}$, Orn$^{21}$, Nle$^{27}$]hGHRH(1-29)NH—CH$_2$—CH$_3$;

P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;

P-28464 [N—Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$;

P-28465 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;

P-28467 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;

P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;

P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;

P-28474 [Dat$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;

P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;

P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;

P-28477 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$;

-continued

| | |
|---|---|
| P-28478 | [N—Me-Tyr¹, D-Ala², Gln⁸, Orn¹², Abu¹⁵, Orn²¹, Nle²⁷, Asp²⁸, Har³⁰]hGHRH(1-30)NH—CH₂—CH₃; |
| P-28479 | [N—Me-Tyr¹, D-Ala², Gln⁸, His¹¹, Orn¹², Abu¹⁵, His²⁰, Orn²¹, Nle²⁷, Asp²⁸, Apa³⁰]hGHRH(1-30)NH—CH₂—CH₃; |
| P-29701 | [N—Me-Tyr¹, D-Ala², Gln⁸, Orn¹², Abu¹⁵, Orn²¹, Nle²⁷, Asp²⁸, Gln-Gab³⁰]hGHRH](1-30)NH₂; |
| P-29702 | [Dat¹, D-Ala², Orn¹², Abu¹⁵, Orn²¹, Nle²⁷, Gln-Gab³⁰]hGHRH(1-30)NH₂; |
| P-29703 | [N—Me-Tyr¹, Gln⁸, Orn¹², Abu¹⁵, Orn²¹, Nle²⁷, Gln-Gab³⁰]hGHRH(1-30)NH₂(SEQ ID NO: 39); |
| P-29704 | [Dat¹, D-Ala², Gln⁸, Orn¹², Abu¹⁵, Orn²¹,²², Nle²⁷, Gln-Gab³⁰]hGHRH(1-30)NH₂; |
| P-29706 | [Tfa-Tyr¹, D-Abu², Gln⁸, Orn¹², Abu¹⁵, Orn²¹, Nle²⁷, Gln-Gab³⁰]hGHRH(1-30)NH₂; |
| P-29708 | [N—Me-Tyr¹, D-Ala², Fpa5⁶, Orn¹², Abu¹⁵, Orn²¹, Nle²⁷, Gln-Gab³⁰]hGHRH(1-30)NH₂; |
| P-29710 | [N—Me-Tyr¹, D-Ala², Fpa5⁶, Ala⁸, Orn¹², Abu¹⁵, Orn²¹, Nle²⁷, Gln-Gab³⁰]hGHRH(1-30)NH₂; |
| P-29720 | [Dat¹, D-Ala², Orn¹², Abu¹⁵, Orn²¹, Nle²⁷, Asp²⁸, Gln-Gab³⁰]hGHRH(1-30)NH₂; |
| P-29721 | [Dat¹, D-Ala², Gln⁸, Orn¹², Abu¹⁵, Orn²¹,²², Nle²⁷, Asp²⁸, Gln-Gab³⁰]hGHRH(1-30)NH₂; |
| P-29722 | [Tfa-Tyr¹, D-Abu2, Gln⁸, Orn¹², Abu¹⁵, Orn²¹, Nle²⁷, Asp²⁸, Gln³⁰, Gab³¹]hGHRH(1-30)NH₂; |
| P-29723 | [N—Me-Tyr¹, D-Ala², Fpa5⁶, Orn¹², Abu¹⁵, Orn²¹, Nle²⁷, Asp²⁸, Gln-Gab³⁰]hGHRH(1-30)NH₂; |
| P-29724 | [N—Me-Tyr¹, D-Ala², Fpa5⁶, Ala⁸, Orn¹², Abu¹⁵, Orn²¹, Nle²⁷, Asp²⁸, Gln Gab³⁰]hGHRH(1-30)NH₂, | and pharmaceutically acceptable salts thereof.

13. The method of claim 12, wherein the insulin producing cell comprises an islet cell.

14. The method of claim 12, wherein the insulin producing cell comprises a cell expressing a recombinant insulin molecule.

15. The method of claim 14, wherein the cell expressing the recombinant insulin molecule comprises a stem cell, a pancreatic cell, a transformed cell, a microbe or a cell sensitive to GHRH.

16. The method of claim 12, wherein GHRH agonist peptide is selected from the group having the formula:

| | |
|---|---|
| P-20367 | [N—Me-Tyr¹, D-Ala², Orn¹², Abu¹⁵, Orn²¹, Nle²⁷, Asp²⁸, Agm²⁹]hGHRH(1-29); |
| P-20361 | [N—Me-Tyr¹, D-Ala², Gln⁸, Orn¹², Abu¹⁵, Orn²¹, Nle²⁷, Asp²⁸, Agm²⁹]hGHRH(1-29); |
| P-27406 | [N—Me-Tyr¹, Gln⁸, Orn¹², Abu¹⁵, Orn²¹, Nle²⁷, Asp²⁸]hGHRH(1-29)NH—CH₃(SEQ ID NO: 33); |
| P-28420 | [N—Me-Tyr¹, D-Ala², Gln⁸, Orn¹², Abu¹⁵, Orn²¹, Nle²⁷, Asp²⁸]hGHRH(1-29)NH—CH₂—CH₃; |
| P-28421 | [N—Me-Tyr¹, D-Ala², Orn¹², Abu¹⁵, Orn²¹, Nle²⁷, Asp²⁸]hGHRH(1-29)NH—CH₂—CH₃; |
| P-27403 | [N—Me-Tyr¹, D-Ala², Gln⁸, Orn¹², Abu¹⁵, Orn²¹, Nle²⁷, Asp²⁸]hGHRH(1-29)NH—CH₃; |
| P-27409 | [N—Me-Tyr¹, D-Ala², Orn¹², Abu¹⁵, Orn²¹, Nle²⁷, Asp²⁸]hGHRH(1-29)NH—CH₃; |
| P-20356 | [N—Me-Tyr¹, Gln⁸, Orn¹², Abu¹⁵, Orn²¹, Nle²⁷, Asp²⁸, Agm²⁹]hGHRH(1-29)(SEQ ID NO: 6); and |
| P-25502 | [Dat¹, D-Ala², Fpa5⁶, Orn¹², Abu¹⁵, Orn²¹, Nle²⁷, Gab³⁰]hGHRH(1-30)NH₂. |

17. A method of transplanting insulin producing cells into a diabetic mammal in need thereof, the method comprising:
transplanting the insulin producing cells into an adrenal gland of the diabetic mammal; and
administering a therapeutically effective amount of a GHRH agonist peptide to the diabetic mammal, wherein the GHRH agonist peptide is selected from the peptides having the formula:

| | |
|---|---|
| P-20103 | [N—Me-Tyr¹, Fpa5⁶, Gln⁸, Orn¹², Abu¹⁵, Orn²¹, Nle²⁷, Asp²⁸, Agm²⁹]hGHRH(1-29) (SEQ ID NO: 2); |
| P-20105 | [N—Me-Tyr¹, D-Ala², Fpa5⁶, Gln⁸, Orn¹², Abu¹⁵, Orn²¹, Nle²⁷, Asp²⁸, Agm²⁹]hGHRH(1-29); |
| P-20107 | [N—Me-Tyr¹, Fpa5⁶, Ala⁸, Orn¹², Abu¹⁵, Orn²¹, Nle²⁷, Asp²⁸, Agm²⁹]hGHRH(1-29) (SEQ ID NO: 3); |
| P-20109 | [N—Me-Tyr¹, D-Ala², Fpa5⁶, Ala⁸, Orn¹², Abu¹⁵, Orn²¹, Nle²⁷, Asp²⁸, Agm²⁹]hGHRH(1-29); |
| P-20110 | [N—Me-Tyr¹, D-Ala², Fpa5⁶, Orn¹², Abu¹⁵, Orn²¹, Nle²⁷, Agm²⁹]hGHRH(1-29); |
| P-20111 | [N—Me-Tyr¹, D-Ala², Fpa5⁶, Thr⁸, Orn¹², Abu¹⁵, Orn²¹, Nle²⁷, Asp²⁸, Agm²⁹]hGHRH(1-29); |
| P-20113 | [N—Me-Tyr¹, Fpa5⁶, Orn¹², Abu¹⁵, Orn²¹, Nle²⁷, Asp²⁸, Agm²⁹]hGHRH(1-29) (SEQ ID NO: 4); |
| P-20115 | [N—Me-Tyr¹, Fpa5⁶, Thr⁸, Orn¹², Abu¹⁵, Orn²¹, Nle²⁷, Asp²⁸, Agm²⁹]hGHRH(1-29) (SEQ ID NO: 5); |
| P-20117 | [N—Me-Tyr¹, D-Ala², Fpa5⁶, Gln⁸, Orn¹², Abu¹⁵, Orn²¹, Nle²⁷, Agm²⁹]hGHRH(1-29); |
| P-20350 | [Dat¹, D-Ala², Gln⁸, Orn¹², Abu¹⁵, Orn²¹, Nle²⁷, Asp²⁸, Agm²⁹]hGHRH(1-29); |
| P-20351 | [Ac-N—Me-Tyr¹, D-Ala², Gln⁸, Orn¹², Abu¹⁵, Orn²¹, Nle²⁷, Asp²⁸, Agm²⁹]hGHRH(1-29); |
| P-20356 | [N—Me-Tyr¹, Gln⁸, Orn¹², Abu¹⁵, Orn²¹, Nle²⁷, Asp²⁸, Agm²⁹]hGHRH(1-29) (SEQ ID NO: 6); |
| P-20357 | [Dat¹, D-Ala², N—Me-Ala⁸, Orn¹², Abu¹⁵, Orn²¹, Nle²⁷, Asp²⁸, Agm²⁹]hGHRH(1-29); |
| P-20358 | [N—Me-Tyr¹, D-Ala², N—Me-Ala⁸, Orn¹², Abu¹⁵, Orn²¹, Nle²⁷, Asp²⁸, Agm²⁹]hGHRH(1-29); |
| P-20359 | [N—Me-Tyr¹, D-Ala², Fpa5⁶, Orn¹², Abu¹⁵, Orn²¹, Nle²⁷, Asp²⁸, Agm²⁹]hGHRH(1-29); |
| P-20360 | [N—Me-Tyr¹, D-Ala², Thr⁸, Orn¹², Abu¹⁵, Orn²¹, Nle²⁷, Asp²⁸, Agm²⁹]hGHRH(1-29); |
| P-20361 | [N—Me-Tyr¹, D-Ala², Gln⁸, Orn¹², Abu¹⁵, Orn²¹, Nle²⁷, Asp²⁸, Agm²⁹]hGHRH(1-29); |
| P-20367 | [N—Me-Tyr¹, D-Ala², Orn¹², Abu¹⁵, Orn²¹, Nle²⁷, Asp²⁸, Agm²⁹]hGHRH(1-29); |
| P-20370 | [N—Me-Tyr¹, Orn¹², Abu¹⁵, Orn²¹, Nle²⁷, Asp²⁸, Agm²⁹]hGHRH(1-29) (SEQ ID NO: 7); |
| P-20371 | [N—Me-Tyr¹, Thr⁸, Orn¹², Abu¹⁵, Orn²¹, Nle²⁷, Asp²⁸, Agm²⁹]hGHRH(1-29) (SEQ ID NO: 8); |
| P-20372 | [N—Me-Tyr¹, Ala⁸, Orn¹², Abu¹⁵, Orn²¹, Nle²⁷, Asp²⁸, Agm²⁹]hGHRH(1-29) (SEQ ID NO: 9); |

-continued

P-20373 [N—Me-Tyr$^1$, Gln$^8$, Orn$^{12}$, Abu$^{15}$, Orn$^{21}$, Nle$^{27}$, Agm$^{29}$]hGHRH(1-29) (SEQ ID NO: 10);
P-20374 [N—Me-Tyr$^1$, Orn$^{12}$, Abu$^{15}$, Orn$^{21}$, Nle$^{27}$, Agm$^{29}$]hGHRH(1-29) (SEQ ID NO: 11);
P-20375 [N—Me-Tyr$^1$, Thr$^8$, Orn$^{12}$, Abu$^{15}$, Orn$^{21}$, Nle$^{27}$, Agm$^{29}$]hGHRH(1-29) (SEQ ID NO: 12);
P-20376 [N—Me-Tyr$^1$, Ala$^8$, Orn$^{12}$, Abu$^{15}$, Orn$^{21}$, Nle$^{27}$, Agm$^{29}$]hGHRH(1-29) (SEQ ID NO: 13);
P-21300 [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;
P-21301 [N—Me-Tyr$^1$, Orn$^{12}$, Abu$^{15}$, Orn$^{21}$, Nle$^{27}$, Asp$^{28}$, Amc$^{30}$]hGHRH(1-30)NH$_2$ (SEQ ID NO: 14);
P-21303 [N—Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;
P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;
P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;
P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$;
P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGHRH(1-30)NH$_2$;
P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc30]hGHRH(1-30)NH$_2$;
P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;
P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 15);
P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22327 [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 16);
P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22329 [N—Me-Tyr$^1$, D-Ala$^2$, Orn$^{12}$, Abu$^{15}$, Orn$^{21}$, Nle$^{27}$, Apa$^{30}$]hGHRH(1-30)NH$_2$;
P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$;
P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$;
P-22332 [N—Me-Tyr$^1$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 17);
P-22334 [N—Me-Tyr$^1$, Orn$^{12}$, Abu$^{15}$, Orn$^{21}$, Nle$^{27}$, Apa$^{30}$]hGHRH(1-30)NH$_2$ (SEQ ID NO: 18);
P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 19);
P-22336 [N—Me-Tyr$^1$ Ala$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 20);
P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23251 [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 21);
P-23252 [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23253 [Dat$^1$, Orn$^{12}$, Abu$^{15}$, Orn$^{21}$, Nle$^{27}$, Asp$^{28}$, Har$^{30}$]hGHRH(1-30)NH$_2$ (SEQ ID NO: 22);
P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23255 [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 23);
P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23257 [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 24);
P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23259 [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 25);
P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23261 [N—Me-Tyr$^1$, Orn$^{12}$, Abu$^{15}$, Orn$^{21}$, Nle$^{27}$, Asp$^{28}$, Har$^{30}$]hGHRH(1-30)NH$_2$ (SEQ ID NO: 26);
P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 27);
P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;

| | |
|---|---|
| P-23265 | [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 28); |
| P-24340 | [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$ (SEQ ID NO: 29); |
| P-24341 | [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$; |
| P-24342 | [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$ (SEQ ID NO: 30); |
| P-24344 | [Dat$^1$-D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$; |
| P-24345 | [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$; |
| P-24346 | [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$; |
| P-24347 | [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$; |
| P-24348 | [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$; |
| P-25501 | [N—Me-Tyr$^1$, D-Ala$^2$, Orn$^{12}$, Abu$^{15}$, Orn$^{21}$, Nle$^{27}$, Gab$^{30}$]hGHRH(1-30)NH$_2$; |
| P-25502 | [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$; |
| P-25503 | [N—Me-Tyr$^1$, Abu$^2$, Orn$^{12}$, Abu$^{15}$, Orn$^{21}$, Nle$^{27}$, Gab$^{30}$]hGHRH(1-30)NH$_2$ (SEQ ID NO: 31); |
| P-25504 | [Dat$^1$, D-Abu$^2$, Orn$^{12}$, Abu$^{15}$, Orn$^{21}$, Nle$^{27}$, Gab$^{30}$]hGHRH(1-30)NH$_2$; |
| P-25506 | [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$; |
| P-25508 | [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$; |
| P-25516 | [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$; |
| P-26802 | [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$; |
| P-26803 | [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$; |
| P-26804 | [N—Me-Tyr$^1$, D-Ala$^2$, Gln$^8$, Orn$^{12}$, Abu$^{15}$, Orn$^{21}$, Nle$^{27}$, Ada$^{30}$]hGHRH(1-30)NH$_2$; |
| P-27400 | [Dat$^1$, D-Ala$^2$, Orn$^{12}$, Abu$^{15}$, Orn$^{21}$, Nle$^{27}$, Asp$^{28}$]hGHRH(1-29)NH—CH$_3$; |
| P-27401 | [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$; |
| P-27403 | [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$; |
| P-27404 | [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$; |
| P-27405 | [N—Me-Tyr$^1$, Gln$^8$, Orn$^{12}$, Abu$^{15}$, Orn$^{21}$, Nle$^{27}$]hGHRH(1-29)NH—CH$_3$ (SEQ ID NO: 32); |
| P-27406 | [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 33); |
| P-27407 | [Dat$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 34); |
| P-27408 | [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$; |
| P-27409 | [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$; |
| P-27410 | [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$; |
| P-27411 | [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$; |
| P-27412 | [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$; |
| P-27413 | [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$ (SEQ ID NO: 35); |
| P-27414 | [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$; |
| P-27415 | [N—Me-Tyr$^1$, Orn$^{12}$, Abu$^{15}$, Orn$^{21}$, Nle$^{27}$, Gab$^{30}$]hGHRH(1-30)NH—CH$_3$ (SEQ ID NO: 36); |
| P-27416 | [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$; |
| P-27417 | [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$; |
| P-27418 | [Ac-Tyr$^1$, D-Ala$^2$, Fpa5$^6$, Orn$^{12}$, Abu$^{15}$, Orn$^{21}$, Nle$^{27}$, Asp28]hGHRH(1-29)NH—CH$_3$; |
| P-27419 | [Ac-Tyr$^1$, Thr$^8$, Orn$^{12}$, Abu$^{15}$, Orn$^{21}$, Nle$^{27}$]hGHRH(1-29)NH—CH$_3$ (SEQ ID NO: 37); |
| P-27422 | [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$; |
| P-27423 | [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$; |
| P-27424 | [Dat$^1$, Thr$^8$, Orn$^{12}$, Abu$^{15}$, Orn$^{21}$, Nle$^{27}$]hGHRH(1-29)NH—CH$_3$ (SEQ ID NO: 38); |
| P-27425 | [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$; |
| P-27440 | [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH3; |
| P-27441 | [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$; |
| P-27442 | [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH CH$_3$; |
| P-27443 | [N—Me-Tyr$^1$, Orn$^{12}$, Abu$^{15}$, Orn$^{21}$, Nle$^{27}$, D-Arg$^{29}$]hGHRH(1-29)NH CH$_3$; |
| P-27444 | [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$; |

-continued

P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;

P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;

P-27449 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_3$;

P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;

P-27451 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_3$;

P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28421 [N—Me-Tyr$^1$, D-Ala$^2$, Orn$^{12}$, Abu$^{15}$, Orn$^{21}$, Nle$^{27}$, Asp28]hGHRH(1-29)NH—CH$_2$—CH$_3$;

P-28430 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;

P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28461 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28462 [N—Me-Tyr$^1$, D-Ala$^2$, Fpa5$^6$, Orn$^{12}$, Abu$^{15}$, Orn$^{21}$, Nle$^{27}$]hGHRH(1-29)NH—CH$_2$—CH$_3$;

P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;

P-28464 [N—Me-Tyr$^1$, D-Ala$^2$, Fpa5$^6$, Gln$^8$, Orn$^{12}$, Abu$^{15}$, Orn$^{21}$, Nle27]hGHRH(1-29)NH—CH$_2$—CH$_3$;

P-28465 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;

P-28467 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;

P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;

P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;

P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;

P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;

P-28474 [Dat$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;

P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;

P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;

P-28477 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH—CH$_2$—CH$_3$;

P-28478 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$;

P-28479 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_2$—CH$_3$;

P-29701 [N—Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH](1-30)NH$_2$;

P-29702 [Dat$^1$, D-Ala$^2$, Orn$^{12}$, Abu$^{15}$, Orn$^{21}$, Nle$^{27}$, Gln-Gab$^{30}$]hGHRH(1-30)NH$_2$;

P-29703 [N—Me-Tyr$^1$, Gln$^8$, Orn$^{12}$, Abu$^{15}$, Orn$^{21}$, Nle$^{27}$, Gln-Gab$^{30}$]hGHRH(1-30)NH$_2$ (SEQ ID NO: 39);

P-29704 [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$;

P-29706 [Dat$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$;

P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$;

P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$;

P-29720 [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$;

P-29721 [Dat$^1$, D-Ala$^2$, Gln$^8$, Orn$^{12}$, Abu$^{15}$, Orn$^{21,22}$, Nle$^{27}$, Asp$^{28}$, Gln-Gab$^{30}$]hGHRH(1-30)NH$_2$;

P-29722 [Tfa-Tyr$^1$, D-Abu$^2$, Gln$^8$, Orn$^{12}$, Abu$^{15}$, Orn$^{21}$, Nle$^{27}$, Asp$^{28}$, Gln$^{30}$, Gab$^{30}$]hGHRH(1-30)NH$_2$;

| | |
|---|---|
| P-29723 | [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGHRH(1-30)NH$_2$; |
| P-29724 | [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Gln-Gab$^{30}$]hGHRH(1-30)NH$_2$, | and pharmaceutically acceptable salts thereof.

18. The method of claim 17, wherein the insulin producing cells are optionally exposed to the GHRH agonist peptide prior to transplantation into the diabetic mammal.

19. The method of claim 17, wherein the peptide is administered pre-transplantation, concurrently with transplantation, post-transplantation, or any combinations thereof.

20. The method of claim 17, wherein GHRH agonist peptide is selected from the group having the formula:

| | |
|---|---|
| P-20367 | [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29); |
| P-20361 | [N—Me-Tyr$^1$, D-Ala$^2$, Gln$^8$, Orn$^{12}$, Abu$^{15}$, Orn$^{21}$, Nle$^{27}$, Asp$^{28}$, Agrn$^{29}$]hGHRH(1-29); |
| P-27406 | [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 33); |

-continued

| | |
|---|---|
| P-28420 | [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$; |
| P-28421 | [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$; |
| P-27403 | [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$; |
| P-27409 | [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$; |
| P-20356 | [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) (SEQ ID NO: 6); and |
| P-25502 | [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$. |

21. A method of treating a patient diagnosed with diabetes comprising administering a therapeutically effective amount of a GHRH agonist peptide to the patient, wherein the GHRH agonist peptide is selected from the group having the formula:

| | |
|---|---|
| P-20103 | [N—Me-Tyr$^1$, Fpa5$^6$, Gln$^8$, Orn$^{12}$, Abu$^{15}$, Orn$^{21}$, Nle$^{27}$, Asp$^{28}$, Agm$^{29}$]hGHRH(1-29) (SEQ ID NO: 2); |
| P-20105 | [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$, Agm$^{29}$]hGHRH(1-29); |
| P-20107 | [N—Me-Tyr$^1$, Fpa5$^6$, Ala$^8$, Orn$^{12}$, Abu$^{15}$, Orn$^{21}$, Nle$^{27}$, Asp$^{28}$, Agm$^{29}$]hGHRH(1-29) (SEQ ID NO: 3); |
| P-20109 | [N—Me-Tyr$^1$, D-Ala$^2$, Fpa5$^6$, Ala$^8$, Orn$^{12}$, Abu$^{15}$, Orn$^{21}$, Nle$^{27}$, Asp$^{28}$, Agm$^{29}$]hGHRH(1-29); |
| P-20110 | [N—Me-Tyr$^1$, D-Ala$^2$, Fpa5$^6$, Orn$^{12}$, Abu$^{15}$, Orn$^{21}$, Nle$^{27}$, Agm$^{29}$]hGHRH(1-29); |
| P-20111 | [N—Me-Tyr$^1$, D-Ala$^2$, Fpa5$^6$, Thr$^8$, Orn$^{12}$, Abu$^{15}$, Orn$^{21}$, Nle$^{27}$, Asp$^{28}$, Agm$^{29}$]hGHRH(1-29); |
| P-20113 | [N—Me-Tyr$^1$, Fpa5$^6$, Orn$^{12}$, Abu$^{15}$, Orn$^{21}$, Nle$^{27}$, Asp$^{28}$, Agm$^{29}$]hGHRH(1-29) (SEQ ID NO: 4); |
| P-20115 | [N—Me-Tyr$^1$, Fpa5$^6$, Thr$^8$, Orn$^{12}$, Abu$^{15}$, Orn$^{21}$, Nle$^{27}$, Asp$^{28}$, Agm$^{29}$]hGHRH(1-29) (SEQ ID NO: 5); |
| P-20117 | [N—Me-Tyr$^1$, D-Ala$^2$, Fpa5$^6$, Gln$^8$, Orn$^{12}$, Abu$^{15}$, Orn$^{21}$, Nle$^{27}$, Agm$^{29}$]hGHRH(1-29); |
| P-20350 | [Dat$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20351 | [Ac-N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20356 | [N—Me-Tyr$^1$, Gln$^8$, Orn$^{12}$, Abu$^{15}$, Orn$^{21}$, Nle$^{27}$, Asp$^{28}$, Agm$^{29}$]hGHRH(1-29) (SEQ ID NO: 6); |
| P-20357 | [Dat$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29); |
| P-20358 | [N—Me-Tyr$^1$, D-Ala$^2$, N—Me-Ala$^8$, Orn$^{12}$, Abu$^{15}$, Orn$^{21}$, Nle$^{27}$, Asp$^{28}$, Agm$^{29}$]hGHRH(1-29); |
| P-20359 | [N—Me-Tyr$^1$, D-Ala$^2$, Fpa5$^6$, Orn$^{12}$, Abu$^{15}$, Orn$^{21}$, Nle$^{27}$, Asp$^{28}$, Agm$^{29}$]hGHRH(1-29); |
| P-20360 | [N—Me-Tyr$^1$, D-Ala$^2$, Thr$^8$, Orn$^{12}$, Abu$^{15}$, Orn$^{21}$, Nle$^{27}$, Asp$^{28}$, Agm$^{29}$] hGHRH(1-29); |
| P-20361 | [N—Me-Tyr$^1$, D-Ala$^2$, Gln$^8$, Orn$^{12}$, Abu$^{15}$, Orn$^{21}$, Nle$^{27}$, Asp$^{28}$, Agm$^{29}$]hGHRH(1-29); |
| P-20367 | [N—Me-Tyr$^1$, D-Ala$^2$, Orn$^{12}$, Abu$^{15}$, Orn$^{21}$, Nle$^{27}$, Asp$^{28}$, Agm$^{29}$]hGHRH(1-29); |
| P-20370 | [N—Me-Tyr$^1$, Orn$^{12}$, Abu$^{15}$, Orn$^{21}$, Nle$^{27}$, Asp$^{28}$, Agm$^{29}$]hGHRH(1-29) (SEQ ID NO: 7); |
| P-20371 | [N—Me-Tyr$^1$, Thr$^8$, Orn$^{12}$, Abu$^{15}$, Orn$^{21}$, Nle$^{27}$, Asp$^{28}$, Agm$^{29}$]hGHRH(1-29) (SEQ ID NO: 8); |
| P-20372 | [N—Me-Tyr$^1$, Ala$^8$, Orn$^{12}$, Abu$^{15}$, Orn$^{21}$, Nle$^{27}$, Asp$^{28}$, Agm$^{29}$]hGHRH(1-29) (SEQ ID NO: 9); |
| P-20373 | [N—Me-Tyr$^1$, Gln$^8$, Orn$^{12}$, Abu$^{15}$, Orn$^{21}$, Nle$^{27}$, Agm$^{29}$]hGHRH(1-29) (SEQ ID NO: 10); |
| P-20374 | [N—Me-Tyr$^1$, Orn$^{12}$, Abu$^{15}$, Orn$^{21}$, Nle$^{27}$, Agm$^{29}$]hGHRH(1-29) (SEQ ID NO: 11); |
| P-20375 | [N—Me-Tyr$^1$, Thr$^8$, Orn$^{12}$, Abu$^{15}$, Orn$^{21}$, Nle$^{27}$, Agm$^{29}$]hGHRH(1-29) (SEQ ID NO: 12); |
| P-20376 | [N—Me-Tyr$^1$, Ala$^8$, Orn$^{12}$, Abu$^{15}$, Orn$^{21}$, Nle$^{27}$, Agm$^{29}$]hGHRH(1-29) (SEQ ID NO: 13); |
| P-21300 | [Dat$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$; |

P-21301 [N—Me-Tyr$^1$, Orn$^{12}$, Abu$^{15}$, Orn$^{21}$, Nle$^{27}$, Asp$^{28}$, Amc$^{30}$]hGHRH(1-30)NH$_2$ (SEQ ID NO: 14);
P-21303 [N—Me-Tyr$^1$, D-Ala$^2$, Orn$^{12}$, Abu$^{15}$, Orn$^{21}$, Nle$^{27}$, Asp$^{28}$, Amc$^{30}$]hGHRH(1-30)NH$_2$;
P-21304 [Dat$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;
P-21305 [N—Me-Tyr$^1$, D-Ala$^2$, Gln$^8$, Orn$^{12}$, Abu$^{15}$, Orn$^{21}$, Nle$^{27}$, Asp$^{28}$, Amc$^{30}$]hGHRH(1-30)NH$_2$;
P-21306 [Dat$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21307 [N—Me-Tyr$^1$, D-Ala$^2$, Thr$^8$, Orn$^{12}$, Abu$^{15}$, Orn$^{21}$, Nle$^{27}$, Asp$^{28}$, Amc$^{30}$]hGHRH(1-30)NH$_2$;
P-21308 [Dat$^1$, D-Ala$^2$, Ala$^8$, Orn$^{12}$, Abu$^{15}$, Orn$^{21}$, Nle$^{27}$, Asp$^{28}$, Amc$^{30}$]hGHRH(1-30)NH$_2$;
P-21309 [N—Me-Tyr$^1$, D-Ala$^2$, Orn$^{12}$, Ala$^8$, Abu$^{15}$, Orn$^{21}$, Nle$^{27}$, Asp$^{28}$, Amc$^{30}$]hGHRH(1-30)NH$_2$;
P-21310 [Dat$^1$-D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;
P-21311 [N—Me-Tyr$^1$, D-Ala$^2$, His$^{11}$, Orn$^{12}$, Abu$^{15}$, His$^{20}$, Orn$^{21}$, Nle$^{27}$, Asp$^{28}$, Amc$^{30}$]hGHRH(1-30)NH$_2$;
P-22325 [N—Me-Tyr$^1$, Gln$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 15);
P-22326 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22327 [Dat$^1$, Gln$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 16);
P-22328 [Ac-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-22329 [N—Me-Tyr$^1$, D-Ala$^2$, Orn$^{12}$, Abu$^{15}$, Orn$^{21}$, Nle$^{27}$, Apa$^{30}$]GHRH(1-30)NH$_2$;
P-22330 [N—Me-Tyr$^1$, D-Ala$^2$, Thr$^8$, Orn$^{12}$, Abu$^{15}$, Orn$^{21}$, Nle$^{27}$, Asp$^{28}$, Apa$^{30}$]hGHRH(1-30)NH$_2$;
P-22331 [N—Me-Tyr$^1$, D-Ala$^2$, Ala$^8$, Orn$^{12}$, Abu$^{15}$, Orn$^{21}$, Nle$^{27}$, Asp$^{28}$, Apa$^{30}$]hGHRH(1-30)NH$_2$;
P-22332 [N—Me-Tyr$^1$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 17);
P-22334 [N—Me-Tyr$^1$, Orn$^{12}$, Abu$^{15}$, Orn$^{21}$, Nle$^{27}$, Apa$^{30}$]GHRH(1-30)NH$_2$ (SEQ ID NO: 18);
P-22335 [N—Me-Tyr$^1$, Thr$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 19);
P-22336 [N—Me-Tyr$^1$, Ala$^8$, Orn$^{12}$, Abu$^{15}$, Orn$^{21}$, Nle$^{27}$, Asp$^{28}$, Apa$^{30}$]hGHRH(1-30)NH$_2$ (SEQ ID NO: 20);
P-22337 [N—Me-Tyr$^1$, D-Ala$^2$, Cpa$^6$, Gln$^8$, Orn$^{12}$, Abu$^{15}$, Orn$^{21}$, Nle$^{27}$, Asp$^{28}$, Apa$^{30}$]hGHRH(1-30)NH$_2$;
P-23250 [Dat$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23251 [Dat$^1$, Gln$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 21);
P-23252 [Dat$^1$-D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23253 [Dat$^1$, Orn$^{12}$, Abu$^{15}$, Orn$^{21}$, Nle$^{27}$, Asp$^{28}$, Har$^{30}$]hGHRH(1-30)NH$_2$ (SEQ ID NO: 22);
P-23254 [Dat$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23255 [Dat$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 23);
P-23256 [Dat$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23257 [Dat$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 24);
P-23258 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH$_2$;
P-23259 [N—Me-Tyr$^1$, Gln$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 25);
P-23260 [N—Me-Tyr$^1$, D-Ala$^2$, Orn$^{12}$, Abu$^{15}$, Orn$^{21}$, Nle$^{27}$, Asp$^{28}$, Har$^{30}$]hGHRH(1-30)NH$_2$;
P-23261 [N—Me-Tyr$^1$, Orn$^{12}$, Abu$^{15}$, Orn$^{21}$, Nle$^{27}$, Asp$^{28}$, Har$^{30}$]hGHRH(1-30)NH$_2$ (SEQ ID NO: 26);
P-23262 [N—Me-Tyr$^1$, D-Ala$^2$, Thr$^8$, Orn$^{12}$, Abu$^{15}$, Orn$^{21}$, Nle$^{27}$, Asp$^{28}$, Har$^{30}$]hGHRH(1-30)NH$_2$;
P-23263 [N—Me-Tyr$^1$, Thr$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 27);
P-23264 [N—Me-Tyr$^1$, D-Ala$^2$, Ala$^8$, Orn$^{12}$, Abu$^{15}$, Orn$^{21}$, Nle$^{27}$, Asp$^{28}$, Har$^{30}$]hGHRH(1-30)NH$_2$;
P-23265 [N—Me-Tyr$^1$, Ala$^8$, Orn$^{12}$, Abu$^{15}$, Orn$^{21}$, Nle$^{27}$, Asp$^{28}$, Har$^{30}$]hGHRH(1-30)NH$_2$ (SEQ ID NO: 28);
P-24340 [N—Me-Tyr$^1$, Gln$^8$, Orn$^{12}$, Abu$^{15}$, Orn$^{21}$, Nle$^{27}$, Asp$^{28}$, Aha$^{30}$]hGHRH(1-30)NH$_2$ (SEQ ID NO: 29);
P-24341 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24342 [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$ (SEQ ID NO: 30);

P-24344 [Dat$^1$, Gln$^8$, Orn$^{12}$, Abu$^{15}$, Orn$^{21}$, Nle$^{27}$, Asp$^{28}$, Aha$^{30}$]hGHRH(1-30)NH$_2$;

P-24345 [N—Me-Tyr$^1$, D-Ala$^2$, Orn$^{12}$, Abu$^{15}$, Orn$^{21}$, Nle$^{27}$, Asp$^{28}$, Aha$^{30}$]hGHRH(1-30)NH$_2$;

P-24346 [N—Me-Tyr$^1$, D-Ala$^2$, Gln$^8$, Orn$^{12}$, Abu$^{15}$, Orn$^{21}$, Nle$^{27}$, Aha$^{30}$]hGHRH(1-30)NH$_2$;

P-24347 [N—Me-Tyr$^1$, D-Ala$^2$, Thr$^8$, Orn$^{12}$, Abu$^{15}$, Orn$^{21}$, Nle$^{27}$, Asp$^{28}$, Aha$^{30}$]hGHRH(1-30)NH$_2$;

P-24348 [N—Me-Tyr$^1$, D-Ala$^2$, Ala$^8$, Orn$^{12}$, Abu$^{15}$, Orn$^{21}$, Nle$^{27}$, Asp$^{28}$, Aha$^{30}$]hGHRH(1-30)NH$_2$;

P-25501 [N—Me-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25502 [Dat$^1$, D-Ala$^2$, Fpa5$^6$, Orn$^{12}$, Abu$^{15}$, Orn$^{21}$, Nle$^{27}$, Gab$^{30}$]hGHRH(1-30)NH$_2$;

P-25503 [N—Me-Tyr$^1$, Abu$^2$, Orn$^{12}$, Abu$^{15}$, Orn$^{21}$, Nle$^{27}$, Gab$^{30}$]hGHRH(1-30)NH$_2$ (SEQ ID NO: 31);

P-25504 [Dat$^1$, D-Abu$^2$, Orn$^{12}$, Abu$^{15}$, Orn$^{21}$, Nle$^{27}$, Gab$^{30}$]hGHRH(1-30)NH$_2$;

P-25506 [N—Me-Tyr$^1$, D-Abu$^2$, Orn$^{12}$, Abu$^{15}$, Orn$^{21}$, Nle$^{27}$, Gab$^{30}$]hGHRH(1-30)NH$_2$;

P-25508 [Tfa-Tyr$^1$, D-Ala$^2$, Orn$^{12}$, Abu$^{15}$, Orn$^{21}$, Nle$^{27}$, Gab$^{30}$]hGHRH(1-30)NH$_2$;

P-25516 [N—Me-Tyr$^1$, D-Ala$^2$, Orn$^{12}$, Abu$^{15}$, Orn$^{21}$, Nle$^{27}$, Asp$^{28}$, Gab$^{30}$]hGHRH(1-30)NH$_2$;

P-26802 [Dat$^1$, D-Ala$^2$, Thr$^8$, His$^{11}$, Orn$^{12}$, Abu$^{15}$, His$^{20}$, Orn$^{21}$, Nle$^{27}$, Ada$^{30}$]hGHRH(1-30)NH$_2$;

P-26803 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Ada$^{30}$]hGHRH(1-30)NH—CH$_3$;

P-26804 [N—Me-Tyr$^1$, D-Ala$^2$, Orn$^{12}$, Abu$^{15}$, Orn$^{21}$, Nle$^{27}$, Ada$^{30}$]hGHRH(1-30)NH$_2$;

P-27400 [Dat$^1$, D-Ala$^2$, Orn$^{12}$, Abu$^{15}$, Orn$^{21}$, Nle$^{27}$, Asp$^{28}$]hGHRH(1-29)NH—CH$_3$;

P-27401 [Dat$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27403 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27404 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27405 [N—Me-Tyr$^1$, Gln$^8$, Orn$^{12}$, Abu$^{15}$, Orn$^{21}$, Nle$^{27}$]hGHRH(1-29)NH—CH$_3$ (SEQ ID NO: 32);

P-27406 [N—Me-Tyr$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 33);

P-27407 [Dat$^1$, Gln$^8$, Orn$^{12}$, Abu$^{15}$, Orn$^{21}$, Nle$^{27}$, Asp$^{28}$]hGHRH(1-29)NH—CH$_3$ (SEQ ID NO: 34);

P-27408 [Dat$^1$, D-Ala$^2$, Gln$^8$, Orn$^{12}$, Abu$^{15}$, Orn$^{21}$, Nle$^{27}$, Asp$^{28}$]hGHRH(1-30)NH—CH$_3$;

P-27409 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27410 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_3$;

P-27411 [N—Me-Tyr$^1$, D-Ala$^2$, Thr$^8$, Orn$^{12}$, Abu$^{15}$, Orn$^{21}$, Nle$^{27}$]hGHRH(1-29)NH—CH$_3$;

P-27412 [N—Me-Tyr$^1$, D-Ala$^2$, Ala$^8$, Orn$^{12}$, Abu$^{15}$, Orn$^{21}$, Nle$^{27}$, Asp$^{28}$]hGHRH(1-29)NH—CH$_3$;

P-27413 [Dat$^1$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$ (SEQ ID NO: 35);

P-27414 [N—Me-Tyr$^1$, D-Ala$^2$, Fpa5$^6$, Orn$^{12}$, Abu$^{15}$, Orn$^{21}$, Nle$^{27}$, Gab$^{30}$]hGHRH(1-30)NH—CH$_3$;

P-27415 [N—Me-Tyr$^1$, Orn$^{12}$, Abu$^{15}$, Orn$^{21}$, Nle$^{27}$, Gab$^{30}$]hGHRH(1-30)NH—CH$_3$ (SEQ ID NO: 36);

P-27416 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$]hGHRH(1-29)NH—CH$_3$;

P-27417 [Ac-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27418 [Ac-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_3$;

P-27419 [Ac-Tyr$^1$, Thr$^8$, Orn$^{12}$, Abu$^{15}$, Orn$^{21}$, Nle$^{27}$]hGHRH(1-29)NH—CH$_3$ (SEQ ID NO: 37);

P-27422 [N—Me-D-Tyr$^1$, Gln$^8$, Orn$^{12}$, Abu$^{15}$, Orn$^{21}$, Nle$^{27}$, Asp$^{28}$]hGHRH(1-29)NH—CH$_3$;

P-27423 [N—Me-D-Tyr$^1$, D-Ala$^2$, Orn$^{12}$, Abu$^{15}$, Orn$^{21}$, Nle$^{27}$, Asp$^{28}$]hGHRH(1-29)NH—CH$_3$;

P-27424 [Dat$^1$, Thr$^8$, Orn$^{12}$, Abu$^{15}$, Orn$^{21}$, Nle$^{27}$]hGHRH(1-29)NH—CH$_3$ (SEQ ID NO: 38);

P-27425 [N—Me-D-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_3$;

P-27440 [Dat$^1$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27441 [N—Me-Tyr$^1$, D-Ala$^2$, Gln$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27442 [N—Me-Tyr$^1$, D-Ala$^2$, Fpa5$^6$, Orn$^{12}$, Abu$^{15}$, Orn$^{21}$, Nle$^{27}$, Asp$^{28}$, D-Arg$^{29}$]hGHRH(1-29)NH—CH$_3$;

P-27443 [N—Me-Tyr$^1$, Orn$^{12}$, Abu$^{15}$, Orn$^{21}$, Nle$^{27}$, D-Arg$^{29}$]hGHRH(1-29)NH—CH$_3$;

P-27444 [N—Me-Tyr$^1$, D-Ala$^2$, Orn$^{12}$, Abu$^{15}$, Orn$^{21}$, Nle$^{27}$, Asp$^{28}$, D-Arg$^{29}$]hGHRH(1-29)NH—CH$_3$;

P-27445 [N—Me-Tyr$^1$, D-Ala$^2$, Thr$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27446 [N—Me-Tyr$^1$, D-Ala$^2$, Ala$^8$, Orn$^{12}$, Abu$^{15}$, Orn$^{21}$, Nle$^{27}$, Asp$^{28}$, D-Arg$^{29}$]hGHRH(1-29)NH—CH$_3$;

P-27447 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_3$;

-continued

P-27448 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_3$;
P-27449 [N—Me-Tyr$^1$, D-Ala$^2$, Gln$^8$, Orn$^{12}$, Abu$^{15}$, Orn21, Nle$^{27}$, Asp$^{28}$, Amc$^{30}$]hGHRH(1-30)NH—CH$_3$;
P-27450 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_3$;
P-27451 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_3$;
P-28420 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28421 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28430 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28431 [N—Me-Tyr$^1$, D-Ala$^2$, Thr$^8$, Orn$^{12}$, Abu$^{15}$, Orn$^{21}$, Nle$^{27}$, Asp$^{28}$]hGHRH(1-29)NH—CH$_2$—CH$_3$;
P-28460 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28461 [N—Me-Tyr$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28462 [N—Me-Tyr$^1$, D-Ala$^2$, Fpa5$^6$, Orn$^{12}$, Abu$^{15}$, Orn$^{21}$, Nle$^{27}$]hGHRH(1-29) NH—CH$_2$—CH$_3$;
P-28463 [N—Me-Tyr$^1$, D-Ala$^2$, Orn$^{12}$, Abu$^{15}$, Orn$^{21}$, Nle$^{27}$]hGHRH(1-29)NH—CH$_2$—CH$_3$;
P-28464 [N—Me-Tyr$^1$, D-Ala$^2$, Fpa5$^6$, Gln$^8$, Orn$^{12}$, Abu$^{15}$, Orn$^{21}$, Nle$^{27}$]hGHRH(1-29)NH—CH$_2$—CH$_3$;
P-28465 [N—Me-Tyr$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28466 [N—Me-Tyr$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28467 [N—Me-Tyr$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28468 [N—Me-Tyr$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28469 [Dat$^1$, D-Ala$^2$, Gln$^8$, Orn$^{12}$, Abu$^{15}$, Orn$^{21}$, Nle$^{27}$]hGHRH(1-29)NH—CH$_2$—CH$_3$;
P-28470 [Dat$^1$, D-Ala$^2$, Orn$^{12}$, Abu$^{15}$, Orn$^{21}$, Nle$^{27}$]hGHRH(1-29)NH—CH$_2$—CH$_3$;
P-28471 [Dat$^1$, D-Ala$^2$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28472 [Dat$^1$, D-Ala$^2$, Fpa5$^6$, Gln$^8$, Orn$^{12}$, Abu$^{15}$, Orn$^{21}$, Nle$^{27}$, Asp$^{28}$]hGHRH(1-29)NH—CH$_2$—CH$_3$;
P-28473 [Dat$^1$, D-Ala$^2$, Fpa5$^6$, Orn$^{12}$, Abu$^{15}$, Orn$^{21}$, Nle$^{27}$, Asp$^{28}$]hGHRH(1-29)NH—CH$_2$—CH$_3$;
P-28474 [Dat$^1$, D-Ala$^2$, Orn$^{12}$, Abu$^{15}$, Orn$^{21}$, Nle$^{27}$, Asp$^{28}$]hGHRH(1-29)NH—CH$_2$—CH$_3$;
P-28475 [N—Me-Tyr$^1$, D-Ala$^2$, Gln$^8$, Orn$^{12}$, Abu$^{15}$, Orn$^{21}$, Nle$^{27}$, Asp$^{28}$, Apa$^{30}$]hGHRH(1-30)NH—CH$_2$—CH$_3$;
P-28476 [N—Me-Tyr$^1$, D-Ala$^2$, Gln$^8$, Orn$^{12}$, Abu$^{15}$, Orn$^{21}$, Nle$^{27}$, Asp$^{28}$, Aha$^{30}$]hGHRH(1-30)NH—CH$_2$—CH$_3$;
P-28477 [N—Me-Tyr$^1$, D-Ala$^2$, Gln$^8$, Orn$^{12}$, Abu$^{15}$, Orn$^{21}$ Nle$^{27}$, Asp$^{28}$, Amc$^{30}$]hGHRH(1-30)NH—CH$_2$—CH$_3$;
P-28478 [N—Me-Tyr$^1$, D-Ala$^2$, Gln$^8$, Orn$^{12}$, Abu$^{15}$, Orn$^{21}$, Nle$^{27}$, Asp$^{28}$, Har$^{30}$]hGHRH(1-30)NH—CH$_2$—CH$_3$;
P-28479 [N—Me-Tyr$^1$, D-Ala$^2$, Gln$^8$, His$^{11}$, Orn$^{12}$, Abu$^{15}$, His$^{20}$, Orn$^{21}$, Nle$^{27}$, Asp$^{28}$, Apa$^{30}$]hGHRH(1-30)NH—CH$_2$—CH$_3$;
P-29701 [N—Me-Tyr$^1$, D-Ala$^2$, Gln$^8$, Orn$^{12}$, Abu$^{15}$, Orn$^{21}$, Nle$^{27}$, Asp$^{28}$, Gln-Gab$^{30}$]hGHRH](1-30)NH$_2$;
P-29702 [Dat$^1$, D-Ala$^2$, Orn$^{12}$, Abu$^{15}$, Orn$^{21}$, Nle$^{27}$, Gln-Gab$^{30}$]hGHRH(1-30)NH$_2$;
P-29703 [N—Me-Tyr$^1$, Gln$^8$, Orn$^{12}$, Abu$^{15}$, Orn$^{21}$, Nle$^{27}$, Gln-Gab$^{30}$]hGHRH(1-30)NH$_2$ (SEQ ID NO: 39);
P-29704 [Dat$^1$, D-Ala$^2$, Gln$^8$, Orn$^{12}$, Abu$^{15}$, Orn$^{21,22}$, Nle$^{27}$, Gln-Gab$^{30}$]hGHRH(1-30)NH$_2$;
P-29706 [Dat$^1$, D-Abu$^2$, Gln$^8$, Orn$^{12}$, Abu$^{15}$, Orn$^{21}$, Nle$^{27}$, Gln-Gab$^{30}$]hGHRH(1-30)NH$_2$;
P-29708 [N—Me-Tyr$^1$, D-Ala$^2$, Fpa5$^6$, Orn$^{12}$, Abu$^{15}$, Orn$^{21}$, Nle$^{27}$, Gln-Gab$^{30}$]hGHRH(1-30)NH$_2$;
P-29710 [N—Me-Tyr$^1$, D-Ala$^2$, Fpa5$^6$, Ala$^8$, Orn$^{12}$, Abu$^{15}$, Orn$^{21}$, Nle$^{27}$, Gln-Gab$^{30}$]hGHRH(1-30)NH$_2$;
P-29720 [Dat$^1$, D-Ala$^2$, Orn$^{12}$, Abu$^{15}$, Orn$^{21}$, Nle$^{27}$, Asp$^{28}$, Gln-Gab$^{30}$]hGHRH(1-30)NH$_2$;
P-29721 [Dat$^1$, D-Ala$^2$, Gln$^8$, Orn$^{12}$, Abu$^{15}$, Orn$^{21,22}$, Nle$^{27}$, Asp$^{28}$, Gln-Gab$^{30}$]hGHRH(1-30)NH$_2$;
P-29722 [Dat$^1$, D-Abu$^2$, Gln$^8$, Orn$^{12}$, Abu$^{15}$, Orn$^{21}$, Nle$^{27}$, Asp$^{28}$, Gln$^{30}$, Gab$^{30}$]hGHRH(1-30)NH$_2$;
P-29723 [N—Me-Tyr$^1$, D-Ala$^2$, Fpa5$^6$, Orn$^{12}$, Abu$^{15}$, Orn$^{21}$, Nle$^{27}$, Asp$^{28}$, Gln-Gab$^{30}$]hGHRH(1-30)NH$_2$;

| | |
|---|---|
| P-29724 | [N—Me-Tyr¹, D-Ala², Fpa5⁶, Ala⁸, Orn¹², Abu¹⁵, Orn²¹, Nle²⁷, Asp²⁸, Gln-Gab³⁰]hGHRH(1-30)NH₂, | and pharmaceutically acceptable salts thereof.

22. The method of claim 21, wherein GHRH agonist peptide is selected from the group having the formula:

| | |
|---|---|
| P-20367 | [N—Me-Tyr¹, D-Ala², Orn¹², Abu¹⁵, Orn²¹, Nle²⁷, Asp²⁸, Agm²⁹]hGHRH(1-29); |
| P-20361 | [N—Me-Tyr¹, D-Ala², Gln⁸, Orn¹², Abu¹⁵, Orn²¹, Nle²⁷, Asp²⁸, Agm²⁹]hGHRH(1-29); |
| P-27406 | [N—Me-Tyr¹, Gln⁸, Orn¹², Abu¹⁵, Orn²¹, Nle²⁷, Asp²⁸, Agm²⁹]hGHRH(1-29)NH—CH₃ (SEQ ID NO: 33); |
| P-28420 | [N—Me-Tyr¹, D-Ala², Gln⁸, Orn¹², Abu¹⁵, Orn²¹, Nle²⁷, Asp²⁸]hGHRH(1-29)NH—CH₂—CH₃; |
| P-28421 | [N—Me-Tyr¹, D-Ala², Orn¹², Abu¹⁵, Orn²¹, Nle²⁷, Asp²⁸]hGHRH(1-29)NH—CH₂—CH₃; |
| P-27403 | [N—Me-Tyr¹, D-Ala², Gln⁸, Orn¹², Abu¹⁵, Orn²¹, Nle²⁷, Asp²⁸]hGHRH(1-29)NH—CH₃; |
| P-27409 | [N—Me-Tyr¹, D-Ala², Orn¹², Abu¹⁵, Orn²¹, Nle²⁷, Asp²⁸]hGHRH(1-29)NH—CH₃; |
| P-20356 | [N—Me-Tyr¹, Gln⁸, Orn¹², Abu¹⁵, Orn²¹, Nle²⁷, Asp²⁸, Agm²⁹]hGHRH(1-29) (SEQ ID NO: 6); and |
| P-25502 | [Dat¹, D-Ala², Fpa5⁶, Orn¹², Abu¹⁵, Orn²¹, Nle²⁷, Gab³⁰]hGHRH(1-30)NH₂. |

\* \* \* \* \*

SEQUENCE LISTING

```
<160> NUMBER OF SEQ ID NOS: 39

<210> SEQ ID NO 1
<211> LENGTH: 30
<212> TYPE: PRT
<213> ORGANISM: Artificial Sequence
<220> FEATURE:
<223> OTHER INFORMATION: synthetic peptide

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln
            20                  25                  30
```

<210> SEQ ID NO 2
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 2

Xaa Ala Asp Ala Ile Xaa Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)

<223> OTHER INFORMATION: Xaa is agmatine

<400> SEQUENCE: 3

Xaa Ala Asp Ala Ile Xaa Thr Ala Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 4

Xaa Ala Asp Ala Ile Xaa Thr Asn Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (6)..(6)
<223> OTHER INFORMATION: Xaa is pentafluoro-Phe
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 5

Xaa Ala Asp Ala Ile Xaa Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 6

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:

```
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 7

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 8

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
```

<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 9

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 10

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)

-continued

```
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 11

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 12

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
```

```
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is agmatine

<400> SEQUENCE: 13

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 14
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 8-Aminocaprylyl-NH2

<400> SEQUENCE: 14

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
```

<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 15

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 16

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine

```
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 17

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 18

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
```

```
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 19

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 5-Aminopentanoyl-NH2

<400> SEQUENCE: 20

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 21
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
```

```
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 21

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 22

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
```

```
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 23

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 24

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
```

```
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 25

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 26

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 27

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is homoarginine-NH2

<400> SEQUENCE: 28

Xaa Ala Asp Ala Ile Phe Thr Ala Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE

```
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 6-aminohexanoyl-NH2

<400> SEQUENCE: 29

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is 6-aminohexanoyl-NH2

<400> SEQUENCE: 30

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Arg Xaa
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (2)..(2)
<223> OTHER INFORMATION: Xaa is alpha-aminobutyric acid
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is gamma-amino butanoyl-NH2

<400> SEQUENCE: 31

Xaa Xaa Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30

<210> SEQ ID NO 32
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 32

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 33
<211> LENGTH: 29
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 33

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 34
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 34

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Asp Xaa
            20                  25

<210> SEQ ID NO 35
```

```
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 35

Xaa Ala Asp Ala Ile Phe Thr Gln Ser Tyr His Xaa Val Leu Xaa Gln
1               5                   10                  15

Leu Ser Ala His Xaa Leu Leu Gln Asp Ile Xaa Asp Xaa
            20                  25

<210> SEQ ID NO 36
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is gamma-amino butanoyl-NH-CH3

<400> SEQUENCE: 36

Xaa Ala Asp Ala Ile Phe Thr Asn Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30
```

```
<210> SEQ ID NO 37
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is acetyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 37

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is des-amino-tyrosine
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (29)..(29)
<223> OTHER INFORMATION: Xaa is Arg-NH-CH3

<400> SEQUENCE: 38

Xaa Ala Asp Ala Ile Phe Thr Thr Ser Tyr Arg Xaa Val Leu Xaa Gln
1               5                   10                  15

Leu Ser Ala Arg Xaa Leu Leu Gln Asp Ile Xaa Ser Xaa
            20                  25
```

```
<210> SEQ ID NO 39
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is N-methyl-Tyr
<220> FEATURE:
<221> NAME/KEY: MISC_FEATURE
<222> LOCATION: (12)..(12)
<223> OTHER INFORMATION: Xaa is ornithine
<220> FEATURE:
<221> NAME/KEY: MISC_FEATURE
<222> LOCATION: (15)..(15)
<223> OTHER INFORMATION: Xaa is alpha-aminobutyric acid
<220> FEATURE:
<221> NAME/KEY: MISC_FEATURE
<222> LOCATION: (21)..(21)
<223> OTHER INFORMATION: Xaa is ornithine
<220> FEATURE:
<221> NAME/KEY: MISC_FEATURE
<222> LOCATION: (27)..(27)
<223> OTHER INFORMATION: Xaa is norleucine
<220> FEATURE:
<221> NAME/KEY: MISC_FEATURE
<222> LOCATION: (30)..(30)
<223> OTHER INFORMATION: Xaa is Gln-gamma-amino butanoyl-NH2

<400> SEQUENCE: 39

Xaa Ala Asp Ala Ile Phe Thr Gln Ser Tyr Arg Xaa Val Leu Xaa Gln
1               5                   10                  15

Leu Ser Ala Arg Xaa Leu Leu Gln Asp Ile Xaa Ser Arg Xaa
            20                  25                  30
```